United States Patent
Behzadi

(10) Patent No.: US 10,682,071 B2
(45) Date of Patent: *Jun. 16, 2020

(54) STATE CHARACTERIZATION BASED ON MULTI-VARIATE DATA FUSION TECHNIQUES

(71) Applicant: Proteus Digital Health, Inc., Redwood City, CA (US)

(72) Inventor: Yashar Behzadi, San Francisco, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/469,052

(22) Filed: Mar. 24, 2017

(65) Prior Publication Data

US 2017/0303818 A1    Oct. 26, 2017

Related U.S. Application Data

(63) Continuation of application No. 13/844,386, filed on Mar. 15, 2013, now Pat. No. 9,603,550.

(51) Int. Cl.
*A61B 5/07* (2006.01)
*G06F 19/00* (2018.01)
(Continued)

(52) U.S. Cl.
CPC ............. *A61B 5/07* (2013.01); *A61B 5/0022* (2013.01); *G06F 19/3456* (2013.01); *A61B 5/021* (2013.01); *G06F 19/3418* (2013.01)

(58) Field of Classification Search
CPC .......... A61B 5/0022; A61B 5/07; G06F 19/34
See application file for complete search history.

(56) References Cited

U.S. PATENT DOCUMENTS 3,218,638 A  11/1965  Honig
3,345,989 A  10/1967  Reynolds
(Continued)

FOREIGN PATENT DOCUMENTS

CA  2953847  11/2006
CN  1588649  3/2005
(Continued)

OTHER PUBLICATIONS

Aade, "AADE 37th Annual Meeting San Antonio Aug. 4-7, 2010" American Association of Diabetes Educators Aug. 2010; http://www.diabeteseducator.org/annualmeeting/2010/index.html; 2 pp.

(Continued)

*Primary Examiner* — Christian Jang
(74) *Attorney, Agent, or Firm* — K&L Gates LLP

(57) ABSTRACT

The disclosed system includes an ingestible event marker device configured to collect Ingestible Event Marker (IEM) data from a body of an individual and transmit a signal including the IEM data, wherein the IEM data include information associated with an ingestion event, a receiver adapted to be associated with the body of the individual and configured to receive the signal including the IEM data via the body of the individual, a hub to receive the IEM data from the receiver, and at least one IEM data system to receive the IEM data from the hub. The at least one IEM data system analyzes the IEM data and generates at least one metric based on the IEM data. The at least one IEM data system may further generate predictive information based on the at least one metric, wherein the predictive information is related to prediction of a state of the individual.

25 Claims, 25 Drawing Sheets

(51) Int. Cl.
*A61B 5/00* (2006.01)
*A61B 5/021* (2006.01)

(56) References Cited

U.S. PATENT DOCUMENTS

| | | | |
|---|---|---|---|
| 3,353,539 A | 11/1967 | Preston |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,538,007 A | 7/1996 | Gorman |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,701 A | 6/1999 | Gersheneld et al. |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |

(56) References Cited

U.S. PATENT DOCUMENTS

| | | |
|---|---|---|
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,069,062 B2 | 6/2006 | Minotani et al. |
| 7,076,437 B1 | 7/2006 | Levy |
| 7,081,693 B2 | 7/2006 | Hamel et al. |
| 7,091,726 B2 | 8/2006 | Sano et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |

(56) References Cited

U.S. PATENT DOCUMENTS

| | | |
|---|---|---|
| 7,285,090 B2 | 10/2007 | Stivoric et al. |
| 7,289,855 B2 | 10/2007 | Nghiem |
| 7,291,014 B2 | 11/2007 | Chung et al. |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,449,262 B2 | 11/2008 | Christie et al. |
| 7,462,150 B1 | 12/2008 | Bharmi |
| 7,471,665 B2 | 12/2008 | Perlman |
| 7,485,093 B2 | 2/2009 | Glukhovsky |
| 7,485,095 B2 | 2/2009 | Shusterman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,558,622 B2 | 7/2009 | Tran |
| 7,558,965 B2 | 7/2009 | Wheeler et al. |
| 7,575,005 B2 | 8/2009 | Mumford |
| 7,614,743 B2 | 11/2009 | Geiger |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,683,761 B2 | 2/2010 | Burghard et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,764,996 B2 | 7/2010 | Zhang et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,811,231 B2 | 10/2010 | Jin et al. |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,871,734 B2 | 1/2011 | Hertz et al. |
| 7,899,526 B2 | 3/2011 | Benditt et al. |
| 7,904,133 B2 | 3/2011 | Gehman et al. |
| D639,437 S | 6/2011 | Bishay et al. |
| 7,978,064 B2 | 7/2011 | Zdeblick et al. |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,055,334 B2 | 11/2011 | Savage et al. |
| 8,060,249 B2 | 11/2011 | Bear et al. |
| 8,073,707 B2 | 12/2011 | Teller et al. |
| 8,083,128 B2 | 12/2011 | Dembo et al. |
| 8,123,576 B2 | 2/2012 | Kim |
| 8,135,596 B2 | 3/2012 | Jung et al. |
| 8,142,513 B2 | 3/2012 | Shalon et al. |
| 8,177,611 B2 | 5/2012 | Kang |
| 8,180,425 B2 | 5/2012 | Selvitelli et al. |
| 8,185,191 B1 | 5/2012 | Shapiro et al. |
| 8,185,646 B1 | 5/2012 | Headley |
| 8,200,320 B2 | 6/2012 | Kovacs |
| 8,209,018 B2 | 6/2012 | Osorio et al. |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2 | 8/2012 | Rofougaran |
| 8,258,962 B2 | 9/2012 | Robertson et al. |
| 8,262,394 B2 | 9/2012 | Walker et al. |
| 8,271,106 B2 | 9/2012 | Wehba et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,440,274 B2 | 5/2013 | Wang |
| 8,454,528 B2 | 6/2013 | Yuen et al. |
| 8,454,561 B2 | 6/2013 | Uber, III et al. |
| 8,514,086 B2 | 8/2013 | Harper et al. |
| 8,542,123 B2 | 9/2013 | Robertson |
| 8,545,402 B2 | 10/2013 | Hafezi et al. |
| 8,564,432 B2 | 10/2013 | Covannon et al. |
| 8,564,627 B2 | 10/2013 | Suzuki et al. |

(56) References Cited

U.S. PATENT DOCUMENTS

| | | |
|---|---|---|
| 8,583,227 B2 | 11/2013 | Savage et al. |
| 8,597,186 B2 | 12/2013 | Hafezi et al. |
| 8,634,838 B2 | 1/2014 | Hellwig et al. |
| 8,660,645 B2 | 2/2014 | Stevenson et al. |
| 8,668,280 B2 | 3/2014 | Heller et al. |
| 8,668,643 B2 | 3/2014 | Kinast |
| 8,718,193 B2 | 5/2014 | Arne et al. |
| 8,722,085 B2 | 5/2014 | McKinney et al. |
| 8,762,733 B2 | 6/2014 | Derchak et al. |
| 8,771,183 B2 | 7/2014 | Sloan |
| 8,810,260 B1 | 8/2014 | Zhou |
| 8,810,409 B2 | 8/2014 | Robertson et al. |
| 8,823,510 B2 | 9/2014 | Downey et al. |
| 8,836,513 B2 | 9/2014 | Hafezi et al. |
| 8,838,217 B2 | 9/2014 | Myr |
| 8,858,432 B2 | 10/2014 | Robertson |
| 8,868,453 B2 | 10/2014 | Zdeblick |
| 8,908,943 B2 | 12/2014 | Berry et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,956,287 B2 | 2/2015 | Zdeblick et al. |
| 8,966,973 B1 | 3/2015 | Milone |
| 8,989,837 B2 | 3/2015 | Weinstein et al. |
| 9,031,658 B2 | 5/2015 | Chiao et al. |
| 9,047,746 B1 | 6/2015 | Euliano et al. |
| 9,060,708 B2 | 6/2015 | Robertson et al. |
| 9,083,589 B2 | 7/2015 | Arne et al. |
| 9,088,168 B2 | 7/2015 | Mach et al. |
| 9,119,918 B2 | 9/2015 | Robertson et al. |
| 9,125,868 B2 | 9/2015 | McKinney et al. |
| 9,189,941 B2 | 11/2015 | Eschelman et al. |
| 9,198,608 B2 | 12/2015 | Hafezi et al. |
| 9,226,663 B2 | 1/2016 | Fei |
| 9,226,679 B2 | 1/2016 | Balda |
| 9,235,683 B2 | 1/2016 | Robertson et al. |
| 9,258,035 B2 | 2/2016 | Robertson et al. |
| 9,270,025 B2 | 2/2016 | Robertson et al. |
| 9,277,864 B2 | 3/2016 | Yang et al. |
| 9,278,177 B2 | 3/2016 | Edwards et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,444,503 B2 | 9/2016 | Arne et al. |
| 9,517,012 B2 | 12/2016 | Lane et al. |
| 9,597,010 B2 | 3/2017 | Thompson et al. |
| 9,603,550 B2 * | 3/2017 | Behzadi ............ G06F 19/3456 |
| 9,883,819 B2 | 2/2018 | Jensen et al. |
| 1,018,712 A1 | 1/2019 | Shirvani et al. |
| 1,022,390 A1 | 3/2019 | Zdeblick et al. |
| 2001/0027331 A1 | 10/2001 | Thompson |
| 2001/0031071 A1 | 10/2001 | Nichols et al. |
| 2001/0039503 A1 | 11/2001 | Chan et al. |
| 2001/0044588 A1 | 11/2001 | Mault |
| 2001/0051766 A1 | 12/2001 | Gazdzinski |
| 2001/0056262 A1 | 12/2001 | Cabiri et al. |
| 2002/0002326 A1 | 1/2002 | Causey et al. |
| 2002/0019586 A1 | 2/2002 | Teller et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0067270 A1 | 6/2002 | Yarin et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0138009 A1 | 9/2002 | Brockway et al. |
| 2002/0184415 A1 | 12/2002 | Naghavi et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0037063 A1 | 2/2003 | Schwartz |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0198619 A1 | 10/2003 | Dong et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0216793 A1 | 11/2003 | Karlsson et al. |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0122296 A1 | 6/2004 | Hatlestad |
| 2004/0122297 A1 | 6/2004 | Stahmann et al. |
| 2004/0138558 A1 | 7/2004 | Dunki-Jacobs et al. |
| 2004/0147326 A1 | 7/2004 | Stiles |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |

(56) References Cited

U.S. PATENT DOCUMENTS

| | | |
|---|---|---|
| 2005/0038321 A1 | 2/2005 | Fujita et al. |
| 2005/0038680 A1 | 2/2005 | McMahon |
| 2005/0043583 A1 | 2/2005 | Killman et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0204764 A1 | 9/2006 | Hirao et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0172424 A1 | 7/2007 | Roser |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |

(56) References Cited

U.S. PATENT DOCUMENTS

| | | |
|---|---|---|
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1* | 5/2008 | Bandy ............. A61B 1/00016 600/302 |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |

(56) References Cited

U.S. PATENT DOCUMENTS

| | | |
|---|---|---|
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0011699 A1 | 1/2012 | Hafezi et al. |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelson et al. |

(56) References Cited

U.S. PATENT DOCUMENTS

| | | |
|---|---|---|
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0073312 A1 | 3/2013 | Thompson et al. |
| 2013/0171596 A1 | 7/2013 | French |
| 2013/0185228 A1 | 7/2013 | Dresner |
| 2013/0196012 A1 | 8/2013 | Dill |
| 2013/0275296 A1 | 10/2013 | Tietzen et al. |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0203950 A1 | 7/2014 | Zdeblick et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0349256 A1 | 11/2014 | Connor |
| 2014/0374276 A1 | 12/2014 | Guthrie et al. |
| 2015/0051465 A1 | 2/2015 | Robertson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0165313 A1 | 6/2015 | Thompson et al. |
| 2015/0171924 A1 | 6/2015 | Zdeblick |
| 2015/0182463 A1 | 7/2015 | Hafezi et al. |
| 2015/0193593 A1 | 7/2015 | Zdeblick et al. |
| 2015/0230728 A1 | 8/2015 | Hafezi et al. |
| 2016/0106339 A1 | 4/2016 | Behzadi et al. |
| 2016/0155316 A1 | 6/2016 | Hafezi et al. |
| 2017/0000180 A1 | 1/2017 | Arne et al. |
| 2017/0215761 A1 | 8/2017 | Zdeblick |
| 2017/0290513 A1 | 10/2017 | O'Reilly et al. |
| 2018/0184698 A1 | 7/2018 | Arne et al. |
| 2018/0279910 A1 | 10/2018 | Jensen et al. |

FOREIGN PATENT DOCUMENTS

| | | |
|---|---|---|
| CN | 2748032 | 12/2005 |
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | 2000506410 | 5/1912 |
| JP | S6117949 | 1/1986 |
| JP | S63280393 | 11/1988 |
| JP | H01285247 | 11/1989 |
| JP | 05228128 | 9/1993 |
| JP | H0884779 | 4/1996 |
| JP | 09330159 | 12/1997 |
| JP | 1014898 | 1/1998 |
| JP | H11195415 | 7/1999 |
| JP | 2001078974 | 3/2001 |
| JP | 2002224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 3454525 | 10/2003 |
| JP | 2003325440 | 11/2003 |
| JP | 2004007187 | 1/2004 |
| JP | 2004507188 | 3/2004 |
| JP | 2004134384 | 4/2004 |
| JP | 2004274452 | 9/2004 |
| JP | 2004313242 | 11/2004 |
| JP | 2004318534 | 11/2004 |
| JP | 2004364016 | 12/2004 |
| JP | 2005031840 | 2/2005 |
| JP | 2005073886 | 3/2005 |
| JP | 2005124708 | 5/2005 |
| JP | 2005148021 | 6/2005 |
| JP | 2005152037 | 6/2005 |
| JP | 2005287691 | 10/2005 |
| JP | 2005304880 | 11/2005 |
| JP | 2005532841 | 11/2005 |
| JP | 2005532849 | 11/2005 |
| JP | 2005343515 | 12/2005 |
| JP | 2006006377 | 1/2006 |
| JP | 2006509574 | 3/2006 |
| JP | 2006177699 | 7/2006 |
| JP | 2006187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007200739 | 8/2007 |
| JP | 2007313340 | 12/2007 |
| JP | 2007330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |
| JP | 2009034345 | 2/2009 |
| JP | 2009050541 | 3/2009 |
| JP | 2009061236 | 3/2009 |
| JP | 2009065726 | 3/2009 |
| JP | 2011015817 | 1/2011 |
| JP | 2011519583 | 7/2011 |
| KR | 20020015907 | 3/2002 |
| KR | 20020061744 | 7/2002 |
| KR | 200600977523 | 7/2006 |
| KR | 100927471 | 11/2009 |
| KR | 20110137001 | 12/2011 |
| KR | 10-2012-099995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | WO200235997 | 5/2002 |
| WO | WO2002045489 | 6/2002 |
| WO | WO2002058330 | 7/2002 |

(56) References Cited

FOREIGN PATENT DOCUMENTS

| | | |
|---|---|---|
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006123346 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | WO2015112603 | 7/2015 |

OTHER PUBLICATIONS

Aronson, J., "Meyer's Side Effects of Cardiovascular Drugs," Elsevier, Mar. 2, 2009, Medical, 840 pages. (Not Attached).

Arshak et al., A Review and Adaptation of Methods of Object Tracking to Telemetry Capsules IC-Med; Jan. 2007 vol. 1, No. 1, Issue 1, 12pp.

"ASGE Technology Status Evaluation Report: wireless capsule endoscopy" American Soc. For Gastrointestinal Endoscopy; Apr. 2006 vol. 63, No. 4; 7 pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; Sep. 2003; Abstract Only.

Barrie, Heidelberg pH capsule gastric analysis. Texbook of Natural Medicine, (1992), Pizzorno, Murray & Barrie.

(56) References Cited

OTHER PUBLICATIONS

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Coury, L. "Conductance Measurement Part 1: Theory"; Current Separations, 18:3 (1999) p. 91-96.
Delvaux et al., "Capsule endoscopy: Technique and indications" Clinical Gastoenterology; Oct. 2008 vol. 22, Issue 5, 1 pp. (Abstract Only).
Description of ePatch Technology Platform for ECG and EMG, located it http://www.madebydelta.com/imported/images/DELTA_Web/documents/ME/ePatch_ECG_EMG.pdf, Dated Sep. 2, 2010.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Evanczuk, S., "PIC MCU software library uses human body for secure communications link" ; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.
Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf.
Ferguson et al., "Dielectric Constant Studies III Aqueous Gelatin Solutions" J. Chem. Phys. 2, 94 (1934) p. 94-98.
Ferguson et al., "Wireless communication with implanted medical devices using the conductive properties of the body," Expert Rev Med Devices, Jul. 2011, 8(4): 427-433.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Greene, "Medicaid Efforts to Incentivize Healthy Behaviours", Center for Health Care Strategies, Inc., Resource Paper, Jul. 2007.
Halthion Medical Technologies "Providing Ambulatory Medical Devices Which Monitor, Measure and Record" webpage. Online website: http://www.halthion.com/; downloaded May 30, 2012; 2 pp.
Herbig, S.M., "Asymmetric-membrane tablet coatings for osmotic drug delivery", Journal of Controlled Release 35 (1995) 127-136.

Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; MICROSENS S.A. pdf document. First in Office Action dated Jun. 13, 2011 for U.S. Appl. No. 12/238,345; 4pp.
Jimbo et al., "Gastric-fluid-utilized micro battery for micro medical devices" The Sixth International Workshop on Micro and Nano-technology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.
Lin et al., "Do Physiological Data Relate to Traditional Usability Indexes?" Proceedings of OZCHI 2005, Canberra, Australia (2005) 10 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-06/04/0004; 2 pp.
McDermott-Wells, P., "What is Bluetooth?", IEEE Potentials, IEEE, New York, NY, vol. 23, No. 5, Dec. 1, 2004, pp. 33-35.
Mckenzie et al., "Validation of a new telemetric core temperature monitor" J. Therm. Biol. (2004) 29(7-8):605-11.
Medtronic, "CareLink Therapy Management Software for Diabetes" Jul. 2010; https://carelink.minimed.com/patient/entry.jsp?bhcp=1; 1 pp.

(56) References Cited

OTHER PUBLICATIONS

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" Aug. 2010 http://www.medtronicdiabetes.com/products/index.html; 2 pp.

Medtronic, "MINI MED Paradigm® Revel™ Insulin Pump" Jul. 2010 http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget; Jul. 2008; http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. 9-21 (1999).

Mini Mitter Co, Inc. 510(k) Premarket Notification for VitalSense. Apr. 22, 2004.

Minimitter Co. Inc. VitalSense Integrated Physiological Monitoring System. Product Description. Jul. 2005.

Minimitter Co. Inc. VitalSense Wireless Vital Signs Monitoring. Temperatures.com Mar. 31, 2009.

Mojaverian et al., "Estimation of gastric residence time of the Heidelberg capsule in humans: effect of varying food composition" Gastroenterology (1985) 89:(2): 392-7.

O'Brien et al., "The Production and Characterization of Chemically Reactive Porous Coatings of Zirconium Via Unbalanced Magnetron Sputtering" Surface and Coatings Technology (1996) 86-87; 200-206.

Owano, N., "Study proposes smart sutures with sensors for wounds" phys.org. Aug. 2012. http://phys.org/news/2012-08-smart-sutures-sensors-wounds.html; 2pp.

"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.

Park, "Medtronic to Buy MiniMed for $3.7 Billion" (2001) HomeCare; http://homecaremag.com/mag/medical_medtronic_buy_minimed/; 2 pp.

Platt, D., "Modulation and Deviation" AE6EO, Foothills Amateur Radio Society; Oct. 26, 2007; 61 pp.

Radio Antennae, http://www.erikdeman.de/html/sail018h.htm; (2008) 5 pages.

"RFID "pill" monitors marchers" RFID News; Jul. 2008 http://www.rfidnews.org/2008/07/23/rfid-pill-monitors-marchers/.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Sammoura, F. et al., "Water-activated disposable and long shelf life microbatteries", Sensors and Actuators A 111 (2004) 79-86.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Sharma, et al., "The Future is Wireless: Advances in Wireless Diagnostic and Therapeutic Technologies in Gastroenterology," Gastroenterology, Elesevier, Philadelphia, PA, vol. 137, No. 2, Aug. 1, 2009, pp. 434-439.

Shawgo, R.S. et al. "BioMEMS from drug delivery", Current Opinion in Solid State and Material Science 6; May 2002, p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).

"Smartlife awarded patent for knitted transducer" Innovation in Textiles News: http://www.innovationintextiles.com/articles/208.php; 2pp. Aug. 2009.

"The SmartPill Wireless Motility Capsule" SMARTPILL, The Measure of GI Health; May 2010 http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal (2010) Apr. 27; http://www.rfidjournal.com/article/view/7560/1, 3pp.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

Trutag, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.

VonStetten, F. et al., "Biofuel cells as power generation for implantable devices", Pore. Eurosensors XX, (2006), pp. 22-225.

Walkey, "MOSFET Structure and Processing"; 97.398* Physical Electronics Lecture 20.

Watson, et al., "Determination of the relationship between the pH and conductivity of gastric juice" Physiol Meas. 17 (1996) pp. 21-27.

Winter, J. et al. "The material properties of gelatin gels"; USA Ballistic Research Laboratories, Mar. 1975, p. 1-157.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Zworkin, "A Radio Pill" Nature, (1957) 898, 179 Nature Publishing Group.

Browne, S.H., et al., "Let visuals tell the story: Medication adherence in patients with type II diabetes captured by a novel ingestion sensor platform," JMIR Mhealth Uhealth; 3(4): e108; 2015; 27 pages.

Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.

Frias, J. et al., "Effectiveness of Digital Medicines to Improve Clinical Outcomes in Patients with Uncontrolled Hypertension and

(56) References Cited

OTHER PUBLICATIONS

Type 2 Diabetes: Prospective, Open-Label, Cluster-Randomized Pilot Clinical Trial," J Med Internet Res, 2017;19(7):e246; p. 15 (16 pages).
Noble et al., "Medication adherence and activity patterns underlying uncontrolled hypertension: Assessment and recommendations by practicing pharmacists using digital health care," JAPHA; 56 (2016) pp. 310-315 (6 pages).
Savage, G., "Predictive Analytics: Advancing Precision and Population Medicine," Harvard Health Policy Review, 2015; vol. 14; Issue 2; 4 pages.
Van der Biest, O., et al., "Electrophoretic deposition of materials," Annu. Rev. Mater. Sci. 1999, 29: pp. 327-352.
Zhang, Y-T. et al., "Wireless Biomedical Sensing," Wiley Encyclopedia of Biomedical Engineering, 2006, pp. 1-9.

\* cited by examiner

STATE CHARACTERIZATION BASED ON MULTI-VARIATE DATA FUSION TECHNIQUES

CROSS-REFERENCE TO RELATED APPLICATIONS

This application is a continuation application claiming priority under 35 U.S.C. § 120 to U.S. patent application Ser. No. 13/844,386, entitled "STATE CHARACTERIZATION BASED ON MULTI-VARIATE DATA FUSION TECHNIQUES", filed Mar. 15, 2013, which is related to U.S. patent application Ser. No. 12/522,249, entitled "INGESTIBLE EVENT MARKER DATA FRAMEWORK", filed Jul. 6, 2009, now U.S. Patent Application Publication No. 2011/0009715, which is a U.S. National Stage Entry under 35 U.S.C. § 371 of International Patent Application No. PCT/US09/49618, filed Jul. 2, 2009, which claims the benefit under 35 U.S.C. § 119(e) of U.S. Provisional Patent Application Ser. No. 61/079,082, filed Jul. 8, 2008, the entire disclosures of which are hereby incorporated by reference herein.

INTRODUCTION

The present invention relates generally to the technical fields of ingestible devices and communications. More specifically, and in various example embodiments, the present invention relates to a method, article, and system of generating, collecting, managing, distributing, and otherwise utilizing information associated with ingestible events and responses to the ingestible events Information related to personal events is widely needed in various pursuits. A personal event is an event that is specific to an individual. Examples of personal events include onset of a physiologic parameter of interest, ingestion of a therapeutic agent, etc.

There are many instances where one may want to note a personal event. Examples of such instances include onset of one or more physiologic parameters of interest including appearance of disease symptoms, administration of medication, ingestion of certain types of foods, commencement of an exercise regimen, ingestion of certain substance, etc.

A variety of different methods and technologies have been developed to note a personal event. For example, techniques have been developed in which individuals can manually record data in a log or physically enter data via a computer device.

The accuracy of such notations may be dependent on the accuracy of data input, the accuracy of proxies used as actual data substitutions, etc. As a result, inaccuracies may occur.

In one example, an individual may suffer from one or multiple health conditions that require therapy with multiple medications. The multiple medications may be prescribed according to an intricate dosing schedule. The complexities associated with multiple health conditions, multiple medication therapies, and intricate dosing schedules may confuse the patient, resulting in inaccurate data capture.

In one example, the individual may have physical or cognitive deficits which may result in difficulties inputting and capturing data. The individual may forget to enter the data, or may enter the data incorrectly.

In one example, the individual may not wish to be inconvenienced and thus may intentionally refuse to enter the data. Conversely, the individual may unintentionally or intentionally enter/record data which is completely inaccurate. For example, the individual may receive periodic, prescheduled reminders to take some medication. The reminders are unable to take into account actual ingestion of the medication. If the individual has already taken the medication, the reminder is both moot and likely to inconvenience the individual. If the medication has not been taken, an inconvenient or unneeded reminder or alert may prompt the user to enter data or send a message advising that the medication has been taken just to quell the alarm while not actually taking the medication. The individual may intentionally leave out portions of the data.

In one example, proxies for data and information may also be inaccurate. For example, "intelligent" medication containers may contain microchips that sense opening of the medication container. From the sensed act of opening the container, an inference may be drawn that medication associated with the medication container has been ingested. The inference may be inaccurate, however, as medication is not necessarily ingested by virtue of opening a medication container.

The above-instances may ripen into further issues if particular parties besides the individual wish to use the individual's personal event data. Examples of users and potential users (sometimes collectively referred to herein as "party" or "parties") of personal event data include family and professional caregivers; communication companies; government agencies, e.g., agencies associated with government provided healthcare coverage; private insurance providers; Food and Drug Administration (FDA); Drug Enforcement Administration (DEA); US Bureau of Alcohol, Tobacco, and Firearms (ATF); care providers; medical device manufacturers; patients; clinicians; pharmaceutical manufacturers; pharmacies; web communities; software providers; marketing and financial analysts; and insurance companies.

Competing interests may exist between an individual's privacy interests in personal event data and the acquisition and appropriation of the personal event data by third parties.

Further, various parties may have a compelling interest in receipt of accurate and comprehensive data, e.g., useful data, either in isolated form (data germane to a particular individual) or empirical form (aggregated data from various sources, various individuals, various personal events of an individual, etc.)

In many circumstances, however, accurate personal event data are not available. The party may have access to faulty data or a crude approximation of the information sought, as discussed above. Thus, the party must rely on such crude proxies to formulate a conclusion. It follows, then, that such conclusions may themselves be skewed or inaccurate. Actions taken in reliance on such conclusions may prove misguided, error-prone, and/or harmful.

To illustrate, a healthcare provider or family member may receive a message from a patient indicating that the patient has taken the medication when, in fact, the patient is merely providing the message without having actually ingested the medication. If the healthcare provider notices changes in the patient's symptoms in close temporal proximity to receipt of the flawed information suggesting medication ingestion, the healthcare provider may mistakenly conclude that the patient's symptoms are a result of the medication ingestion. Based on the mistaken conclusion, the healthcare provider may adjust the medication dosage in an attempt to alleviate the symptoms, perhaps to the patient's detriment.

Of note, the more widely propagated and aggregated the inaccurate data, the more prolific the spread of and reliance on error-associated data and conclusions drawn therefrom.

In addition, recipients of the personal event data may wish to timely receive and utilize such information via a user-friendly, reliable and sophisticated means. The recipients may wish to receive and/or utilize information in discrete areas, integrate the personal event information with other data, and use the personal event information for various purposes.

Examples of various purposes include refining and optimizing data such as patient population data; incentivizing individuals or groups based on personal event data, e.g., ingestible event marker data ("IEM data"); corroborating and advancing decisions; supporting stakeholders' decisions; using IEM data in personalized products and services, e.g., user applications on a mobile telephone; auto refilling prescription medications; managing pharmaceutical life cycle systems and controlled substances; compiling and delivering IP news and information feeds; accessing open sources of anonymized patient population data; determining eligibility and approval for refills, insurance coverage, etc.; using patient tools; participating in social network systems; analyzing aggregated data to derive and/or generate predictive information; supporting and enabling financial transactions; identifying direct and indirect causal failure points in treatment and predict corrective action; and providing dynamic, accurate calendaring/scheduling functions.

Finally, parties may also wish to access personal event data in conjunction with existing systems, e.g., commercial systems such as automated pharmacy systems, banking and financial systems, etc.

As can be seen, methods and systems are needed to seamlessly collect, manage, and distribute personal event data to various parties and systems.

Therefore, there is a need for controlled collection, management, and delivery of accurate personal event data to multi-profile parties for various purposes.

BRIEF SUMMARY OF THE INVENTION

The ingestible event marker data framework provides a uniform, comprehensive framework to enable various functions and utilities related to ingestible event marker data (IEM data). The functions and utilities include data and/or information having an aspect of data derived from, collected by, aggregated by, or otherwise associated with, an ingestion event. In one example, the IEM data are generated via an ingested device. The term "ingested device" includes any device, mechanism, structure, combined structure, or object capable of ingestion by a human subject or a non-human subject.

The IEM data framework is highly scalable and integratable with various existing systems, e.g., systems having computer-related component(s). Specific examples of such systems include pharmacy systems, communication systems, financial and banking systems, school systems, medical systems, government agencies, web communities, and personal computer systems. Such existing systems are herein collectively referred to as "commercial systems".

The IEM data framework enables multiple and various types of implementations. The implementations include various configurations of hardware, software, communication components, and/or data. For example, in one aspect, the IEM data framework is implemented with a basic complement of core components; namely, ingestible event marker data; a hub to receive the ingestible event marker data; and at least one ingestible event marker data system to receive, directly or indirectly, the ingestible event marker data from the hub.

Figure 1:
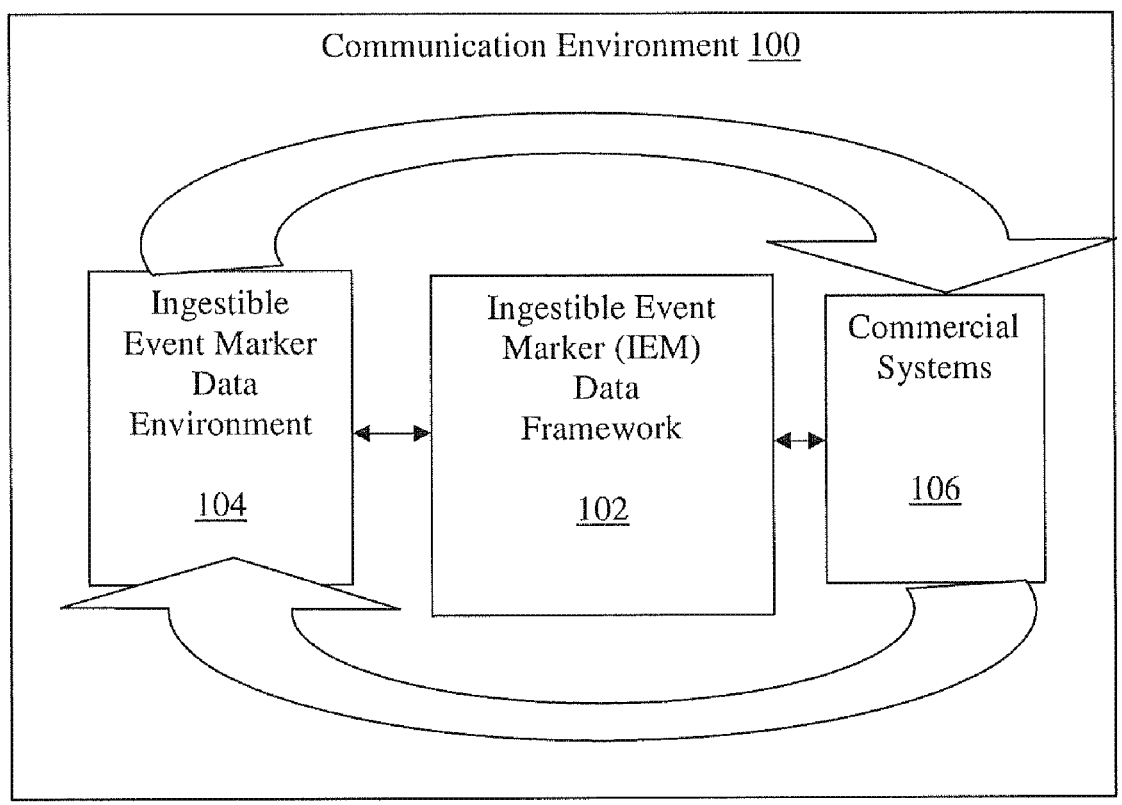
FIG. 1 provides a diagrammatic representation of a communication environment including an IEM data framework, according to one embodiment.

DETAILED DESCRIPTION 1.0 Overview
2.0 Ingestible Event Marker (IEM) Data Framework
   2.1 IEM Data
      2.1.1 IEM Data Environment
         2.1.1.1 IEM Data Source Devices
         2.1.1.2 Products
         2.1.1.3 Events
         2.1.1.4 Patient Specific Parameters
         2.1.1.5 IEM Data Algorithms
         2.1.1.6 Storage Repositories
         2.1.1.7 Other IEM Data Sources
   2.2 Hub
   2.3 IEM Data Systems
      2.3.1 Feedback Loops
      2.3.2 Decision Support Systems
      2.3.3 Auto Refill Systems
      2.3.4 Patient Tools
      2.3.5 Behavioral Medicine Systems
      2.3.6 Incentive Systems
      2.3.7 Personalized Commercial Products/Services
      2.3.8 Auto Billing Systems
      2.3.9 Tracking Systems
      2.3.10 Interdiction Systems
      2.3.11 Subscription Systems
      2.3.12 IEM Data Collection Systems
      2.3.13 Approval Systems
      2.3.14 Forecasting Systems
      2.3.15 Financial Systems
      2.3.16 IEM Data Phone
      2.3.17 Social Network System
3.0 IEM Data Framework Method
4.0 IEM Data Framework Article
5.0 IEM Data Framework System
6.0 IEM Data Framework Data Modeling and Prescriptive Outcomes 1.0 Overview The ingestible event marker (IEM) data framework provides an integrated, seamless solution to enable the collection, management, distribution, and utilization of IEM data. The versatile IEM data framework facilitates integration and implementation of the IEM data with existing data and utilization of the IEM data with existing systems, i.e., commercial systems. The information and communication systems include discrete systems, cross-configured systems, and hybrid systems.

Broadly, various aspects of the IEM data framework include a basic complement of core components, e.g., IEM data; a hub; and at least one IEM data system. Any one or a combination of these core components is capable of interoperation, communication, and/or integration with various components of other information/communication systems. The terms "data" and "information" are used interchangeably herein.

The IEM data include information about an ingestion event, information about a response to the ingestion event, or both. The information about an ingestion event may include, for example, information about the ingestion event of a medication or set of medications. The information about a response to the ingestion event may include, for example, physiologic parameter(s) such as a physiologic status or physiologic change event based on the ingestion event. A physiologic status may be, for example, a heart rate, blood pressure measure, etc., ascertained in close temporal proximity to the time of ingestion of medication (and, therefore, likely to be influenced by or a result of ingestion of the medication.)

Examples of IEM data include data ingestion time(s) of medication, identification of the type(s) of medication ingested at a particular time, the dosage amounts of medication ingested at a particular time, etc.

Typically, the IEM data may be generated and/or communicated via an ingestible device such as an ingestible event marker (IEM), which generates and communicates data associated the ingestion event. The IEM may be associated, for example, with a receiver, i.e., a device capable of receiving the IEM data on ingestion and further capable of measuring additional IEM data on response to the ingestion event(s). The IEM and the receiver are discussed in detail hereinafter. In various aspects, the ingestible event data may originate from multiple ingested event markers. In various aspects, the IEM data may be communicated directly from the IEM to a device other than the receiver, e.g., an IEM business system adapted to receive the IEM data directly from the IEM via a communication channel.

In various aspects, the IEM data may be associated with other data, e.g., combined with data related to events other than an ingestion event or response(s) to an ingestion event. Some examples of other data are data associated with various medical devices and data associated with consumer and personal devices such as intelligent devices/appliances. All are discussed in greater detail hereinafter.

In various aspects, the IEM data may be associated with an IEM data environment and/or commercial systems.

In various aspects, the IEM data may be associated with a unique identifier, e.g., sample data reflective of physiologic patterns associated with a particular individual such as heart rate variability, breathing rate, and/or heart rate (ECG) patterns. For example, a portion or all of the IEM data may be compared with a unique identifier generated by or stored on the receiver.

The hub includes any hardware device, software, and/or communications component(s), as well as systems, subsystems, and combinations of the same which generally function to communicate the IEM data. Communication of the IEM data includes receiving, storing, manipulating, displaying, processing, and/or transmitting the IEM data.

In various aspects, the hub also functions to communicate, e.g., receive and transmit, non-IEM data. Non-IEM data includes non-IEM physiologic data. One example is cardiac data generated by a separate cardiac-related device such as an implanted pacemaker and communicated to the hub directly or indirectly, e.g., via the receiver.

Broad categories of hubs include, for example, base stations, personal communication devices, and mobile telephones.

For example, the hub includes a software application associated with a mobile telephone of a patient. The application and mobile telephone function to receive IEM data from a receiver, which, in turn, receives the IEM data from an ingestible device ingested by the patient. The hub stores, manipulates, and/or forwards the IEM data, alone or in combination with other data, to an IEM data system.

The IEM data systems include any hardware device, software, and/or communications component, as well as systems and subsystems of the same, which generally function to provide a service or activity related to the IEM data. The IEM data systems, for example, collect, manipulate, calculate, transmit, receive, store, and/or communicate at least a portion of the IEM data.

Each IEM data system may be built around predefined function(s) or service(s) and may be enabled via the IEM data framework.

One or more IEM data systems may be integrated, interoperate, intercommunicate or otherwise share or further the collection, management, distribution/dissemination, billing or other activities related to IEM data. One example of an IEM data system is a feedback loop system to refine and optimize IEM data and other data, e.g., medical database data.

Various aspects of the IEM data framework provide on-demand, accurate and efficient services with respect to provision and utilization of IEM data, while reducing redundancies, errors, and inaccuracies associated with personal event data that are sometimes found in the prior art. Various aspects of the IEM data framework further ensure generation and communication of accurate IEM data in a timely manner.

Further, the IEM data framework is applicable to any communication environment. Communication environments include any environment having therein, or associated with, data or communication of data.

Various aspects of the IEM data framework utilize the IEM data, the hub, and one or more IEM data systems to enable useful, secure, and efficient use of the IEM data among multi-profile parties in one or various communication environments.

FIG. 1 provides a diagrammatic representation of communication environment 100 including an IEM data framework 102, according to one embodiment. The communication environment 100 may further include, for example, an IEM data environment 104 and one or more commercial systems 106.

Communication environment 100 includes any environment having therein, or associated with, data or communication of data. Communication includes any method, act, or vehicle of communication, and/or combinations thereof. For example, communication methods include manual, wired, and wireless, etc. Wireless technologies include radio signals, such as x-rays, ultraviolet light, the visible spectrum, infrared, microwaves, and radio waves, etc. Wireless services include voice and messaging, handheld and other Internet-enabled devices, data networking, etc.

Vehicles of communication include the Internet, wired channels, wireless channels, communication devices including telephones, computers, wire, radio, optical or other electromagnetic channels, and combinations thereof, including other devices and/or components capable of/associated with communicating data. For example, the communication environments include in-body communications; various devices; various modes of communications such as wireless communications, wired communications, and combinations of the same, etc.

In-body communications include any communication of data or information via the body, i.e., communication via or associated with inter-body aspects, intra-body aspects, and a combination of the same. For example, inter-body aspects include communications associated with devices designed to attach to a body surface. Intra-body aspects include communications associated with data generated from within the body, e.g., by the body itself or by a device implanted, ingested, or otherwise locatable in, or partially in, the body.

Communications include and/or may be associated with software, hardware, circuitry, various devices, and combinations thereof.

The devices include devices associated with IEM data generation, transmission, reception, communication, etc. The devices further include various implantable, ingestible, insertable, and/or attachable devices associated with the human body or other living organisms. The devices further include multimedia devices such as telephones, stereos, audio players, PDA's, handheld devices, and multimedia players.

Wireless communication modes include any mode of communication between points that utilizes, at least in part, wireless technology including various protocols and combinations of protocols associated with wireless transmission, data, and devices. The points include, for example, wireless devices such as wireless headsets; audio and multimedia devices and equipment, such as audio players and multimedia players; telephones, including mobile telephones and cordless telephones; and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players; telephones, including mobile telephones and cordless telephones; and computers and computer-related devices and components, such as printers.

The IEM data framework 102 enables exchange, transmission, receipt, manipulation, management, storage, and other activities and events related to IEM data. Such activities and events may be contained within the IEM data framework 102, partially integrated with the IEM data framework 102, or associated with externalities, e.g., activities, systems, components, and the like which are external to the IEM data framework 102. Externalities include, for example, the IEM data environment 104 and commercial systems 106, either or both of which may also be integral to, or partially integrated with, the IEM data framework 102.

The IEM data environment 104 includes any source of information or data, including remote computer systems, local computer devices, etc. The information or data may comprise IEM data in whole or in part. The information or data may also be independent of the IEM data, e.g., may be capable of aggregation and/or integration with the IEM data.

The commercial systems 106 include various existing systems that utilize one or various types of data to accomplish a particular purpose. One example of a commercial system is a computerized pharmacy system utilized in a pharmacy. The computerized pharmacy system may function to automatically, e.g., electronically, receive prescriptions, verify patient and prescription information, verify insurance coverage, process the prescription order, and generate an invoice.

The IEM data framework 102, the IEM data environment 104, and the commercial systems 106 are discussed in greater detail hereinafter.

2.0 IEM Data Framework

Figure 2:
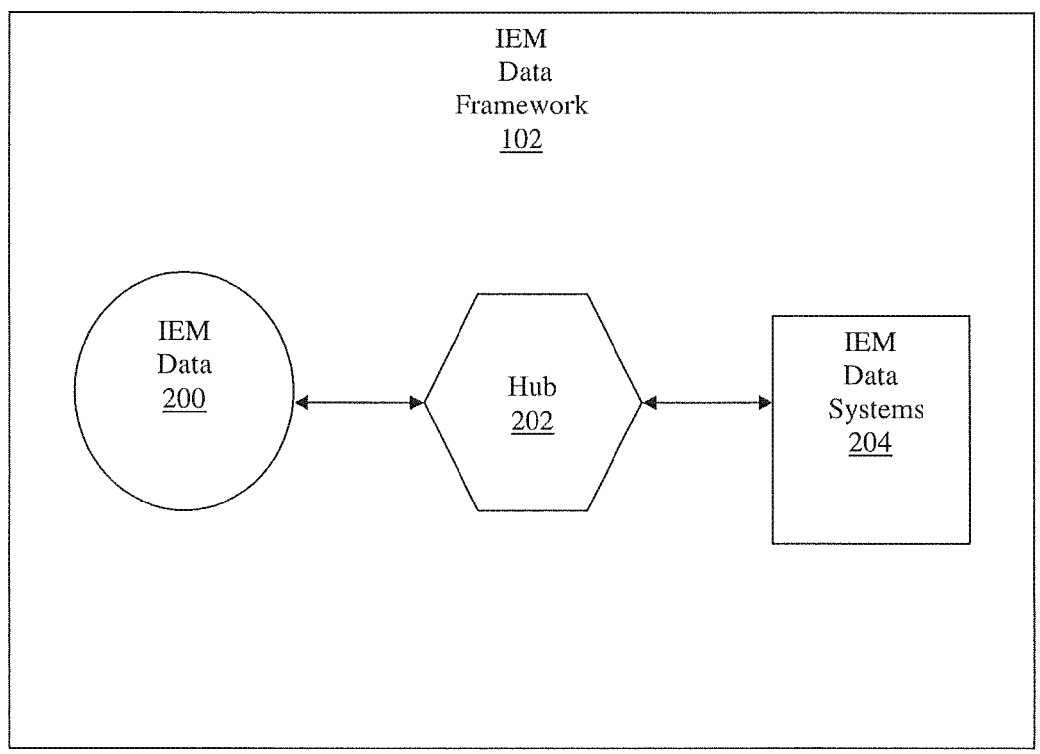
FIG. 2 provides a diagrammatic representation of the IEM data framework of FIG. 1, according to one embodiment.

FIG. 2 provides a diagrammatic representation of the IEM data framework 102 of FIG. 1, according to one embodiment. The IEM data framework 102 includes IEM data 200, hub 202, and one or more IEM data systems 204.

The IEM data 200 include data associated with an ingestion event, i.e., an act of ingestion. Additionally, the IEM data 200 may include, be included in, or be combined with data from other systems or sources, e.g., medical devices, local or remote computer devices and systems, etc. An example of the IEM data 200 is data having an identification of the type of an ingested medication and the time at which the medication was ingested.

The hub 202 includes any hardware, software, and/or communications component(s) in any combination/configuration, which generally function to communicate the IEM data 200. One example includes communicating the IEM data 200 to the IEM data systems 204. For example, the hub 202 receives the IEM data 200 from an ingested device and forwards the IEM data 200, alone or in combination with other data from other sources, to an IEM data system 204.

The IEM data systems 204 provide discrete services and/or activities related to the IEM data 200. The discrete services and/or activities include, for example, propagation of information, data, etc., to a particular user, or group of users, via various system component configurations, etc.

In one example, an auto refill system receives IEM data 200 from the hub 202. The IEM data 200 include an indication that the last remaining pill of a prescription has been ingested. The auto refill system uses this information to contact a local or remote data resource having refill information, verify the refill information, and automatically transmit a request to a pharmacy system (commercial system) for refill of the prescription.

2.1 IEM Data

The ingestible event marker (IEM) data 200 are associated with at least one of an ingestion event and a response to the ingestion event. The ingestion event may be associated with, for example, data related to and/or gathered during transit through the alimentary system, e.g., oral cavity, pharynx, esophagus, stomach, small intestine, large intestine, anus, etc. Examples of IEM data include an ingestion time, identification of ingested substance, expiration date of an associated medication, dosage of an ingested substance, etc. The information about an ingestion event may include, for example, information about the ingestion event of a medication or set of medications. The information about a response to the ingestion event may include, for example, physiologic parameter(s) such as a physiologic status or physiologic change event based on the ingestion event. A physiologic status may be, for example, a heart rate, blood pressure measure, etc., ascertained in close temporal proximity to the time of ingestion.

In various aspects, the IEM data 200 typically may be generated via one or more ingestible event markers (IEMs), discussed hereinafter in detail. The generation of IEM data via multiple IEMs ensures comprehensive data reporting, e.g., data generated from multiple ingestion events of multiple IEMs over a time interval, data generated from multiple IEMs ingested at approximately the same time, etc. In this manner, comprehensive IEM data may be provided.

In various aspects, the IEM data may be communicated to, i.e., received by, a receiver. The receiver may be embodied in various ways, including an implantable device, a semi-implantable device such as a subcutaneous device, and an externally-applied device such as a personal signal receiver. One example of a personal signal receiver is a "patch" receiver which may be removably affixed to the individual's person, apparel, etc.

In various aspects, the IEM data 200 can be associated with other data, e.g., a personal event not associated with an ingestion event or a response to an ingestion event. A personal event includes any parameter or circumstance associated with a person, e.g., any event associated with ingestion, inhalation, injection, implantation, insertion, and/or imbibing of a device, substance, liquid, etc. A personal event further includes any event associated with personal data, e.g., a physiologic parameter such weight.

In various aspects, the IEM data may be associated with a unique identifier, e.g., heart rate variability, breathing rate, and/or heart rate (ECG) patterns associated with a particular individual. The unique identifier may be variously embodied. One example is a personal identifier assigned to an individual, e.g., an alphanumeric code, etc. Another example is a unique identifier reflective of an individual trait, such as a physiologic pattern.

To illustrate, a patient may ingest an IEM (discussed hereinafter) integrated with medication. The IEM may communicate IEM data to a receiver such as a patch receiver (discussed hereinafter). The data may include, for example, a unique identifier which may be compared to data associated with the receiver for validation purposes.

In one scenario, the IEMs associated with medication prescribed for a particular patient may each be encoded and deployed with corresponding unique identifiers. The unique identifier may be, for example, a predetermined physiologic data sample associated the particular patient. Various physiologic data samples include a data sample reflective of the particular patient's heart rate variability, a data sample reflective of the particular patient's breathing rate, a data sample reflective of the particular patients heart rate (ECG) patterns, etc.

When the receiver is affixed or otherwise associated with an individual, programming logic associated with the receiver may receive actual data samples of the individual, e.g., from data sources such as heart devices, etc. The receiver may communicate the actual data samples received from the data sources and the unique identifier(s) received from the IEM(s) to a computer-related device, e.g., a server, which may compare the actual data samples of the individual with the unique identifier to verify that the medication was actually ingested by the particular patient for whom it was prescribed. In various aspects, predetermined actions based on the verification outcome may be taken, e.g., alerts may be sent to a device associated with the prescribing physician, etc.

2.1.1 IEM Data Environment

In various embodiments, IEM data 200 are generated, received, gathered, etc., from one or a variety of sources and comprise various structures, content, types, etc. The IEM data environment includes at least one of an IEM data source device, products, events, patient specific parameters, IEM data algorithms, and storage repositories. The sources include, for example, various devices, storage repositories, and systems capable of generating, identifying, gathering or otherwise producing data related to ingestion, the ingestion environment, e.g., the alimentary system of a human subject or non-human subject and/or other personal events. The types include, for example, raw data, processed data, aggregated data, combined data, data from various sources, etc. The processed data include, for example, data processed according to a variety of methods, e.g., algorithms such as IEM data algorithms discussed below.

Figure 3:
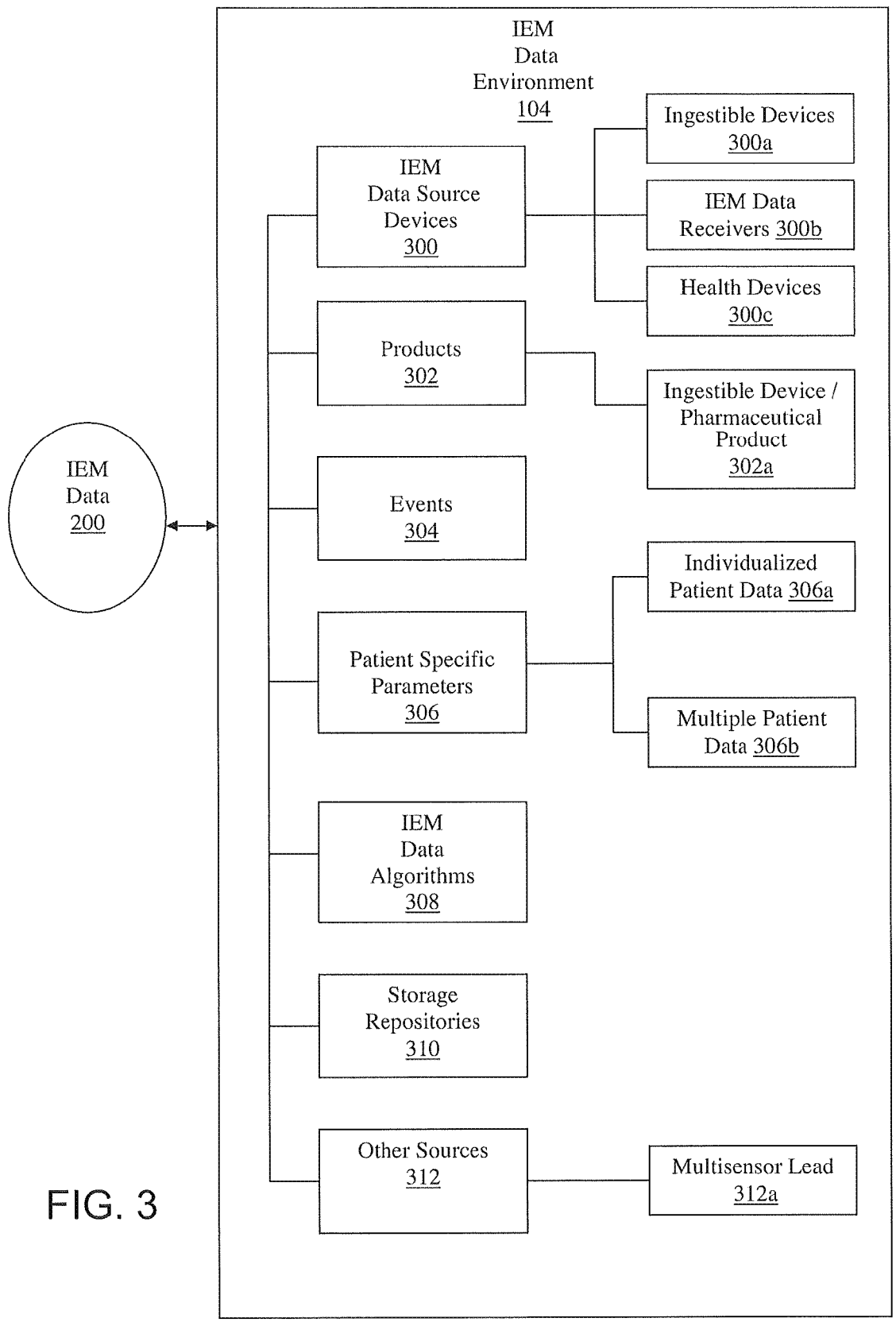
FIG. 3 illustrates IEM data and an IEM data environment associated with the IEM data framework of FIG. 2, according to one embodiment.

FIG. 3 illustrates IEM data environment 104 associated with the IEM data framework 102 of FIG. 2, according to one embodiment. The IEM data environment 104 includes, for example, IEM data source devices 300, products 302, events 304, patient specific parameters 306, IEM data algorithms 308, storage repositories 310, and other sources 312, such as a multisensor lead 312a.

2.1.1.1 IEM Data Source Devices

The ingestible event marker (IEM) data source devices 300 include, for example, devices capable of gathering, collecting, generating, receiving, storing and/or transmitting, etc., IEM data. One example of such a device is a microchip capable of or otherwise enabling or facilitating the collection, generation, receipt, transmission, etc., of data. Such a microchip may be integrated or associated with the IEM data source devices 300. The IEM data source devices 300 may be embodied, for example, as ingestible devices 300a, receivers 300b, and/or health devices 300c.

In various aspects, IEM data may be related to various devices. For example, a device may be an ingestible device, an inhalable device, an injectable device, an implantable device, an insertable device, and an imbibable device. The foregoing may be embodied, for example, as a microchip alone or in combination with other structural components, each capable of at least one of ingestion, inhalation, injection, implantation, insertion, and imbibement by a human body or a non-human body.

The ingestible device may comprise, for example, a microchip. The microchip may be independently deployed. The microchip may also be attached to, embedded in, or otherwise integrated with a medication, e.g., a pill (refer to IEM system, infra).

The inhalable device may comprise, for example, a microchip. The microchip may be independently deployed. The microchip may also be attached to, embedded in, or otherwise integrated with a device. The inhalable device is capable of ascertaining parameter(s) associated with inhalation, e.g., measuring or tallying doses of an inhalant. The inhalable device may also comprise, for example, an inhalable microchip used to ascertain parameter(s), e.g., inhalation time, identify an inhaled substance, etc.

The injectable device may comprise, for example, a microchip. The microchip may be independently deployed. The microchip may also be attached to, embedded in, or otherwise integrated with a device. The injectable device is capable of ascertaining parameter(s) associated with injection, e.g., time of injection, identification of an injected substance, etc. In various aspects, the injectable device is capable of injection into a human body or a non-human body, e.g., injection into the circulatory system of a human body.

The implantable device may comprise, for example, a microchip. The microchip may be independently deployed. The microchip may also be attached to, embedded in, or otherwise integrated with a device. The implantable device is capable of ascertaining parameter(s) associated with implantation, e.g., time of implantation, physiologic parameters such as heart rate, EKG data, activity management data, temperature, galvanic skin response data, respiratory data, fluid status data, heart rate variability, etc.

In one aspect, the implantable device is embodied as an implantable receiver, supra, for receiving various data. The implantable receiver may also process, store, transmit, etc. the data. Various other implantable devices include, for example, heart monitors and the like having a microchip to ascertain parameter(s), e.g., heart rate, heart pressure, etc.

The insertable device may comprise, for example, a microchip. The microchip may be independently deployed. The microchip may also be attached to, embedded in, or otherwise integrated with a device. The insertable device is capable of ascertaining parameter(s) associated with insertion, e.g., time of insertion, physiologic parameters such environmental content/fluid identification, etc. In one aspect, the insertable device is embodied as a microchip mechanically associated with a suppository for rectal insertion, vaginal insertion, etc.

The imbibable device may comprise, for example, a microchip. The microchip may be independently deployed. The microchip may also be attached to, embedded in, or otherwise integrated with a substance, e.g., a potable solution or fluid such as a beverage, etc. The imbibable device is capable of ascertaining parameter(s) associated with imbibing, e.g., time of drinking, physiologic parameters such as environmental content/fluid identification, etc. In one aspect, the imbibable device is embodied as a microchip and imbibed together with a beverage. The beverage may aid in swallowing, may be used as a medication, etc.

Further, the IEM data may be associated with administration of a therapeutic agent, etc. For example, administration includes, but is not limited to, parenteral administration, i.e., administration in a manner other than through the alimentary system, such as by intravenous or intramuscular injection or inhalation.

In some aspects, the devices are capable of ingestion, i.e., entry into the alimentary system of a human body or a non-human; inhalation (either the device or a substance associated with the device, e.g., a nasal inhalant). In various aspects the devices are capable of injection, insertion, implantation and/or imbibing, etc., into/by a human body or a non-human body.

The ingestible devices 300a gather/collect/generate IEM data via various methods, e.g., ingestion timing, contact with alimentary system substances, sampling, etc. Further, various ingestible event marker data source devices 300 communicate the IEM data via various methods, e.g., wireless methods, conductive methods via body tissue, etc. The following are examples of the ingestible devices 300a.

A pharma-informatics system described in PCT/US2006/016370, filed Apr. 28, 2006, includes compositions, systems and methods that allow for the detection of the actual physical delivery of a pharmaceutical agent to a body are provided. Embodiments of the compositions include an identifier and an active agent.

An IEM system described in PCT/US2008/52845, filed Feb. 1, 2008, includes an ingestible event marker (IEM) and a personal signal receiver. Aspects of the IEM include an identifier, which may or may not be present in a physiologically acceptable carrier. The identifier is characterized by being activated upon contact with a target internal physiological site of a body, such as digestive tract internal target site. The personal signal receiver is configured to be associated with a physiological location, e.g., inside of or on the body, and to receive a signal of the IEM. During use, the IEM broadcasts a signal which is received by the personal signal receiver.

The IEM data associated with the IEM system include personal data, e.g., physiologic data generated by the IEM. Examples are derived metrics, e.g., processed physical data to derive various metrics such as time of ingestion data; combined metrics, e.g., derived metrics combined with other derived metric data such as time of ingestion data combined with data identifying the ingested substance; and IEM data, e.g., derived metrics and/or combined metrics aggregated with various physiologic data such as time of ingestion data combined with data identifying the ingested substance and physiologic data such as ECG data, temperature, etc.

A controlled activation ingestible identifier described in PCT/US07/82563, filed Oct. 17, 2007, includes ingestible compositions such as pharma-informatics enabled compositions. The controlled activation ingestible identifiers include a controlled activation element that provides for activation of the identifier in response to the presence of a predetermined stimulus at a target site of interest.

A life cycle pharma informatics system described in U.S. patent application Ser. No. 61/034,085, filed Mar. 5, 2008 includes RFID and conductive communications technology combined with medication and/or medication packaging such that the medication can be tracked for the duration of its existence. The system further allows in-body data transmissions while addressing the potential privacy and signal degradation concerns associated with RFID technology.

The IEM data receivers 300b include devices capable of receipt of IEM data 200. Receipt may be, for example, via wireless or wired channels, etc. The IEM data receiver 300b may also transmit or otherwise forward data. In various aspects, the IEM data receiver 300b may perform, facilitate, or enable various other functionalities related to the IEM data 200 and/or other data. In various aspects, the IEM data receiver 300b may be attachable, implantable, semi-implantable or otherwise associated with a human body or a non-human body.

The IEM data receiver 300b include personal signal receivers such as patch receivers, e.g., removably attachable externally to a human body or a non-human body; subcutaneous devices; implantable devices; external devices, i.e., devices which are not designed for attachment or other permanent or semi-permanent contact with the body, e.g., a mobile telephone. The following are examples of the IEM data receiver 300b.

The IEM system, PCT/US2008/52845, supra, includes an ingestible event marker (IEM) and/or a personal signal receiver.

An active signal processing personal health signal receiver described in PCT/US07/24225, filed Nov. 19, 2007, includes a receiver associated with a body, e.g., located inside or within close proximity to a body, configured to receive and decode a signal from an in vivo transmitter which is located inside the body.

The health devices 300c include multiple devices (and methods associated with the devices) associated with the IEM data 200. The health devices 300c, for example, may gather, collect, aggregate, store, transmit, receive, or otherwise communicate data, including the IEM data 200.

Communication may be, for example, via wireless or wired channels, etc. The IEM data receiver may also transmit or otherwise forward data. In various aspects, the IEM data receiver 300b may perform, facilitate, or enable various other functions related to the IEM data and/or other data. Examples include functions to store data, process data, etc.

In various aspects, the health device 300c may be attachable, implantable, semi-implantable or otherwise associated with a human body or a non-human body. For example, "intelligent" devices such as intelligent scales, intelligent blood pressure cuffs, intelligent refrigerators, etc., may be integrated in various configurations. As used herein, the term "intelligent devices" refers to one or more devices capable of generating and/or communicating data, e.g., wirelessly transmitted data, via a communication channel to a destination.

2.1.1.2 Products

IEM data 200 also includes IEM data related to products 302. The products 302 include, for example, an ingestible device/pharmaceutical product 302a. One example of an ingestible device/pharmaceutical product 302a is an IEM mechanically associated with medication. The IEM may be mechanically associated with the medication in various ways, including externally affixed to the medication, partially integrated with the medication, and wholly integrated with the medication.

The IEM may be affixed via various means, e.g., with various adhesive or formulated substances. The IEM may be associated with the medication at various phases, e.g., during a medication manufacturing process, at various points in time after a medication manufacturing process, etc.

2.1.1.3 Events

IEM data 200 further includes data related to events 304, e.g., personal events, event parameters, etc. Further examples include time of ingestion of a medication, dosage and identity of medication taken at time of ingestion, etc. Events may include physiologic events, e.g., respiration rate; environmental events, e.g., time of day; usage events, e.g., ingestion of a medication, use of a cardiac resuscitation device, etc.

2.1.1.4 Patient Specific Parameters

IEM data 200 still further includes data related to patient specific parameters 306, e.g., individualized patient data 306a pertaining to an individual patient and multiple patient data 306b pertaining to multiple patients. Examples of patient specific parameters include physiologic data, etc. Multiple patient data include aggregated patient data, patient population data, e.g., combined patient data which includes various predetermined aspects of data regarding at least one patient and excludes data tending to identify a particular patient or an aspect in which the patient has a privacy interest, e.g., name, age, diagnosis and/or other data which the patient wishes to retain as confidential and/or undisclosed to the public.

2.1.1.5 IEM Data Algorithms

IEM data 200 also includes data related to IEM data algorithms 308, e.g., raw data, processed data, or a combination of the same, which undergo processing. In one example, the IEM data 200 have one or more algorithms applied thereto, with processed data as an output. The data, for example, includes individualized patient data 306a and multiple patient data 306b, e.g., patient population data.

The IEM data algorithms may be related to aspects such as data processing associated with the IEM data 200 generated by one or more ingestible devices, e.g., an IEM system.

With respect to IEM data processing associated with an ingestible device, aspects include, for example, transmission of the IEM data 200, IEM data processing associated with a receiver, and IEM data post-processing aspects.

Transmission aspects of IEM data and algorithms may include, for example, modulation schemes, coding, and error code aspects.

The transmission aspects include, for example, analog, digital, spread spectrum, combinatorial, and contention avoidance.

The analog transmission aspects include, for example, amplitude modulation, single sideband modulation, frequency modulation, phase modulation, quadrature amplitude modulation, and space modulation methods, etc.

The digital transmission aspects include on/off keying, frequency-shift keying, amplitude-shift keying, phase-shift keying, e.g., binary phase-shift keying, quadrature phase-shift keying, higher order and differential encoded, quadrature amplitude modulation, minimum shift keying, continuous phase modulation, pulse-position modulation, trellis coded modulation, and orthogonal frequency-division multiplexing.

The spread spectrum transmission aspects include, for example, frequency hopping spread-spectrum and direct-sequence spread spectrum.

The combinatorial transmission aspects include, for example, binary phase shift-keying with carrier frequency modulation.

The contention avoidance transmission aspects include, for example, duty-cycle modulation and carrier frequency modulation.

The coding aspects include, for example, wake-up schemes, preamble schemes, data packet schemes, and error code schemes.

The wake-up schemes include, for example, multi-tone schemes and chirp schemes.

The preamble schemes include, for example, unique identifier for packet start schemes.

The data packet schemes include, for example, data related to pill type, pill expiration, manufacturer, lot number, amount, prescribing physician, pharmacy, etc.

The error code schemes include, for example, repetition schemes, parity schemes, checksums, cyclic redundancy checks, hamming distance schemes, and forward error correction schemes, e.g., Reed-Solomon codes, binary Golay codes, convolutional codes, turbo codes, etc.

With respect to IEM data processing and the receiver, considerations may be given to, for example, position, energy conservation schemes, carrier identification, decoding and error correcting.

The position of the receiver includes, for example, the stomach, the side and the xiphoid.

The energy conservation schemes include schemes for a periodic wake-up, e.g., to sense IEM wake-up such that energy, e.g., battery resources, is conserved during non-awake periods.

The carrier identification aspects include, for example, Fourier transform analysis, e.g., fast Fourier transform and discrete Fourier transform, phase locked loop, filter bank, match filter, and combinatorial such as use of previous knowledge about frequency to tune-in.

The decoding aspects and error correcting aspects include, for example, the above-iterated aspects.

With respect to IEM data post-processing, aspects include, for example, pill detection, e.g., multiplicity of identification and count in time aspects, adherence metrics, etc.

With respect to IEM data processing associated with physiologic parameter metrics, aspects include, for example, electrocardiogram (EKG or ECG), impedance, acceleration, optical, pressure, temperature, sound, biochemical/biological, weight, position, derived electromyography (EMG), and electroencephalography (EEG).

IEM data processing related to EKGs includes, for example, compression data, e.g., wavelet and ICA/PCA, R-wave detection such as Hamilton-Tompkins, etc., heart-rate variability, e.g., SDNN, standard deviation in a 24 hour period, standard deviation of consecutive five minute periods, foot print heart rate versus standard heart rate, distribution-based histogram, etc., arrhythmia, and respiration, e.g., principal axis modulation.

IEM data processing related to impedance includes, for example, respiration, fluid status, Galvanic skin response, blood flow, etc.

IEM data processing related to acceleration, includes, for example, direct acceleration, which includes total activity and derived acceleration, which further includes activity type.

IEM data processing related to optical includes, for example, hematocrit, O2 saturation, pulse oximetry, etc.

IEM data processing related to temperature includes, for example, body temperature, heat flux, etc.

IEM data processing related to sound includes, for example, heart sounds, valvular events, etc.

IEM data processing related to biochemical/biological includes, for example, lactose, glucose, antibody, biomarker, bacterial, osmolarity, etc.

IEM data processing related to derived data include, for example, sleep, total energy, etc.

2.1.1.6 Storage Repositories

Ingestible event marker data also includes data related to storage repositories 310, i.e., databases and/or other storage implementations that temporarily and/or permanently retain, store, etc., data related to IEM data, including data to be combined or aggregated with ingestible event marker data.

Storage may be in any form or format, as is known or will be known in the future. In various aspects, the storage repositories 310 may be independently embodied and/or may be partially or wholly integrated with computer-related system(s). The storage repositories 310, for example, may interoperate or otherwise be associated with various computer systems, software, hardware, communication components, etc. For example, the storage repositories 310, may be part of a medical office computer system and may contain IEM data 200 related to a particular's patient's medication regimen. At various times, e.g., scheduled or ad hoc, various IEM data 200 embodied as medical data may be communicated to/from the storage repositories 310 and/or from/to various points/components.

In another illustration, methods, systems and compositions that allow for treating a patient according to a patient customized therapeutic regimen are described in PCT/US2007/1068, filed May 2, 2007, which include obtaining dosage administration information from a patient and using the same to tailor a therapeutic regimen for the patient, as well as preparing and forwarding to the patient physical pharmaceutical dosages based on the customized therapeutic regimen. The dosage administration information from the patient may be stored, for example, on the database 306. The IEM data 200 containing information about the ingestion time of a particular medication can be combined with the dosage administration information to customize the therapeutic regimen.

2.1.1.7 Other IEM Data Sources

In various aspects, various other IEM data sources 312, such as a multisensor lead 312a, are/can be included. Further, it is noted that data and/or IEM data 200 from multiple sources can be aggregated, integrated, refined, etc. via a variety of methods. To illustrate, IEM data 200 such as ingestion data related to ingestion of a medication are generated from an IEM data source device 300 such as the IEM system. The ingestion data are wirelessly transmitted to an IEM receiver.

Concurrently or in an alternative time period, physiologic data such as cardiac parameters are generated by a health device 300c such as the system for monitoring and treating hemodynamic parameters, supra, is generated and wirelessly transmitted to the IEM data receiver 300b. The IEM data 200 and the cardiac physiologic data are aggregated for onward communication to an IEM data system such as an auto refill system.

To illustrate, cardiac data is derived via various methods and systems. One example is continuous field tomography, e.g., electrical tomography (ET). One continuous field tomography method is described in the U.S. patent application Ser. No. 60/797,403, filed May 2, 2006. The cardiac data includes cardiac-related parameters, as well as clinical data for clinical applications. Using ET, various cardiac parameters are measured, such as stroke volume, ejection fraction, dP/dt(max), strain rate(max), peak systolic mitral annular velocity, end systolic volume, end diastolic volume, and QRS length, etc. The cardiac measurements may be used to derive or infer various performance and wellness diagnostics/inferences. For example, an ejection fraction parameter may be used as a basis to predict ventricular synchrony performance.

The metrics generated from the continuous field tomography include, for example, velocity, acceleration, and displacement.

The clinical data derived from the metrics include, for example, left ventricle stiffness as well as ET proxies for other physiologic parameters such as ejection fraction (EF) and dP/dt.

In various aspects, the clinical data may be combined with the IEM data to provide additional information. The information may be useful, for example, in various diagnostic and analytical pursuits. Comprehensive patient-related data displays having clinical data and IEM data are described in the U.S. patent application Ser. No. 61/076,577, filed Jun. 27, 2008, wherein various ET physiologic parameters and derivations such as EF and ventricle stiffness are displayed together with IEM data such as medication ingestion time. From such a display, the efficacy of the medication therapy may be gauged.

2.2 Hub

The hub 202 includes any hardware device, software, and/or communications component(s), as well as systems, subsystems, and combinations of the same which generally function to communicate the IEM data 200, including receiving, storing, manipulating, displaying, processing, and/or transmitting the IEM data 200.

In various aspects, the hub 202 receives, generates, communicates, and/or transmits, the IEM data 200, alone or in combination with other data, i.e., non-IEM data from various sources. Non-IEM data includes non-IEM physiologic data. Examples of non-IEM data include heart rate, heart rate variability, respiration, physical activity level, wake patterns, temperature, etc.

Communication of the IEM data 200 to and from the hub 202 includes any transmission means or carriers, and combinations thereof, including wireless, wired, RF, conductive, etc. as is known in the art or as may become available in the future.

Figure 4:
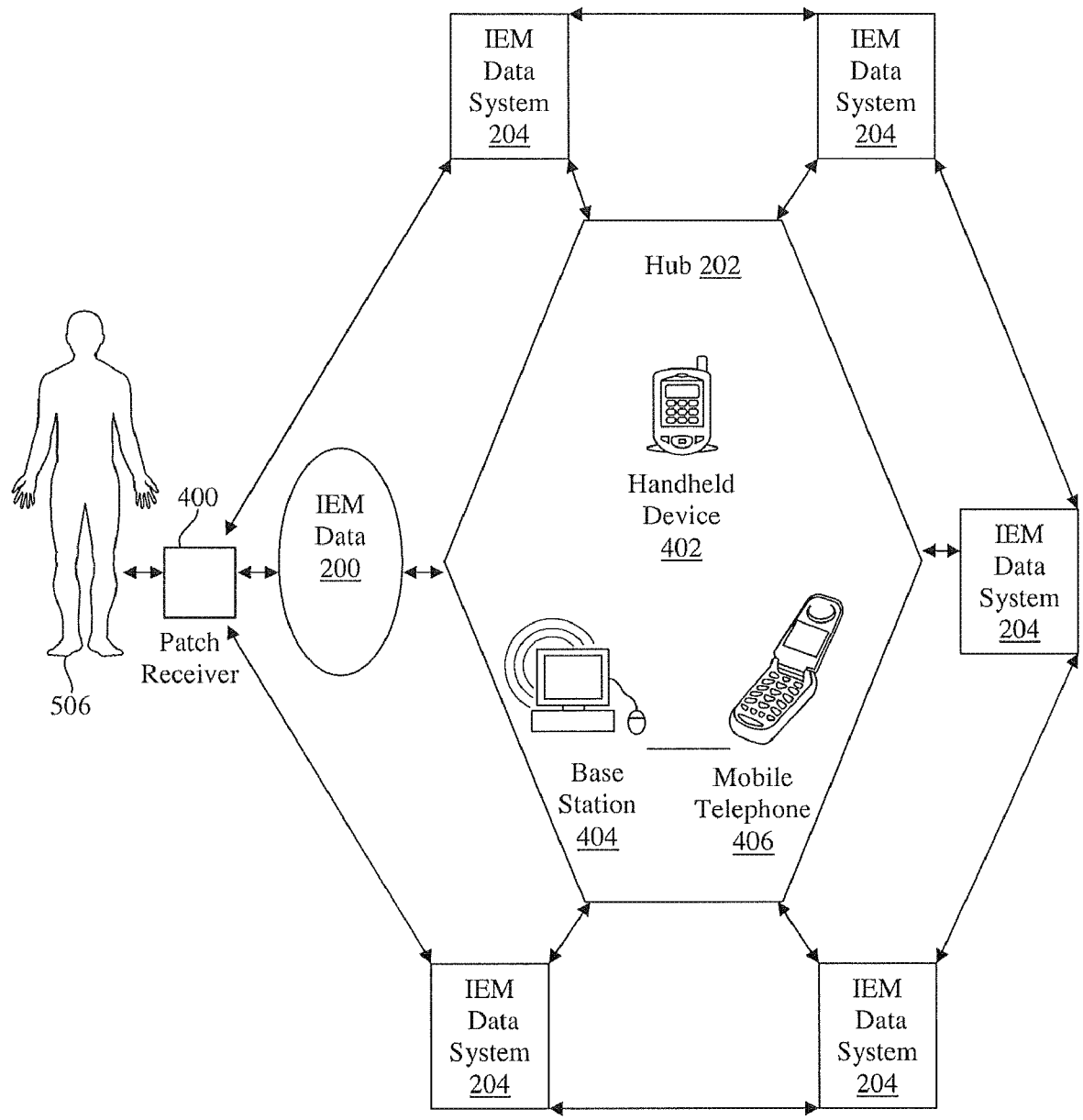
FIG. 4 illustrates a hub associated with the IEM data framework of FIG. 2, according to one embodiment.

FIG. 4 illustrates the hub 202 associated with the IEM data framework 102 of FIG. 2, according to one embodiment. The hub 202 comprises various categories of devices, e.g., personal communication devices, base stations, and mobile telephones.

Personal communication devices include, for example, devices having communication and computer functionality and typically intended for individual use, e.g., mobile computers, sometimes referred to as "handheld devices".

Base stations comprise any device or appliance capable of receiving data such as IEM data. Examples include computers, such as desktop computers and laptop computers, and intelligent devices/appliances.

Intelligent devices/appliances include consumer and home devices and appliances that are capable of receipt of data such as IEM data. Intelligent devices/appliances may also perform other data-related functions, e.g., transmit, display, store, and/or process data. Examples of intelligent devices/appliances include devices and appliances having refrigerators, weight scales, toilets, televisions, door frame activity monitors, bedside monitors, bed scales. Such devices and appliances may include additional functionality such as sensing or monitoring various physiologic parameters, e.g., weight, heart rate, etc.

Mobile telephones include telephonic communication devices associated with various mobile technologies, e.g., cellular networks.

In one aspect, the hub 202 includes an IEM data receiver embodied, for example, as a receiver such as a patch receiver 400; a personal communication devices such as a handheld device 402; a base station 404; and a mobile telephone 406.

The patch receiver 400 includes, for example, devices capable of at least receiving data, signals, etc. Patch receivers 400 may be attachable, e.g., permanently or removably attachable externally to a human body or a non-human body. For example, the patch receiver 400 may include a receiver and an adhesive layer to provide for attachment to and removal from a region of skin. Alternatively, the patch receiver 400 may be implantable or semi-implantable, e.g., subcutaneous implantation. One such removably attachable patch receiver 400 is the personal signal receiver of the IEM system described in PCT/US2008/52845, supra.

The handheld device 402, also referred to as a "mobile computer", includes, for example, computing devices having computer-related functionality, e.g., typically having a display screen with touch input functionality, a miniature keyboard, etc. Types of handheld devices include, for example, a personal digital assistant (PDA) having the input and output combined into a touch-screen interface; and enterprise digital assistants offering integrated data capture devices like bar code, radio frequency identification (RFID), and smart card readers, etc.

In various aspects, the handheld device 402 includes software, e.g., a software agent/application, associated with the IEM data 200. In various embodiments of the handheld device 402, the software is preconfigured, i.e., configurable by the manufacturer/retailer; configurable by the consumer, i.e., downloadable from a website; or a combination of the same.

One example of software is an auto refill application related to or integrated with an auto refill system to facilitate automated prescription refill functions.

The base station 404 includes systems, subsystems, devices, and/or components that receive, transmit, and/or relay the IEM data 200. In various aspects, the base station communicably interoperates with a receiver such as the patch receiver 400 and a communications network such as the Internet. Examples of base stations 404 are computers, e.g., servers, personal computers, desktop computers, laptop computers, intelligent devices/appliances, etc., as heretofore discussed.

In various aspects, the base station 404 may be embodied as an integrated unit or as distributed components, e.g., a desktop computer and a mobile telephone in communication with one another and in communication with a patch receiver and the Internet.

In some aspects, the base station 404 includes the functionality to wirelessly receive and/or wirelessly transmit data, e.g., IEM data 200 received from and transmitted to the patch receiver 400 and the Internet.

Further, in various aspects, the base station 404 may incorporate and/or be associated with, e.g., communicate with, various devices. Such devices may generate, receive, and/or communicate data, e.g., IEM data 200. The devices include, for example, clock radios, intelligent pill dispensers, pill managers, e.g., devices capable of receiving various substances and producing a combined substance, dose(s) of substances, etc., pharmaceutical compounding devices, "intelligent" devices such as scales, blood pressure measurement devices, exercise equipment, e.g., tread mills. Further examples include body weight sensors, motion sensors, position sensors, e.g., bed sensors, chair sensors, portals in doorways, refrigerator and food devices, bathroom facilities devices, etc.

The mobile telephone 406 includes, for example, devices such as a short-range, portable electronic device used for mobile voice or data communication over a network of specialized cell site base stations. The mobile telephone 406 is sometimes known as or referred to as "mobile", "wireless", "cellular phone", "cell phone", or "hand phone (HP)".

In addition to the standard voice function of a telephone, various embodiments of mobile telephones may support many additional services and accessories such as short message service (SMS) for text messaging, email, packet switching for access to the Internet, java gaming, Bluetooth (short range data/voice communications), infrared, camera with video recorder, and MMS for sending and receiving photos and video. Some embodiments of mobile telephones connect to a cellular network of base stations (cell sites), which is, in turn, interconnected to the public switched telephone network (PSTN) or satellite communications in the case of satellite phones. Various embodiments of mobile telephones can connect to the Internet, at least a portion of which can be navigated using the mobile telephones.

In various aspects, the mobile telephone 406 includes software, e.g., a software agent/application, associated with the IEM data 200. One example is an auto refill application related to or integrated with an auto refill system to facilitate automated prescription refill functions. In various embodiments of the mobile telephone 406, the software is preconfigured, i.e., configurable by the manufacturer/retailer; configurable by the consumer, i.e., downloadable from a website; or a combination of the same.

Further, various embodiments of the hub ensure privacy requirements via predetermined methods, e.g., an IEM data source device 300 ingested by an individual transmits sensitive IEM data 200 via body tissues to an IEM data receiver 302 embodied in a patch receiver 400 removably attached to the individual's body. Signals associated with the sensitive IEM data 200 remain undetectable beyond the individual's body. Once received by the patch receiver 400, various computing components of the patch receiver 400 cleanse and/or encrypt the IEM data 200 for onward secure transmission. In this manner, breaches of sensitive data transmissions and/or unauthorized access to the sensitive data are avoided.

Further, various aspects of the hub include combinations of devices. One such combination is an IEM data receiver 300b such as the patch receiver 400 in communication with the handheld device 402 or the mobile telephone 406. Thus, for example, the patch receiver 400 wirelessly transmits IEM data 200 to the mobile telephone 406 having a receiver and a software agent available thereon. The receiver of the mobile telephone 406 receives the IEM data 200. A software agent, e.g., an application, processes the ingested reported data 200 and displays various information related to the IEM data 200 via, for example, a customized graphical user interface (GUI). In some aspects, the software agent generates displays with a predetermined "look and feel", i.e., recognizable to a user as belonging to a predetermined group of software programs, GUIs, source devices, communities, etc.

To illustrate the foregoing, the IEM data 200 may include data about an ingested medication. Once received by the mobile telephone 406, the software agent may compare the data about the medication to a predetermined medication regimen. Upon verification that the proper medication has been ingested at the proper time, the software disables an audible alarm scheduled to alert the individual to take the (already ingested) medication, thus averting an unnecessary reminder and removing the annoyance associated therewith. The software agent, via the GUI, displays a standard message to the individual notifying of the medication ingested and the time of the next dosage.

Additionally, the software agent may include functionality to generate or facilitate a financial transaction. In one example, upon occurrence of a certain event, such as verification that the proper medication has been ingested at the proper time, the software agent generates a predetermined charge for the ingested medication, the verification service, or both. The charge is transmitted to a financial system, e.g., the patient's cell phone transmits the charge via an IEM data system to a computer system associated with the patient's financial institution where the charge is automatically applied against a financial account of the patient.

In various other aspects, the transaction model may be based on various parameters. In one example, a transaction is associated with a time based model wherein use of a product or service is charged according to the length of time the product or service is used. In another example, a transaction is associated with a measured value delivery, wherein the value of the product or service is metered, measured, or otherwise valued and charged according to the ascertained value at predetermined time intervals. In still another example, a transaction is associated with therapy delivery, i.e., delivery of a therapeutic substance, event, service, etc. Examples of therapeutic substances include medication. Examples of therapeutic events include cardiac defibrillation acts and cardiac resynchronization acts. Examples of therapeutic services include administration of therapeutics, therapeutic consultations, etc.

2.3 IEM Data Systems

The IEM data systems 204 include any hardware component, software component, and/or communications component, as well as networks, systems, and subsystems of the same, which generally function to provide a service, function, activity, etc. related to the IEM data 200. The IEM data systems, for example, collect, manipulate, calculate, transmit, receive, store, and/or otherwise communicate at least a portion of the IEM data.

Each IEM data system is built around a predefined business function or service and is enabled via the IEM data framework. One or more IEM data systems may be integrated, interoperate, intercommunicate or otherwise share or further the collection, management, distribution/dissemination, billing and/or other activities related to IEM data.

Further, one or more IEM data systems may be associated with one or more commercial systems. For example, one or more IEM data systems may be integrated with, interoperate with, and/or intercommunicate with one or more commercial systems. One or more IEM data systems may otherwise share or further the IEM data related activities with one or more commercial systems.

The IEM data systems 204 include at least one component, e.g., hardware device, software, and/or communications component, which generally function to provide a service or activity related to the IEM data 200, e.g., a computer to receive IEM data 200 from the hub 202 and display the IEM data 200 in conjunction with other information.

Examples of components include a computer, a receiver, a transmitter, an application, a software module, a data storage medium, a processor, a memory component, a personal communication device, software, a communication link, and a handheld device. It is noted that two or more IEM data systems 204 can cooperatively or independently use one or more of the same components. For example, an auto refill system and an approval system can each access a data storage medium having IEM data related to patients and prescriptions and can each utilize the IEM data for predetermined purpose(s).

Figure 5:
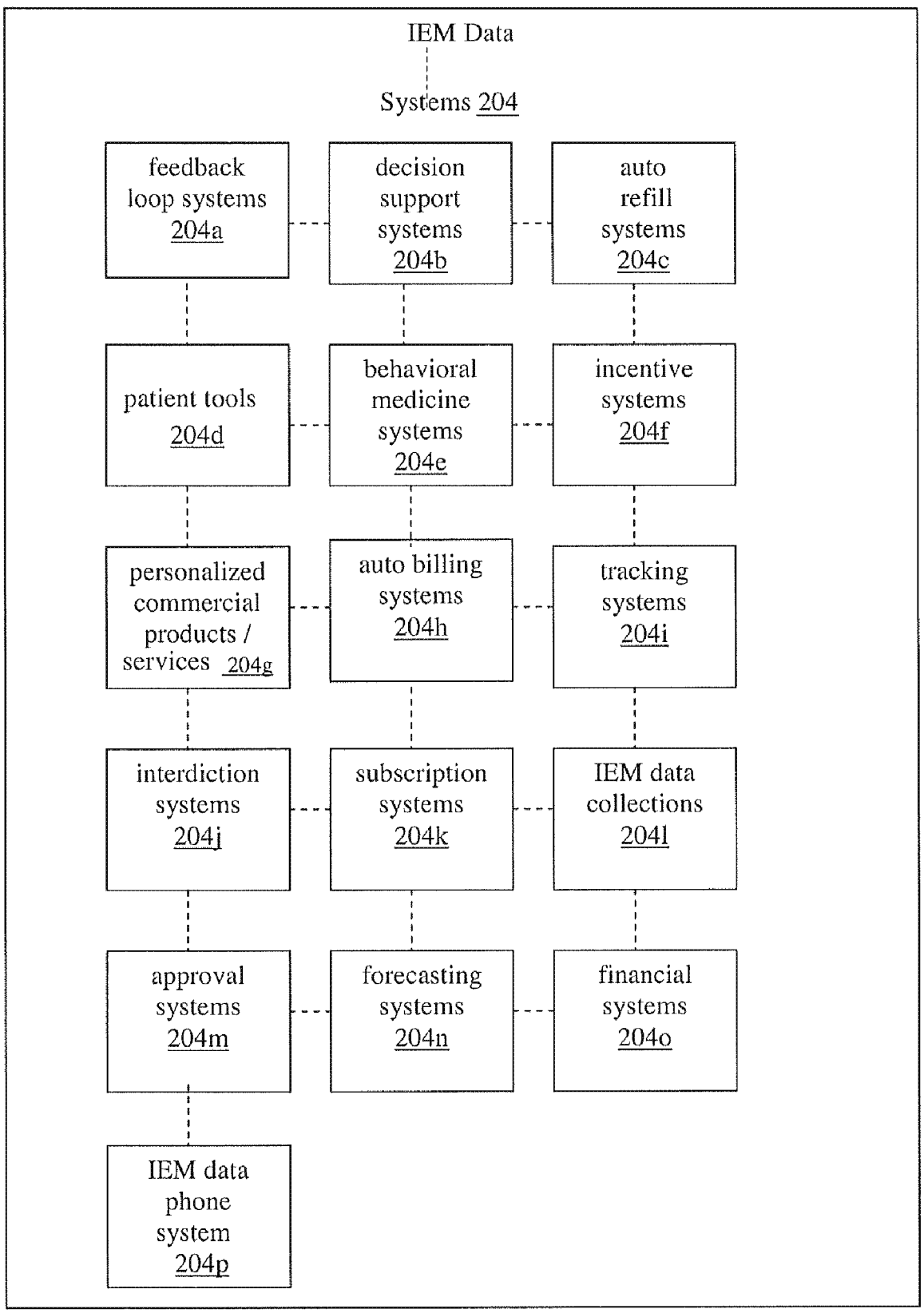
FIG. 5 illustrates exemplary IEM data systems associated with the IEM data framework of FIG. 2, according to one embodiment.

FIG. 5 illustrates exemplary IEM data systems 204 associated with the IEM data framework of FIG. 2, according to one embodiment. The exemplary IEM data systems 204 include, for example, feedback loop systems 204a, decision support systems 204b, auto refill systems 204c, patient tools 204d, behavioral medicine systems 204e, incentive systems 204f, personalized commercial products/services 204g, auto billing systems 204h, tracking systems 204i, interdiction systems 204j, subscription systems 204k, IEM data collections 204l, approval systems 204m, forecasting systems 204n, financial systems 204o, an IEM data phone system 204p, and social networks 204q.

2.3.1 Feedback Loop Systems

Feedback loop systems aggregate various sources of data, e.g., IEM data, analyze the aggregated data, and/or provide feedback information to multiple profile recipients based on the aggregation/analysis.

Figure 6:
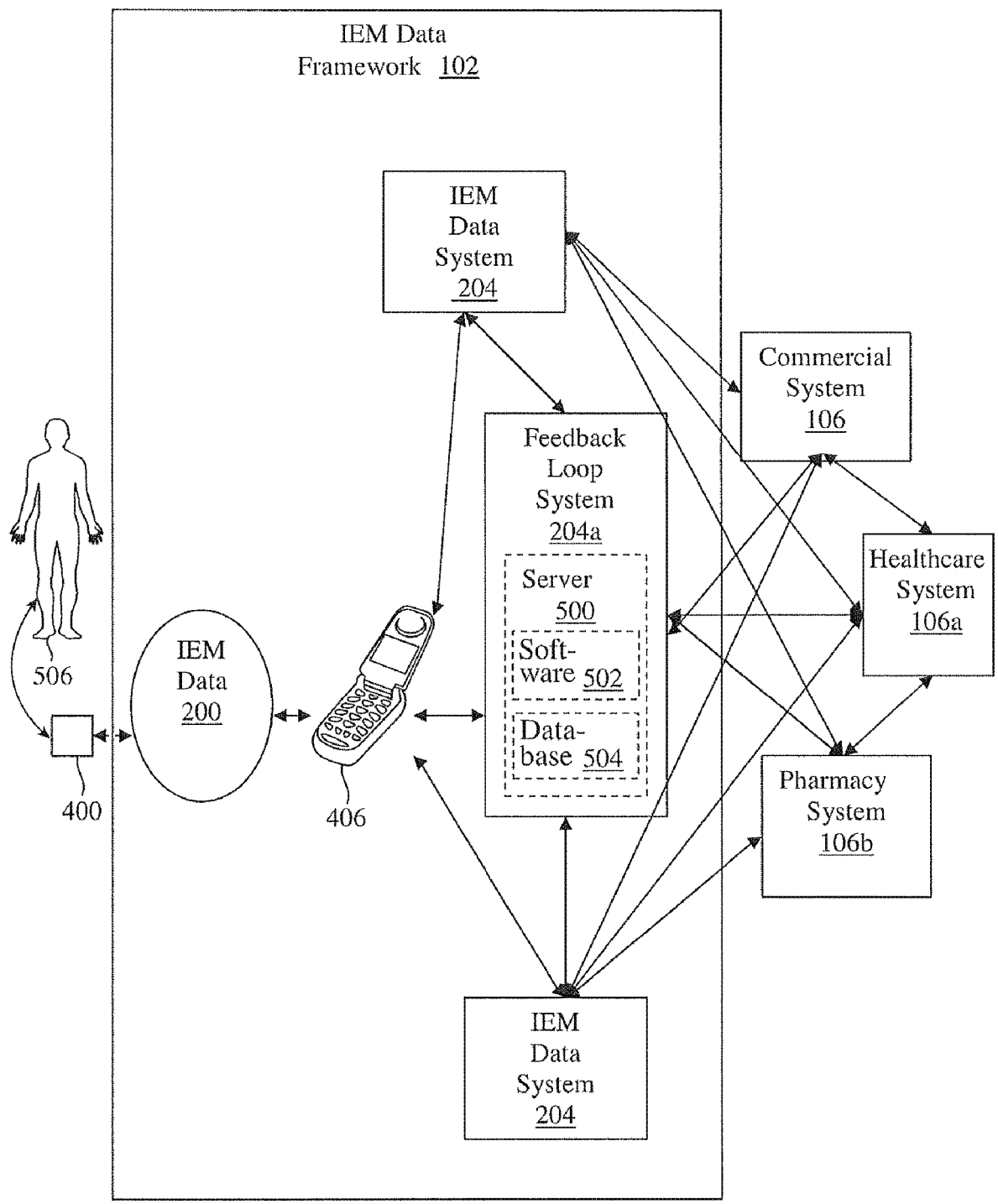
FIG. 6 illustrates an exemplary IEM data framework having a feedback loop system, according to one embodiment.

FIG. 6 illustrates an exemplary IEM data framework 102 including a feedback loop system 204a, according to one embodiment. The feedback loop system 204a includes, for example, server 500 having application 504 and database 504. The IEM data framework 102 further includes IEM data 200 and the hub, embodied here as the mobile telephone 406. In various aspects, the feedback loop system 204a may interoperate, or be otherwise associated with, one or more IEM data systems 204 and/or one or more commercial systems 106.

In one scenario, a patient 506 ingests medication having an ingestible device integrated therein. The ingestible device generates IEM data 200 in the form of medication identification and time of ingestion information. The ingestible device transmits the information to a receiver. The receiver, in turn, communicates the information to the hub 202 embodied as a mobile telephone 406 associated with the patient 506.

A software agent resident on the mobile telephone 406 aggregates the received medication identification and time of ingestion information with the blood pressure measurement information and forwards the aggregated data to the feedback loop system 204a. The feedback loop system 204a, having server 500, software 502, and database 504, receives the aggregated data from the mobile telephone 406 and, via the software 502, compares the aggregated data to patient information in the database 504 to determine if the patient 506 took the most recent dose of medication in a timely manner, if the patient 506 has consistently taken the medication in a timely manner, and if the blood pressure measurement coincides with an acceptable range of blood pressure measurements.

Based on an analysis of the data, the feedback loop system 504a generates additional IEM data 200 in the form of a decision on patient adherence and a decision on treatment efficacy. The IEM data 200 decisions are stored in database 504 for future reference and forwarded to a commercial system such as a healthcare system 106a associated with a medical center computer system and having patient data such as physician's medication instructions, etc.

The healthcare system 106a facilitates automatic processing and feedback, enables accessibility to the IEM data 200, e.g., by a healthcare provider, enables data input, e.g., healthcare instructions by the healthcare provider, etc.

For example, the healthcare system 106a compares the decision data received from the feedback loop system 106a with stored healthcare providers instructions, e.g., medication regimen adherence is satisfactory and no action is needed at this time; medication regimen adherence is not satisfactory and action is needed at this time; medication regimen is satisfactory but action is needed at this time, e.g., titration is needed, etc., and generates the comparison result data for review by the healthcare provider.

The healthcare provider utilizes the information to advantageously adjust patient treatment parameters, e.g., prescription and dosage requirements. The healthcare provider inputs data based on the comparison results, e.g., the adjusted treatment parameters. The input data are processed by the healthcare system 106a and forwarded to the feedback loop system 204a. The feedback loop system 204a receives the feedback loop data, reconciles the feedback loop data with the patient information resident in the database 504, and forwards the notification to the mobile telephone 406 of the patient 506.

In various aspects, the feedback loop system 204a and/or the healthcare system 106a interoperate, e.g., communicate with at least one other IEM data system 204 and/or commercial system 106.

To continue the foregoing illustration, in addition to forwarding the adjusted medication regimen instructions to the patient's mobile telephone 406, either the feedback loop system 204a or the healthcare system 106a forwards the adjusted medication regimen in the form of a prescription to a commercial system such as a pharmacy system 106b for refill. The pharmacy system 106b fills the prescription and communicates a message to the feedback loop system 204a notifying of the same. The feedback loop system 204a updates the patient's data in database 504 to reflect the new prescription and fulfillment of the prescription, and communicates the notification to the patient's mobile telephone 406.

2.3.2 Decision Support Systems

Decision support systems, e.g., personal wellness systems, may generate, store, provide data, e.g., IEM data, which may be used to inform and support decisions, e.g., stakeholders' decisions. In one example, multiple instances of individualized ingestible event marker data and physiologic data are gathered and combined into anonymized patient population data. Pharmaceutical research and development groups, universities, etc., utilize the data for various purposes, e.g., information to formulate new product lines, adjust existing therapies, etc. The data may be accessed, for example, by subscription to population data feeds, access to the database, etc.

Figure 7:
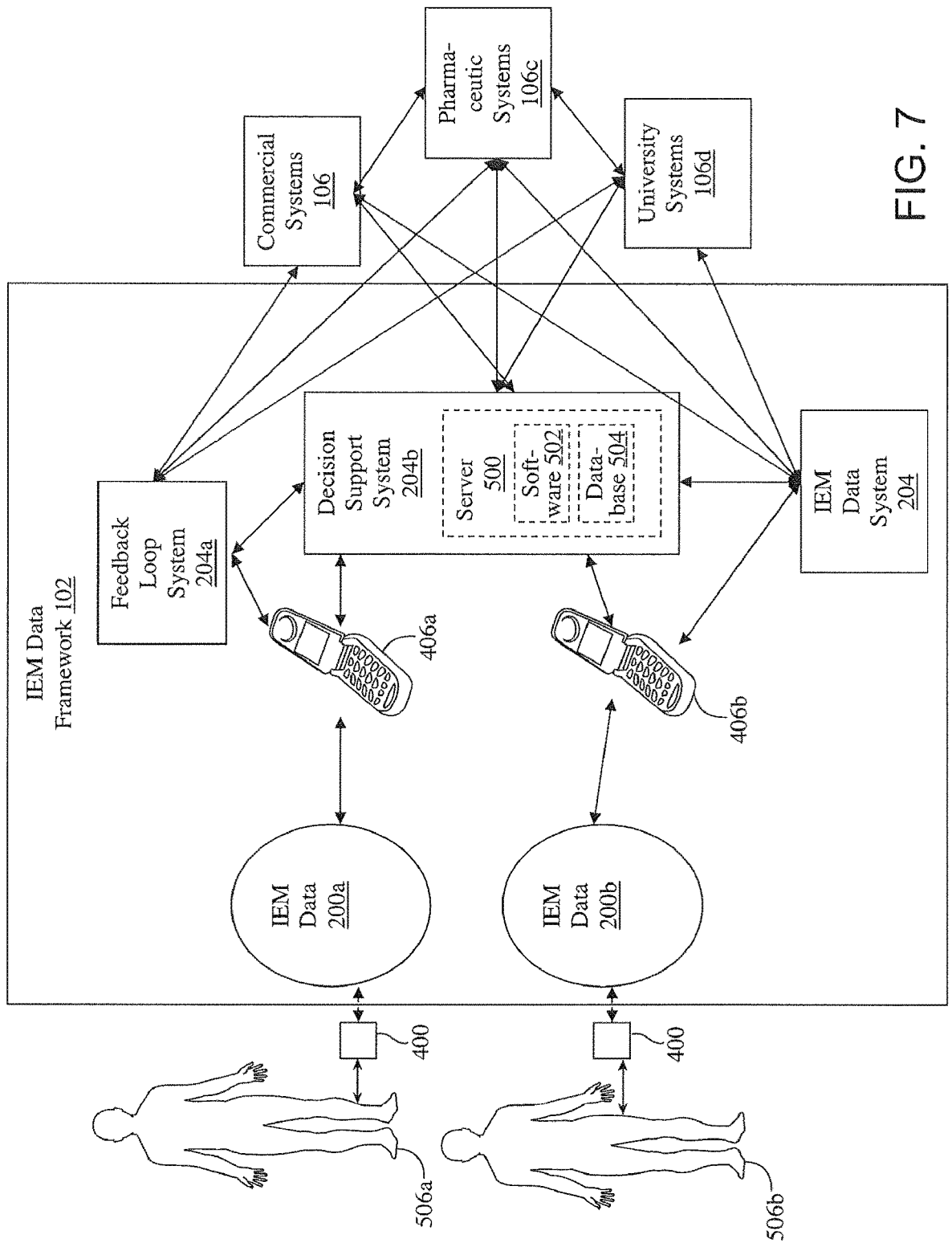
FIG. 7 illustrates an exemplary IEM data framework having a decision support system, according to one embodiment.

FIG. 7 illustrates an exemplary IEM data framework 102 having a decision support system 204b, according to one embodiment. The IEM data framework 102 further includes IEM data 200 and the hub 202, shown here embodied as the mobile telephone 406. In various aspects, the feedback loop system 204a may interoperate, or be otherwise associated with, one or more IEM data systems 204 and/or one or more commercial systems 106.

In one scenario, IEM data, e.g., IEM data 200a and IEM data 200b, related to multiple individuals, e.g., patient 506a and patient 506b, respectively, are communicated via the hubs, e.g., mobile telephone 406a and mobile telephone 406b, respectively, to the decision support system 204b comprising, for example, server 500, software 502, and database 504. The IEM data 200a and 200b may be encrypted. The decision support system 204b processes and stores the received data. For example, software 502 anonymizes the patient data, i.e., removes all aspects of the data tending to identify an individual and removes, according to a predetermined scheme, all aspects of the data designated as private, sensitive, confidential in nature, etc. The software 502 may provide various other functions such as integrating the anonymized patient data with existing patient population data in the database 504.

The integrated data in database 504 may be accessed by, delivered to, or otherwise utilized by multiple systems and parties. Such systems include for example, commercial systems 104 such as pharmaceutic systems 106c and university systems 106d. Parties associated with the pharmaceutic systems 106c may utilize the patient population data, for example, for statistical analysis and projective capabilities such as determining the efficacy, cost efficiency, profit, etc. of a particular medication and projecting from the determination new product line concepts/therapies, etc. Parties associated with universities may utilize the patient population data to research symptomatology, analyze medication risks, etc.

In various aspects, the decision support system 204b, IEM data system(s), and/or commercial system(s) interoperate, e.g., communicate, therebetween.

To continue the foregoing illustration, in addition to the provision of decision support data such as patient population data, the decision support system 204b communicates patient population data to the feedback loop system 204a. The feedback loop system 204a communicates the patient population data to mobile telephone 406a of patient 506a.

In one scenario, the decision data derived from a patient population such as medication efficacy may be correlated with an individual's medication therapy, and communicated via marketing system specifically targeted for that individual.

2.3.3 Auto Refill Systems

Auto refill systems automatically fill or refill prescriptions. In one example, IEM data identifying an ingested medication are gathered and reconciled with current prescription information to identify depleted prescription supplies. If the supply is depleted, a refill order is automatically triggered to the appropriate pharmacy. The pharmacy automatically refills the order, generates a bill, and charges the appropriate account, e.g., via a real time, online financial transaction.

Figure 8:
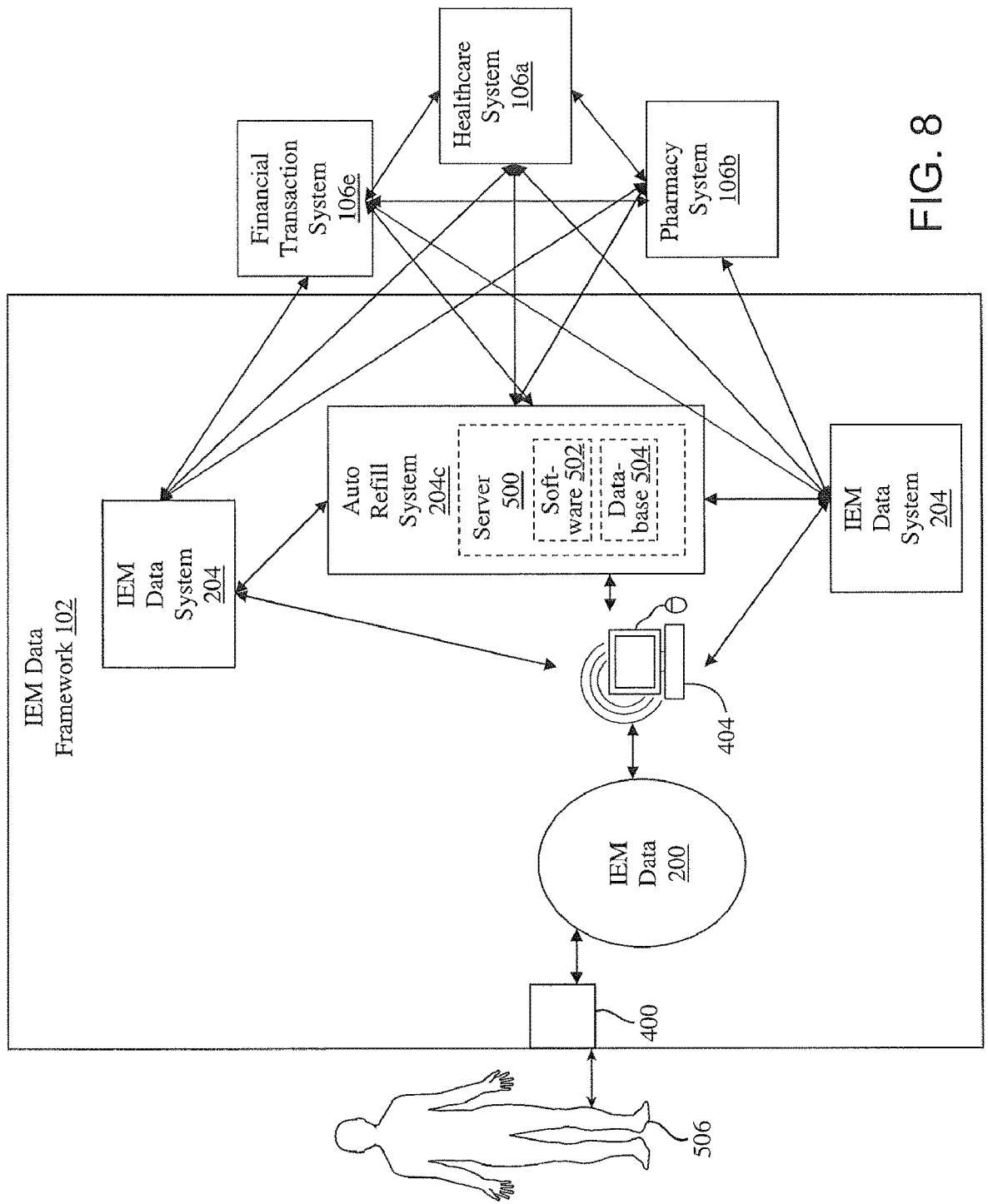
FIG. 8 illustrates an exemplary IEM data framework having auto refill system, according to one embodiment.

FIG. 8 illustrates an exemplary IEM data framework 102 having an auto refill system 204c, according to one embodiment. The IEM data framework 102 further includes IEM data 200 and the hub 202, shown here embodied as the base station 404. In various aspects, the auto refill system 204c may interoperate, or be otherwise associated with, one or more IEM data systems 204 and/or one or more commercial systems 106.

In one scenario, the patient 506 ingests prescription medication in conjunction with an ingestible device. The ingestible device identifies the medication type and dosage, and transmits the IEM data 200 via, for example, conductive transmission to the patch receiver 400, which may be removably attached to the patient 506. The patch receiver 400 transmits the IEM data 200 to base station 404. The base station 400 forwards the IEM data 200 to the auto refill system 204c. The software 502 of the auto refill system 204c compares the medication type and dosage of the IEM data 200 against prescription information stored in the database 504. The prescription information, for example, may include the number of tablets in the prescription at time of fill, the dosage instructions, and a running total of the ingested tablets as per previously received information. If the comparison indicates depletion of the prescription medication, database 504 is checked for the number of remaining refills. If refills are remaining, any sensitive data of the IEM data 200 are cleansed, i.e., removed, and a prescription refill request with pertinent information is compiled and transmitted according to predetermined security protocol and via predetermined channel(s) to a commercial system 106 such as the pharmacy system 106b. Upon receipt by the pharmacy system 106b, the refill request is parsed and verified, and the prescription is refilled.

Payment for refill can be effected, for example, via a real-time, online transaction between the pharmacy system 106b and an IEM data system 204 and/or commercial system, e.g., financial transaction system 106e. The financial transaction system 106e, for example, may receive the financial transaction, e.g., prescription refill charge, via a predetermination communication channel. The financial transaction system 106e verifies the patient account information and completes the transaction, notifying the pharmacy system 106b.

Notification of status of refill and payment for refill can be provided via predetermined communication channel(s) to the base station 300, e.g., an email for display on the laptop computer, a text message to the patient's mobile telephone, etc. 2.3.4 Patient Tools Patient tools include any data, information, software, websites, etc. that provide information or assist a particular patient focus, e.g., tracking tools to assist a patient in cardiac health management, patient personalization of their own data, etc. Various users may be associated with the patient tools. Examples include various users within a patient community, e.g., patients, family caregivers, and professional caregivers such as physicians.

Figure 9:
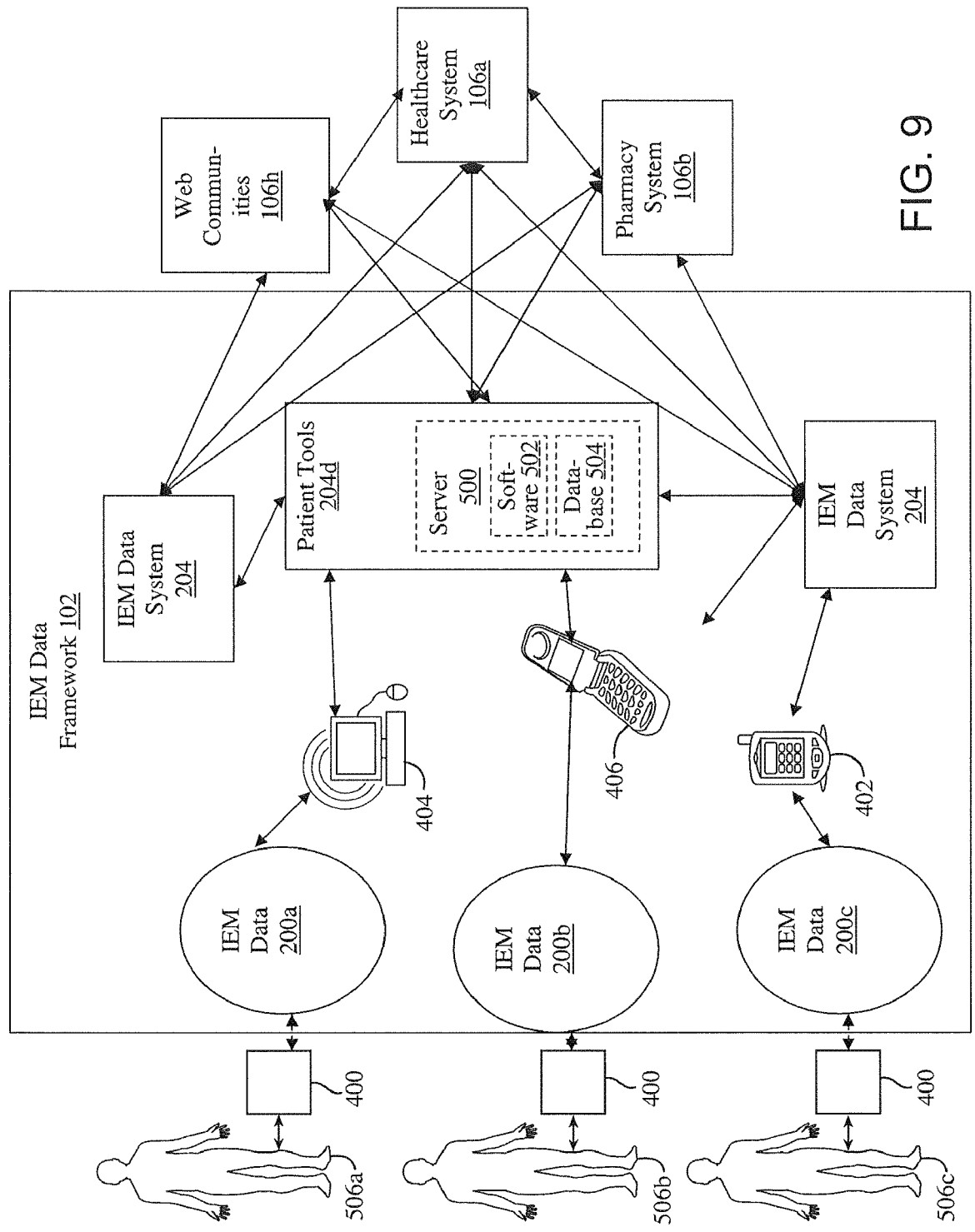
FIG. 9 illustrates an exemplary IEM data framework having patient tools, according to one embodiment.

FIG. 9 illustrates an exemplary IEM data framework 102 having a patient tools 204d, according to one embodiment. The IEM data framework 102 further includes IEM data 200a-c and the hubs, shown here embodied as the base station 404, the mobile telephone 406, and the handheld device 402. In various aspects, the patient tools 204d may interoperate, or be otherwise associated with, one or more IEM data systems 204 and/or one or more commercial systems 106.

In one scenario, multiple parties such as patients 506a-c access the patient tools 204d, which may be embodied as the server 500 having the software 502 and the database 504 having IEM data 200 in the form of at least patient tools. Patients 506a-c may access the patient tools 204d, for example, via the base station 404, the mobile telephone 406, and the handheld device 402, respectively.

Patient 506b may search the database 504 for patient tools related to mental illness management. The patient tools, for example, may be provided in the form of downloadable data/applications to assist in tracking, monitoring, diagnosing, and notifying a patient of a relevant health issue, e.g., medication dosage schedule, etc. Patient 506b may download the application onto, for example, the mobile telephone 406. Patient 506b may further communicate via, for example, the mobile telephone 406 with at least one commercial system such as the healthcare system 106a, which may provide further medical data, instruction, etc., relevant to the patient 506b's mental illness management pursuit.

In various aspects the patient tools 204d may be configured for and utilized by for various parties besides the patient, e.g., a patient community, family caregivers, and professional caregivers.

2.3.5 Behavioral Medicine Systems

Behavioral medicine systems may collect, track, and analyze behavior-related data to identify causal failure points in treatment and to predict corrective action by prescribing specific behavior modifications. In various aspects, the behavioral medicine systems may assist patients via questionnaires and patient profile assessment on symptomatologic or therapeutic subjects, e.g., in various decision processes by display a menu-guided series of questions and receiving answer(s) from the patient.

Figure 10:
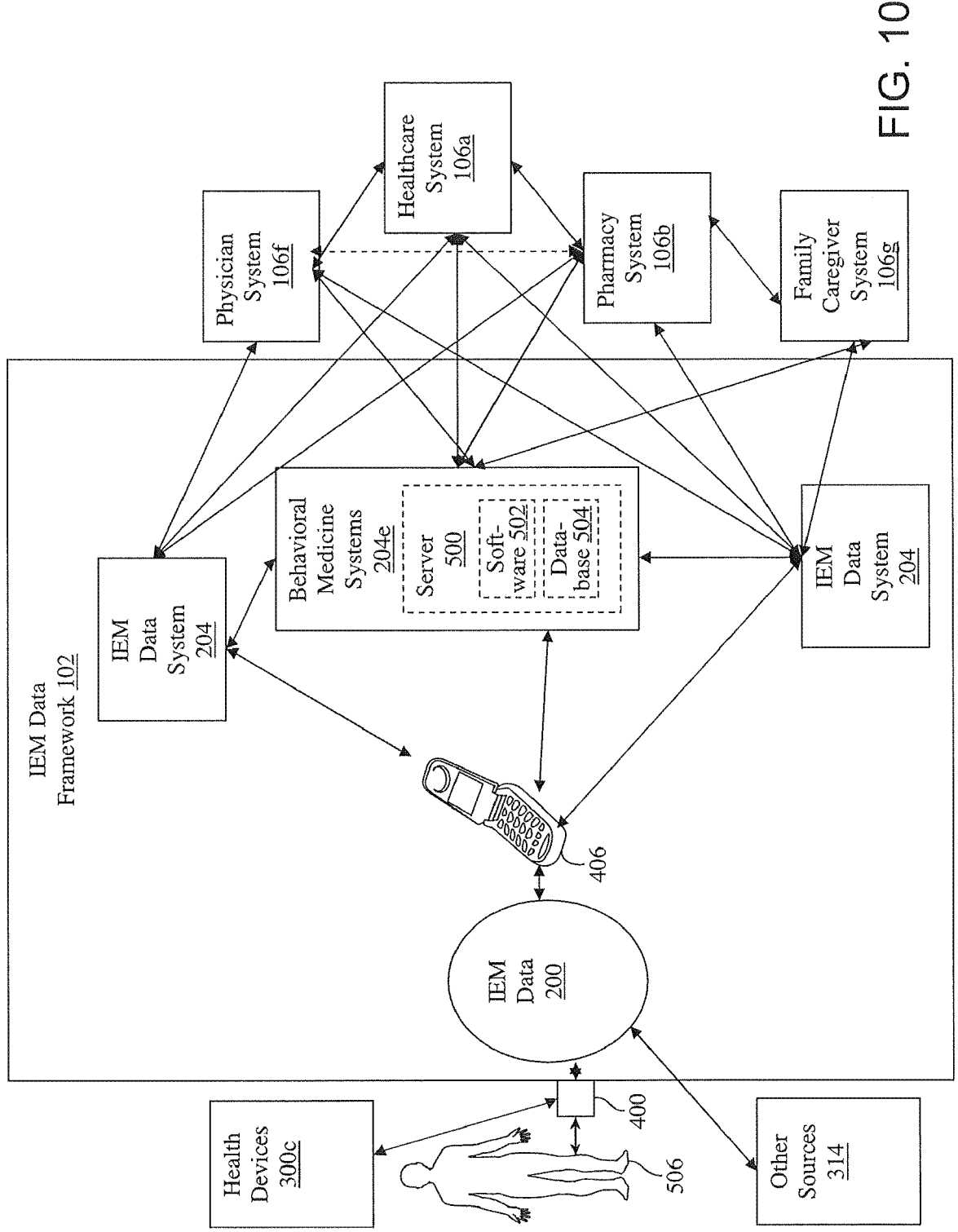
FIG. 10 illustrates an exemplary IEM data framework having a behavioral medicine system, according to one embodiment.

FIG. 10 illustrates an exemplary IEM data framework 102 having a behavioral medicine system 204e, according to one embodiment. The IEM data framework 102 further includes IEM data 200 and the hub, shown here embodied as the base station 404 and the mobile telephone 406. In various aspects, the behavioral medicine system 204e may interoperate, or be otherwise associated with, one or more IEM data systems 204 and/or one or more commercial systems 106.

In one scenario, the behavioral medicine system 204e, e.g., a software agent, may be located in whole or in part on a patient-related device such as the mobile telephone 406. The software agent may assist the patient in various endeavors, e.g., diet choices, smoking cessation, etc. The assistance may be provided, by example, by generating for display on the mobile telephone 406 question sets related to diet and smoking cessation. The patient may answer the questions, e.g., select from various answer options. Based on the patient's answers to the questions, the software agent may categorize the patient according to predetermined categories. The software agent may provide language and menu choices based on the patient categorization.

In another scenario, patient behavior is tracked with respect to various IEM data, e.g., patient parameters, sometimes referred to herein as "sentinels for wellness". Examples of sentinels for wellness include medication therapy adherence, weight, blood pressure, etc. The sentinels for wellness may be derived, for example, from various health devices 300c such as intelligent scales, cardiac-related devices, etc.

To illustrate, patient 506 ingests medication according to physician instructions. The IEM data 200 in the form of ingestion information identifying the ingested medication and the time of ingestion are captured via an ingestion device and communicated to the patient's mobile telephone 406. Also captured via health device(s) 300c at the time of medication ingestion are the patient's blood pressure and weight. The timing of the foregoing data captures may be synchronized via, for example, software utilizing a reminder system to alert the patient to take the medication at a particular time. Upon receiving the ingestion information, e.g., confirmation of ingestion, the software associated with the mobile telephone 406 communicably triggers health device(s) 300c to determine blood pressure and weight, and forwards such data to the mobile telephone 406 for aggregation with the IEM data 200 in the form of the ingestion information.

The aggregated data may be forwarded to behavioral medicine system 204e, which may be configured, for example, as the mobile telephone and software 406, the server 500 including the software 502 and the database 504, and/or other configurations. Upon receipt of the aggregated data, various processing may take place.

One example of processing is analysis of the IEM data 200 to determine degree of patient adherence to medication regimen, i.e., determine if the patient ingested the prescribed medication in the right dosage at the prescribed time interval(s).

Another example of processing is analysis of the IEM data 200 to determine if the blood pressure measurement is in line with physician expectations. Thus, the notification of patient adherence to the medication regimen and the blood pressure measurement may be communicated to a physician system 106f for review by the patient's physician. The physician, in turn, may update the IEM data 200, e.g., determine an adjustment in the medication regimen is needed and communicate, via the behavioral medicine system, the updated medication regimen to the patient's mobile telephone 406 and to the pharmacy system 106b for filling the updated prescription.

In cases of a nonadherence determination, the physician may alert the patient, via the behavioral medicine system 204e, to make an appointment for a physical review. In various aspects, the behavioral medicine system 204e may generate and/or forward a reminder to the hub, e.g., mobile telephone 406 of the patient 506. The reminder, for example, may include the dosing schedule, a reminder for the upcoming dose, instructions to follow in case of a missed dose, etc.

In cases of underdosage/overdosage, the behavioral medicine system 204e may interoperate with an alert system, e.g., the IEM data phone system, infra, and compare current dosage information to predetermined thresholds to determine if a critical status dosing event exists, e.g., the patient is critically underdosed or critically overdosed. If such a determination is made, the appropriate system may generate an alert to appropriate parties, e.g., generate a 911 emergency call for medical assistance, generate an emergency alert to the physician system 106f, and generate an alert to a family caregiver system 106g, e.g., a family member's mobile telephone.

In still another scenario, analysis of the patient's communication patterns/habits is performed to determine patient parameters, indicated actions, etc. To illustrate, an application such as software 502 resident on the mobile telephone 406 tracks the patient's phone usage to determine communication patterns. For example, the family caregivers, physician, etc., may selectively configure tracking parameters of the application to determine various patient communication thresholds, patterns, etc. The software monitors communication from/to the selected device, e.g., the patient's mobile telephone 406. In various aspects, the application mines mobile telephone records of the associated carrier to determine calling and called parties, heavy volume call time, no call times, etc. and builds a profile against the same. The application monitors use of the mobile telephone 406 and identifies significant, e.g., user selected, deviations from the profile. Upon identification of a deviation, the application initiates predetermined actions, e.g., communicates an alert to the physician and/or family caregiver via the healthcare system 106a, the physician system 106f, and/or the family caregiver system 106g.

Another example of processing is analysis of the IEM data 200 together with data from another source 314, e.g., aggregated data. The aggregated data may be collected from various sources, aggregated at various and/or multiple points, and/or communicated via various channels to/from various devices.

To illustrate, cardiac data is derived via electrical tomography, as heretofore discussed. The cardiac data is communicated directly or indirectly, e.g., by the patch receiver 400, to a software application on the hub, e.g., the mobile telephone 406. The software application on the mobile telephone 406 aggregates the cardiac data with the IEM data, e.g., pill ingestion-related data, and displays the various data via a graphical user interface (GUI).

Subsequent to enrollment, the behavioral medicine system ascertains that the patient has neglected to take the medication at the appropriate times. Reminder alerts for upcoming medication dosing time(s) are sent to the patient via the mobile telephone. Upon receiving the alerts, the patient timely ingests the medication, resulting in a change in the sentinels for wellness.

2.3.6 Incentive Systems

Incentive systems provide incentives and rebates through various programs. The incentives and rebates are based on, or otherwise associated with, the IEM data. The IEM data may be analyzed via, for example, an IEM data system 204 to determine if certain criteria/thresholds/goals are evident. Based on the determination, incentives tied to or associated with the criteria/threshold/goals may be generated.

Figure 11:
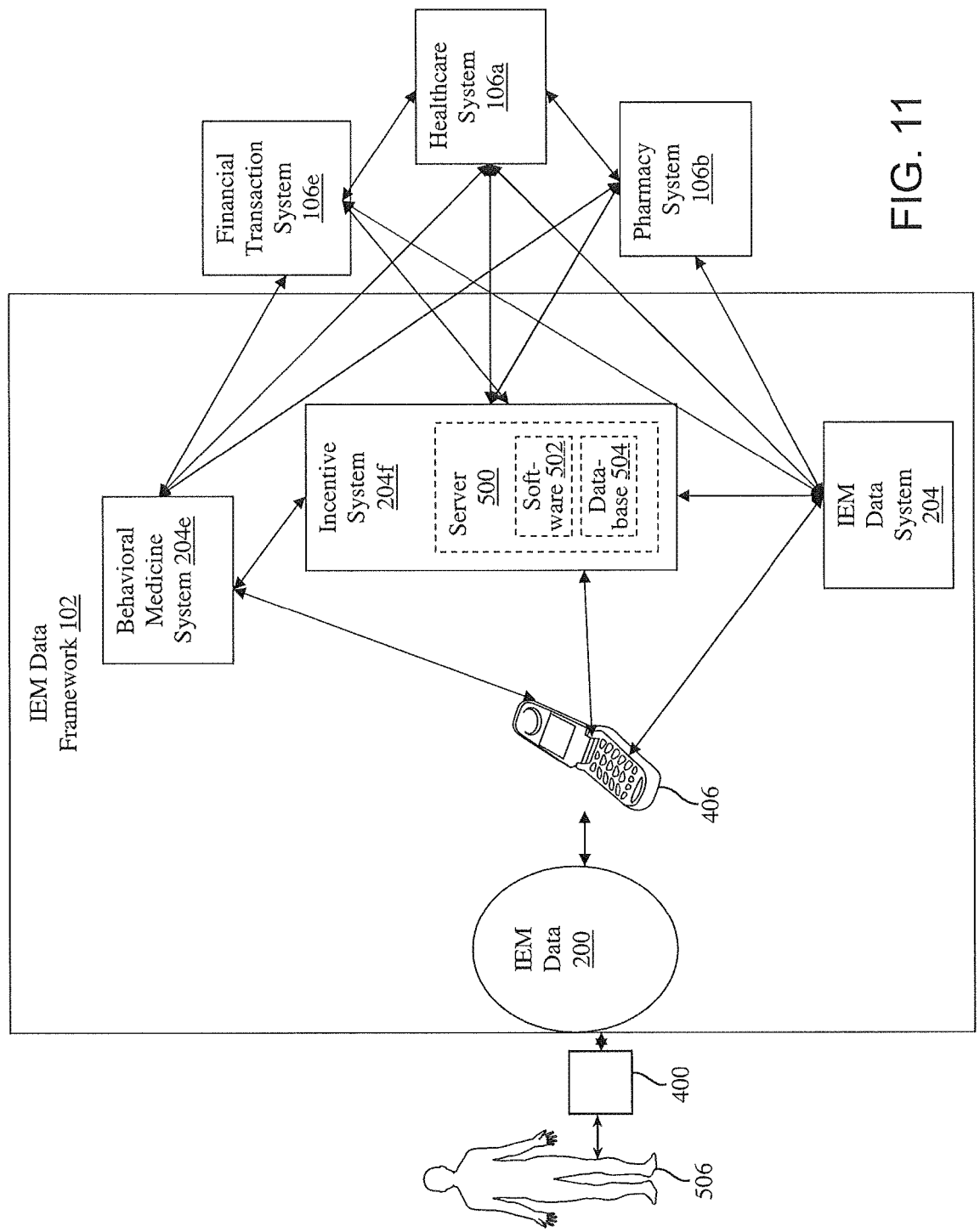
FIG. 11 illustrates an exemplary IEM data framework having an incentive system, according to one embodiment.

FIG. 11 illustrates an exemplary IEM data framework 102 having an incentive system 204f, according to one embodiment. The IEM data framework 102 further includes IEM data 200 and the hub, shown here embodied as the mobile telephone 406. In various aspects, the incentive system 204f may interoperate, or be otherwise associated with, one or more IEM data systems 204 and/or one or more commercial systems 106.

In one scenario, patient adherence is tracked with respect to various patient parameters, e.g., medication therapy and adherence. Incentives may be awarded accordingly. For example, patient 506 ingests medication according to physician instructions. The IEM data 200 in the form of ingestion information identifying the ingested medication and the time of ingestion are captured via an ingestion device and communicated to the patient's mobile telephone 406, and to the behavioral medicine system 204e. The behavioral medicine system 204e verifies patient 506 adherence to the prescribed medication regimen, and sends verification to the incentive system 204f. The incentive system 204f, via the software 502 and the database 504, determines the price paid for the medication, and issues a rebate or credit against the cost. For example, the rebate may be issued and a financial transaction in the amount of the rebate posted to the patient's financial account via the financial transaction system 106e.

In another example, the rebate may be communicated and applied to an account associated with the patient via the pharmacy system 106b with, for example, a credit against the next refill for the patient's prescription medication.

In another example, the patient's blood pressure and weight may be captured via health device(s) 300c at time of medication ingestion. The timing of the foregoing data captures may be synchronized via software utilizing a reminder system to alert the patient to take the medication at a particular time. Upon receiving the ingestion information, e.g., confirmation of ingestion, the software associated with the mobile telephone 406 may communicably trigger health device(s) 300c to determine blood pressure and weight, and forward such data to the mobile telephone 406 for aggregation with the IEM data 200 in the form of the ingestion information. The aggregated data may be communicated to the incentive system 204f where the software 502 and/or database 504 may be utilized to determine if the patient's weight and blood pressure meet acceptable predetermined thresholds. If, for example, the weight exceeds an acceptable threshold, the incentive system 204f may generate an incentive in the form of a discount membership offering at a local health club, etc. The offering may be constructed using various data parameters and demographics, e.g., geographical location of the patient, amount of weight to be lost, health assessment scoring based on individualized patient health parameters, lists of participating health clubs, etc.

The incentive may be communicated to the patient 506 via, for example, the patient's mobile telephone 506.

2.3.7 Personalized Commercial Products/Services

Personalized commercial products/services provide individualized products and services predicated on or related to IEM data.

Figure 12:
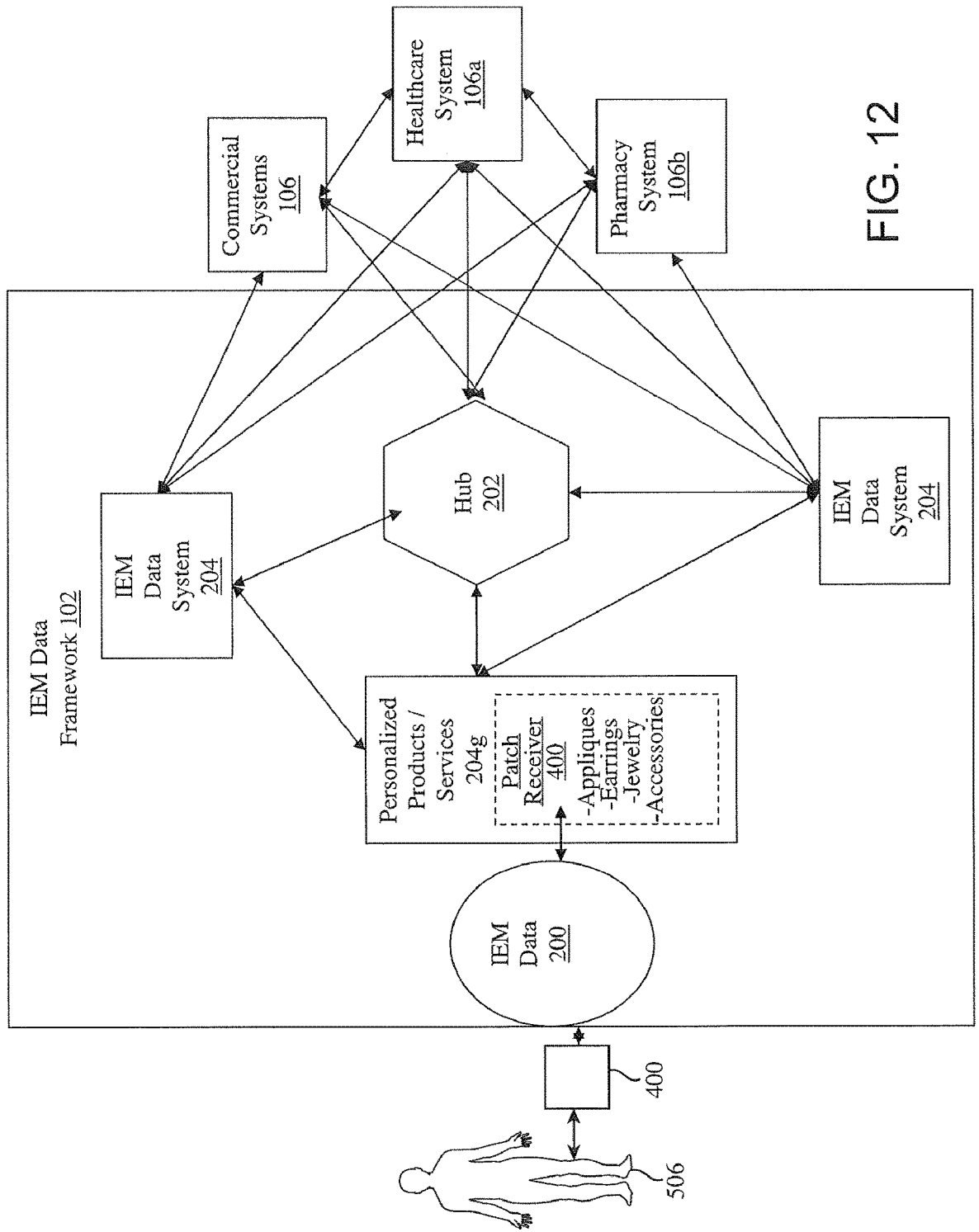
FIG. 12 illustrates an exemplary IEM data framework having a personalized commercial products/services system, according to one embodiment.

FIG. 12 illustrates an exemplary IEM data framework 102 having a personalized commercial products/services system 204g, according to one embodiment. The IEM data framework 102 further includes IEM data 200 and the hub 202. In various aspects, the commercial products/services system 204g may be embodied as, for example, an IEM data device, e.g., a patch receiver. In various aspects, the commercial products/services system 204g may interoperate, or be otherwise associated with, one or more IEM data systems 204 and/or one or more commercial systems 106.

In one scenario, commercial products/services system 204g include consumer-friendly receivers, such as patch receivers. The receivers comprise various accessories and incorporate various designs. For example, children's patch receivers may comprise cartoon character appliqués. Youths' patch receivers may comprise tattoo-like design aspects. Further examples include IEM data receivers embodied as/integrated into accessories, e.g., earrings, naval rings, and other means of adornment, etc.

Commercial products/services system 204g further comprise branded or "community" associated products and services.

2.3.8 Auto Billing Systems

Auto billing systems receive, process, and/or facilitate payment via a financial account. Auto billing applications associated with the auto billing system and/or with financial institution systems seamlessly interoperate to generate a bill, verify accountholder information, charge an account, etc. Statements are updated to reflect payment information. Similar applications may be applied for prescriptions, consumer products, information provision via personal devices, etc.

Figure 13:
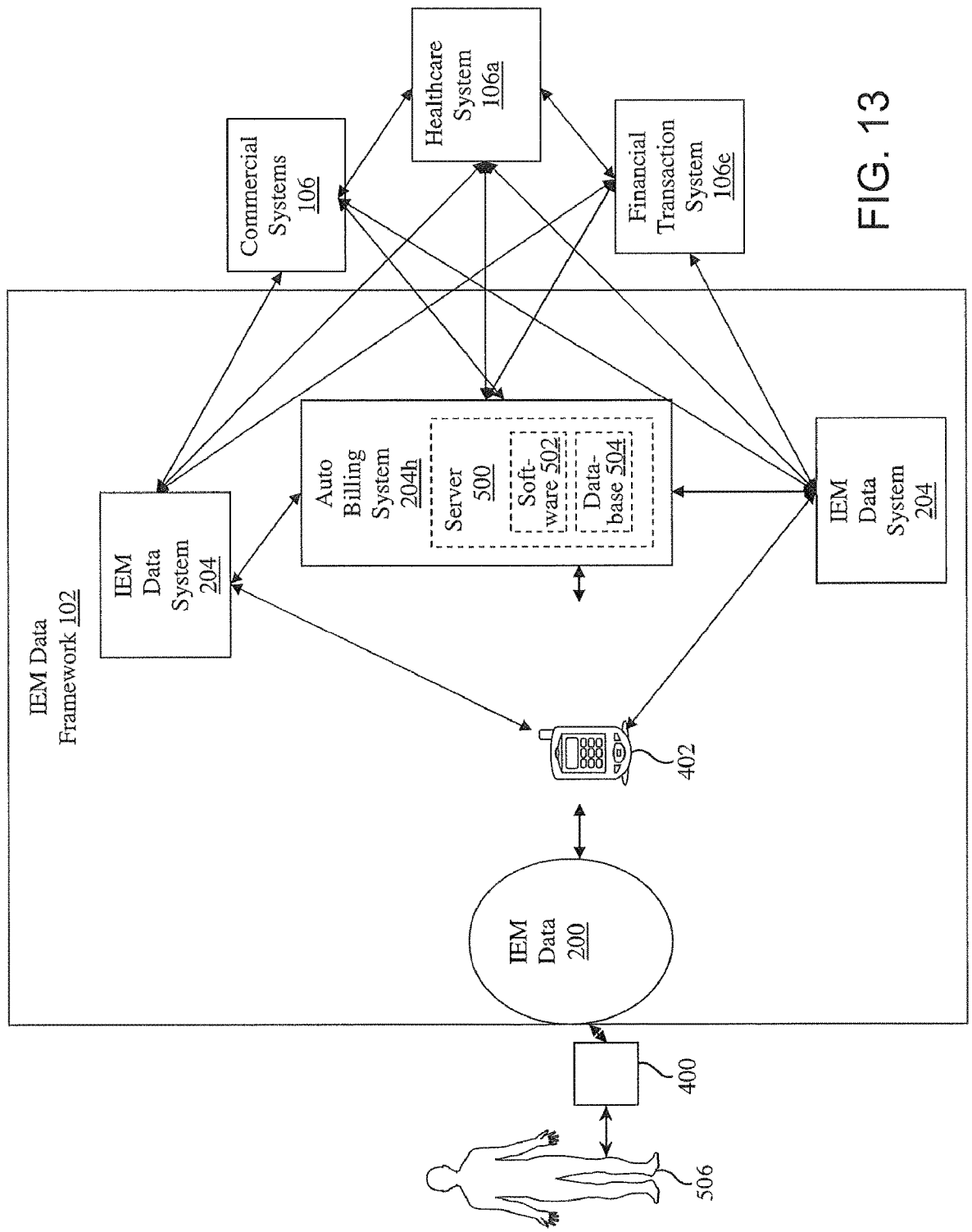
FIG. 13 illustrates an exemplary IEM data framework having an auto billing system, according to one embodiment.

FIG. 13 illustrates an exemplary IEM data framework 102 having an auto billing system 204h, according to one embodiment. The IEM data framework 102 further includes IEM data 200 and the hub, shown here embodied as the handheld device 402. In various aspects, the auto billing system 204h may interoperate, or be otherwise associated with, one or more IEM data systems 204 and/or one or more commercial systems 106.

In one scenario, various parties such as patient 506, physicians, pharmaceutical companies, etc., subscribe to information feeds/patient population data of IEM data 200 to further business goals, manage health care, etc. The parties may receive the information feeds/access population data, etc. via a variety of devices. For example, patient 506 may receive an information feed via hub 202 embodied as the handheld device 402, which, via a software agent, may generate a financial transaction in the form of an invoice for the information feed displayed for the patient 506. Payment may be effected via automated methods.

In a patient selection method, for example, the patient selects various payment options via the software agent resident on the handheld device 402. A payment transaction is generated and communicated to the financial transaction system 106e. The financial transaction system 106e automatically charges an account associated with the patient 506. Confirmation of the payment together with digital, e.g., electronic, copies of the invoice are provided to the software agent resident on the handheld device 402 for the patient 506 to view, etc.

In an automated method, for example, a bill and/or financial transaction are automatically generated upon predetermined criteria. The predetermined criteria include, for example, delivery of information associated with an information feed or other source, access to a data collection, e.g., patient population data stored in a database, etc. The patient selects various payment options via the software agent resident on the handheld device 402, and a payment transaction is generated and communicated to the financial transaction system 106e. The financial transaction system 106e automatically charges an account associated with the patient 506. Confirmation of the payment together with digital copies of the invoice are provided to the software agent resident on the handheld device 402 for the patient 506 to view, etc. For example, a healthcare provider may access patient population data stored in decision support system 204b via the healthcare system 106a. Software of the decision support system 204b may cooperate with the software 502 and the database 504 of the auto billing system 204h to identify the party to be billed for the access. Upon identification, the auto billing system 204h may automatically generate a bill and/or financial transaction for the access via one or more of the aforedescribed channels.

2.3.9 Tracking Systems

Tracking systems track and integrate product movement data. In one example, the life cycle of an ingestible device may be tracked from manufacture to shipment, pharmacy inventory, delivery to patient, ingestion and expulsion.

Figure 14:
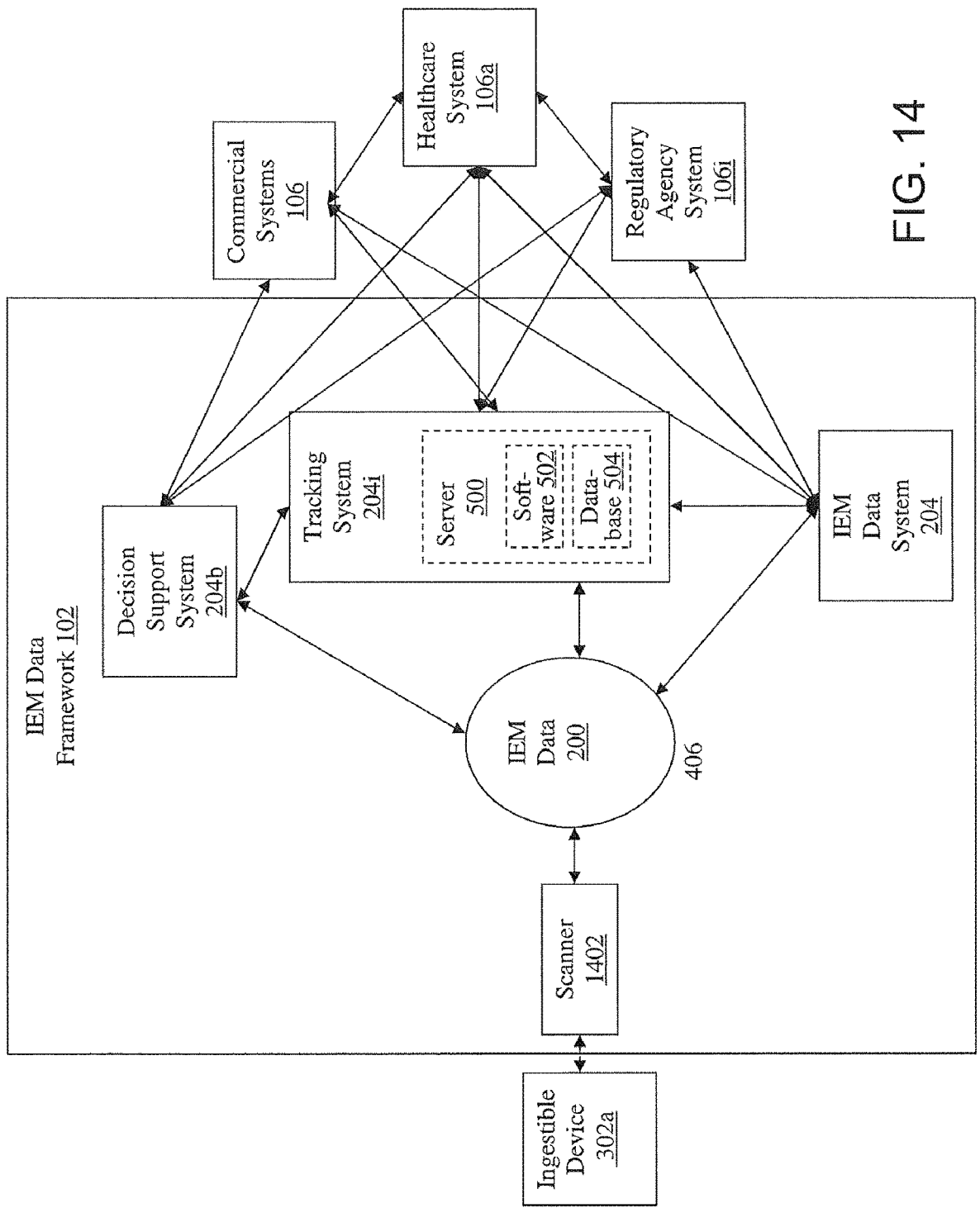
FIG. 14 illustrates an exemplary IEM data framework having a tracking system, according to one embodiment.

FIG. 14 illustrates an exemplary IEM data framework 102 having a tracking system 204i, according to one embodiment. The IEM data framework 102 further includes the IEM data 200 and the hub, shown here embodied as a scanner 1402. In various aspects, the tracking system 204i, may interoperate, or be otherwise associated with, one or more IEM data systems 204 and/or one or more commercial systems 106.

In one scenario, a pharmaceutical manufacturer produces an ingestible device 302a such as a particular medication having an IEM system device therein. The IEM system device contains various IEM data 200 such as medication identification, batch number, lot number, and manufacturer identification. The scanner 1402 may be utilized at various times/locations to scan the ingestible device 302a and capture the IEM data 200 associated therewith. The IEM data 200 may then be stored, processed, etc., via, for example, the software 502 and the database 504 of the tracking system 204i. For example, the IEM data 200 may be read by the scanner at a shipping point and when received by a pharmacy to ensure inventory control, distribution integrity, and chain of custody for restricted pharmaceuticals, etc.

The tracking information may be used, for example, by regulatory agencies systems 106i to determine regulatory adherence, etc.

2.3.10 Interdiction Systems

Interdiction systems track, reconcile, and support interdiction programs. The interdiction programs include, for example, programs related to drug identification and use detection by sworn personnel, search and seizure activities, etc.

Figure 15:
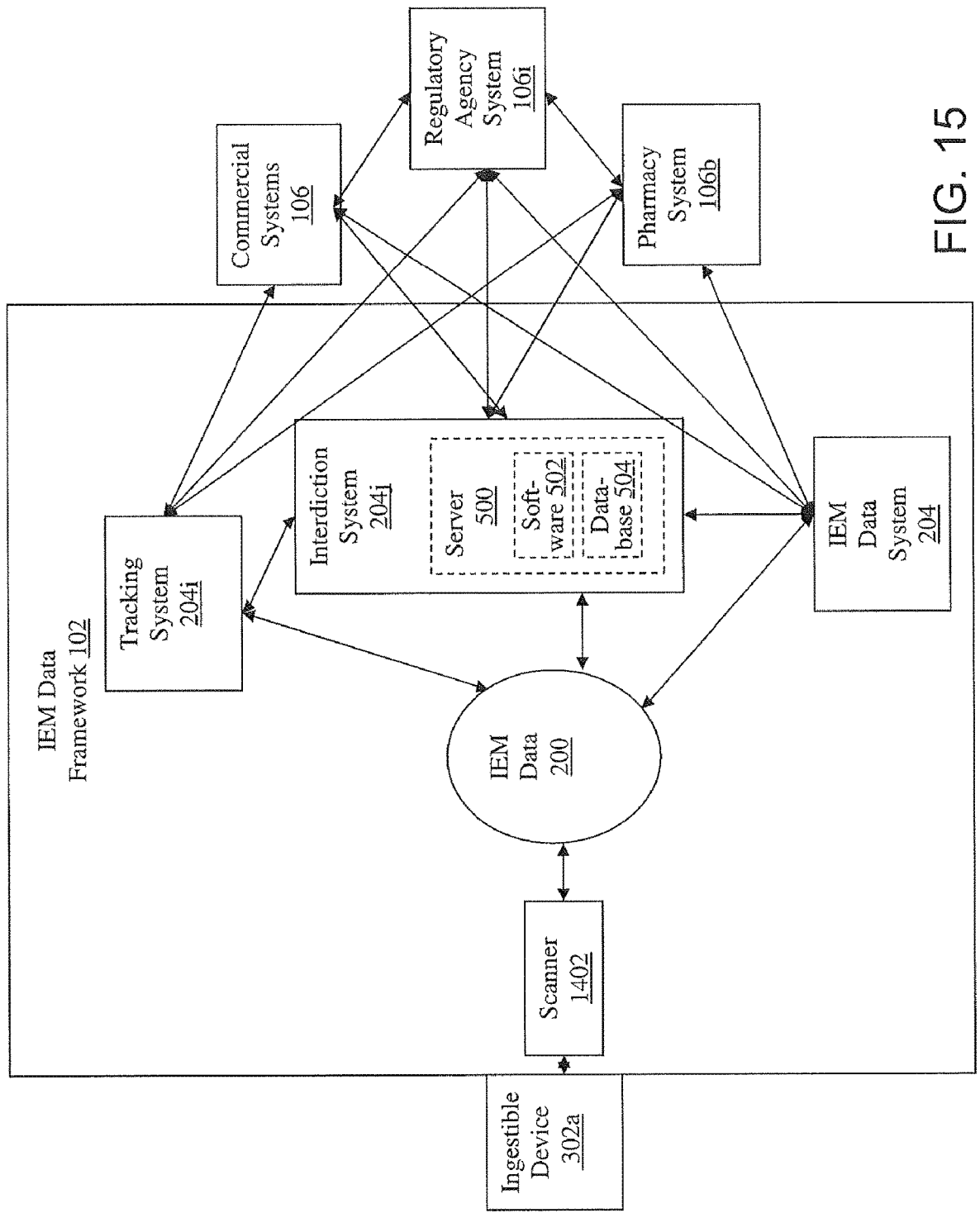
FIG. 15 illustrates an exemplary IEM data framework having an interdiction system, according to one embodiment.

FIG. 15 illustrates an exemplary IEM data framework 102 having an interdiction system 204j, according to one embodiment. The IEM data framework 102 further includes IEM data 200 and hub, shown here embodied as a scanner 1402. In various aspects, the interdiction system 204j may interoperate, or be otherwise associated with, one or more IEM data systems 204 and/or one or more commercial systems 106.

In one scenario, a pharmaceutical manufacturer produces an ingestible device 302a such as a particular medication having an IEM system device therein. The IEM system device contains various IEM data 200 such as medication identification, batch number, lot number, and manufacturer identification. The scanner 1402 may be utilized at various times/locations to scan the ingestible device 302a and capture the IEM data 200 associated therewith. The IEM data 200 may then be communicated to, for example, the software 502 and the database 504 of the interdiction system 204j, where the IEM data 200 may be accessed by and communicated to regulatory agency systems 106i to facilitate various regulatory and enforcement functions, to locate missing controlled substances, to intercept contraband, to identify unknown substances, and to otherwise support agency and regulatory activities.

In various aspects, the IEM data 200 may be communicated to/from, for example the interdiction system 204j from/to the tracking system 204i, for processing, storage, etc. For example, the IEM data 200 may be read by the scanner at a shipping point and read by a pharmacy to ensure inventory control, distribution integrity, and chain of custody for restricted pharmaceuticals, etc. The scanned (read) IEM data 200 may be reconciled between the interdiction system 204j and the tracking system 204j to ensure complete shipment, to track shipments through various jurisdictions, etc. In one example, the IEM data 200 such as the identifier data, shipment data, patient information, recipient information, and commercial activities are tracked and reconciled to intercept contraband and otherwise support agency and regulatory activities.

2.3.11 Subscription Systems

Subscription systems enable subscription to various IR information feeds and data/knowledge collections, e.g., IEM data collection system. For example, patients subscribe to IEM data information feeds and/or IEM data collections, which aggregate various sources of data and fuse the data into integrated, individualized information based on the subscriber's requirements. The information fusion may include, for example, personalized medication regimens and alert applications, individual social community information, music, etc. The information may be automatically billed, for example, under a single point of charge model on a recurring basis. The agent may be provided as part of an embedded device, e.g., standard application on a mobile telephone, etc.

Figure 16:
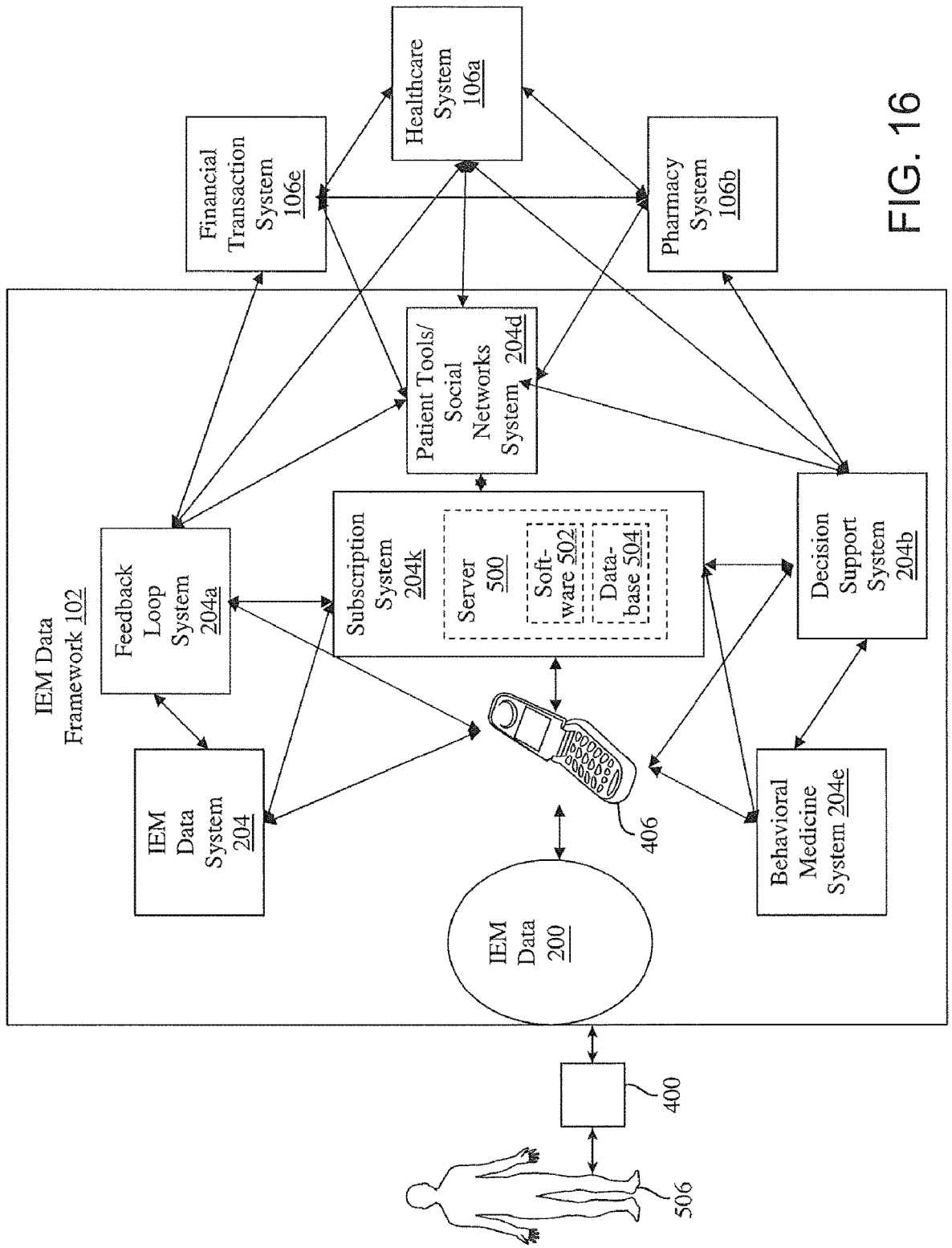
FIG. 16 illustrates an exemplary IEM data framework having a subscription system, according to one embodiment.

FIG. 16 illustrates an exemplary IEM data framework 102 having a subscription system 204k, according to one embodiment. The IEM data framework 102 further includes IEM data 200 and the hub, shown here embodied as a mobile telephone 406. In various aspects, the subscription system 204k may interoperate, or be otherwise associated with, one or more IEM data systems 204 and/or one or more commercial systems 106.

In one scenario, the patient 506 subscribes to various information feed(s) and/or IEM data collections, discussed hereinafter in detail. The information feed(s) include, for example, structured and non-structured information on a variety of topics generated or delivered from various sources, e.g., websites, blogs, etc. The IEM data collections include storage repositories having IEM data. The storage repositories may be associated, e.g., integral to or remote from, the subscription system 204k. For example, an IEM data collection may be resident in part or wholly in database 504 of the subscription system 204k.

In one scenario, IEM data 200 are communicated from a subscription source to a subscriber, e.g., a subscriber's device. The subscription source includes, for example, IEM data systems 204, e.g., the database 504 of the subscription system 204k, feedback loop system 204a, patient tools 204d, and decision support system 204b; commercial systems 106b, e.g., online medical and business information/newsfeed sources, healthcare system 106a; and other sources, e.g., devices associated with the patient 506, the hub, etc. The subscriber includes, for example, a person, group, or resource, e.g., a database, a computer system, server, network, etc.

In various aspects, subscription services may be initiated via, for example, a software agent resident on the hub or communication with a local or remote system such as the healthcare system 106a.

In various aspects, the subscriptions services may be billed and paid via, for example, the subscription system 204k and the financial transaction system 106e.

In various aspects, the subscription newsfeeds/data may be combined or integrated into a single or multiple newsfeeds, e.g., the software 502 and/or the database 504 of the subscription system 204k may enable data aggregation, etc.

To illustrate, the patient 506 subscribes to a healthcare newsfeed and a pharmacy newsfeed, one or more having IEM data 200, via the subscription system 204k. The patient subscribes by selecting an application, e.g., software agent resident on the hub, illustratively embodied here as the mobile telephone 406. Once the patient has selected the subscription options, the order is communicated to the subscription system 204k, which, via the software 502 and the database 504, confirms, processes, stores, and bills the order. The subscriber's financial account may be automatically charged, for example, by communicating invoice information to a financial transaction system 106e associated with the subscriber's account. Confirmation of the charge may be communicated from the financial transaction system 106e to the subscriber via the subscription system 204k and/or the mobile telephone 406.

Based on the subscription parameters, the subscription system 204k receives the healthcare newsfeed information and the pharmacy newsfeed information. The software 502 of the subscription system compares subscriber data of the patient 506 in the database 504 against subscriber data found in the pharmacy newsfeed, e.g., patients who are prescribed medications for cardiac therapy. Based on the comparison, software 502 separates the data of the pharmacy newsfeeds relevant to the subscriber, combines the relevant data with the healthcare newsfeed information and communicates the combined newsfeed information to the mobile telephone 406 for access and display.

2.3.12 IEM Data Collection System

The IEM data collection system provides/facilitates access to/storage of the IEM data. Examples of the IEM data include patient population data and electronic medical records. In various aspects, IEM data collections may include functionality related to the collection, management, manipulation, storage, dissemination, and billing of IEM data.

Figure 17:
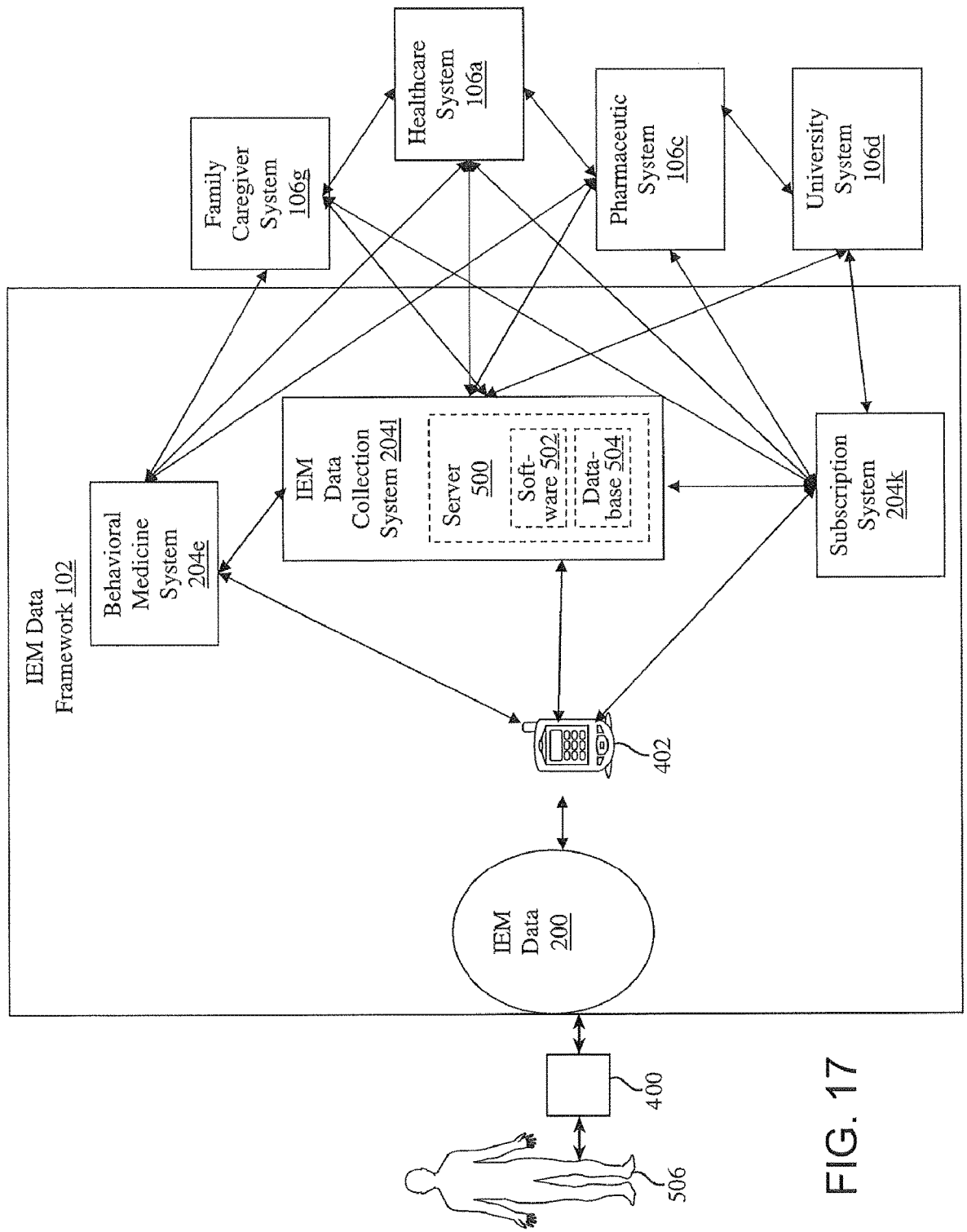
FIG. 17 illustrates an exemplary IEM data framework having an ingestible event marker data collection system, according to one embodiment.

FIG. 17 illustrates an exemplary IEM data framework 102 having an IEM data collection system 204l, according to one embodiment. The IEM data framework 102 further includes IEM data 200 and the hub, shown here embodied as a handheld device 402. In various aspects, the IEM data collection system 204l, may interoperate, or be otherwise associated with, one or more IEM data systems 204 and/or one or more commercial systems 106.

In one scenario, patient population data, e.g., anonymized, empirical patient data, is stored in one or more repositories, e.g., the database 504 of the IEM data collection system 204l. The patient population data may be received from various sources, e.g., the IEM data 200 associated with one or more patient 506, IEM data systems 204 such as behavioral medicine systems 204e, subscription systems 204k, patient tools 204d, etc., and commercial systems such as healthcare systems 106a, pharmaceutic systems 106c, university systems 106d, etc.

In various aspects, the IEM data collection system 204l may be consolidated in a single physical and/or logical location, e.g., the database 504 of the server 500 of the IEM data collection system 204l, or distributed across two or more systems or locations, e.g., remotely distributed on multiple IEM data systems 204, associated with commercial systems 106, and/or distributed between the IEM data collection system 204l and other systems/locations.

Multiprofile users may access, utilize, and/or contribute to the IEM data collection system 204l. Multiprofile users include, for example, individuals or groups using various methods/devices for access, utilization, and/or contribution. Examples of multiprofile users include patient 506, family members and family caregivers, professionals, academics, corporates, etc. The methods/devices include the hub devices such as a mobile telephone, base station, handheld device, etc., as well as system components associated with IEM data systems and commercial systems, e.g., laptop computer associated with a university network, a desktop computer associated with the family caregiver system 106g, etc.

To continue the foregoing illustration, a researcher, using the university system 106d, accesses the IEM data collection system 204l via the Internet, etc. and submits queries against the patient population data, extracts various data, etc.

In various aspects, the IEM data collection system 204l includes privacy assurance, authentication, and validation mechanisms with respect to financial, medical, and other privacy information. For example, the software 502 may authenticate users. The software 502 may cleanse/verify data to ensure predetermined privacy thresholds are met.

2.3.13 Approval Systems

Approval systems aggregate and/or analyze various data to enable an informed approval decision.

Figure 18:
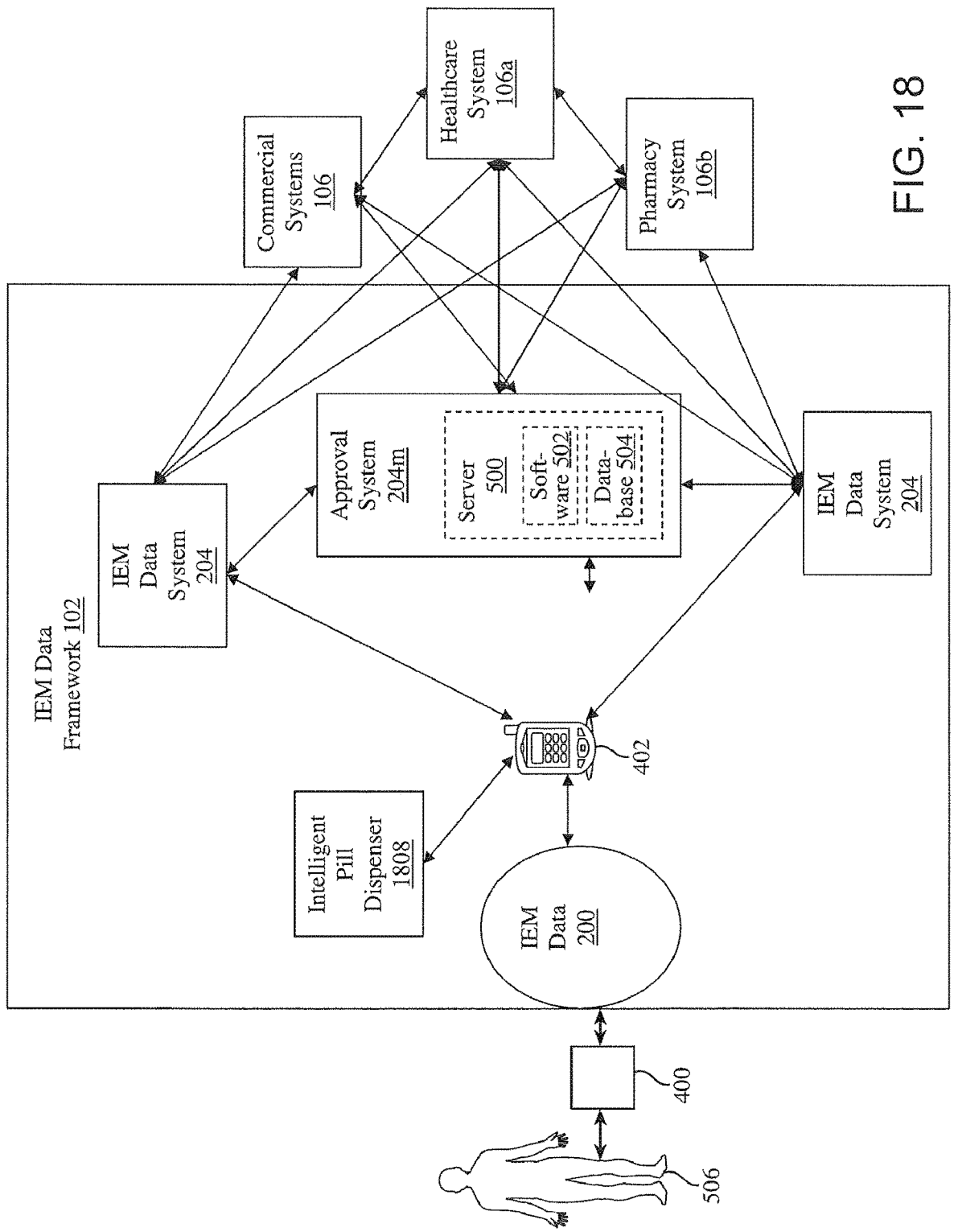
FIG. 18 illustrates an exemplary IEM data framework having an approval system, according to one embodiment.

FIG. 18 illustrates an exemplary IEM data framework 102 having an approval system 204m, according to one embodiment. The IEM data framework 102 further includes IEM data 200, the hub, shown here embodied as a handheld device 402, and an associated intelligent pill dispenser 1802. In various aspects, the approval system 204m, may interoperate, or be otherwise associated with, one or more IEM data systems 204 and/or one or more commercial systems 106.

In one scenario, the patient 506 opens an intelligent pill dispenser 1802, e.g., a pill dispenser having a microchip and communication abilities. The patient 506 removes a pill having an IEM system from the intelligent pill dispenser 1802. The intelligent pill dispenser 1802, via its microchip, senses the removal of the pill, receives a signal from an IEM system that the patient 506 has ingested the pill, and determines the remaining quantity. If the remaining quantity is fewer than a predetermined threshold quantity, the intelligent pill dispenser 1802 communicates a refill request to the approval system 204m. The approval system 204m via, for example, the software 502 and the database 504, verify information associated with the patient 506, e.g., patient name, prescription identification, medication ingestion verification, refill timing, etc. The approval system 204m may interoperate with, e.g., communicate with, various IEM data systems 204 and/or commercial systems 106 to obtain/validate information. For example, data provided to/resident in the approval system 204m may be reconciled with medical records of healthcare system 106, the refill request approved by approval system 204m, and a refill communicated to the pharmacy system 106b.

2.3.14 Forecasting Systems

Forecasting systems aggregate data and/or facilitate analysis of the aggregated data/data collections to derive/generate predictive information.

Figure 19:
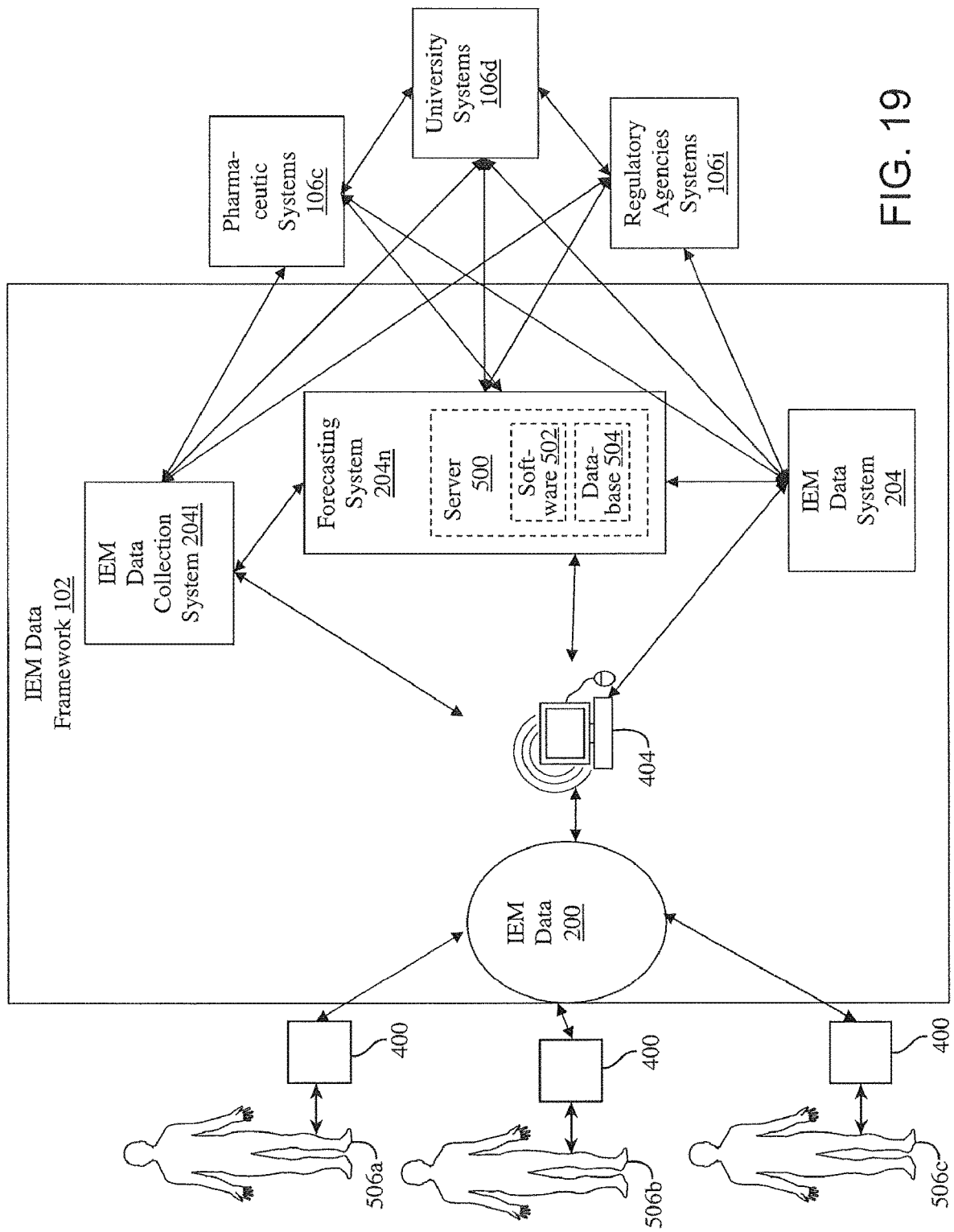
FIG. 19 illustrates an exemplary IEM data framework having a forecasting system, according to one embodiment.

FIG. 19 illustrates an exemplary IEM data framework 102 having a forecasting system 204n, according to one embodiment. The IEM data framework 102 further includes IEM data 200 and the hub, shown here embodied as a base station 404. In various aspects, the forecasting system 204n, may interoperate, or be otherwise associated with, one or more IEM data systems 204 and/or one or more commercial systems 106.

In one scenario, for example, IEM data 200 are received by the base station 404 from ingestible devices associated with patients 506a-c. The base station 404 communicates the IEM data 200 to the IEM data collection system 204l, which anonymizes the IEM data 200 and aggregates the anonymized IEM data 200 with patient population data.

The IEM data collection system 204l communicates all or a portion of the patient population data to the forecasting system 204n, where the software 502, e.g., one or more applications, processes the patient population data to derive various statistics, conclusions, forecasts, etc., according to predetermined requirements, objectives, etc. For example, the software 502 processes the patient population data and correlates various data such as blood pressure readings over a predetermined period of time versus medication taken versus adherence to medication regimen to determine overall efficacy of medication regimen and to forecast titrated patient dosing based on the overall efficacy findings.

Multiple profile parties, e.g., analysts using the pharmceutic systems 106e, agents using the regulatory agency systems 106i, and researchers using the university systems 106d, access the forecasting system 204n. The multiple profile parties utilize various tools, e.g., the software 502, to run analytical and forecasting applications again the patient population data and to access various forecasting data available in connection with the forecasting system 204n.

2.3.15 Financial Systems

Financial systems support and enable financial transactions associated with IEM data. In various aspects, the financial systems are communicably interoperable with existing automated banking systems and networks, etc.

Figure 20:
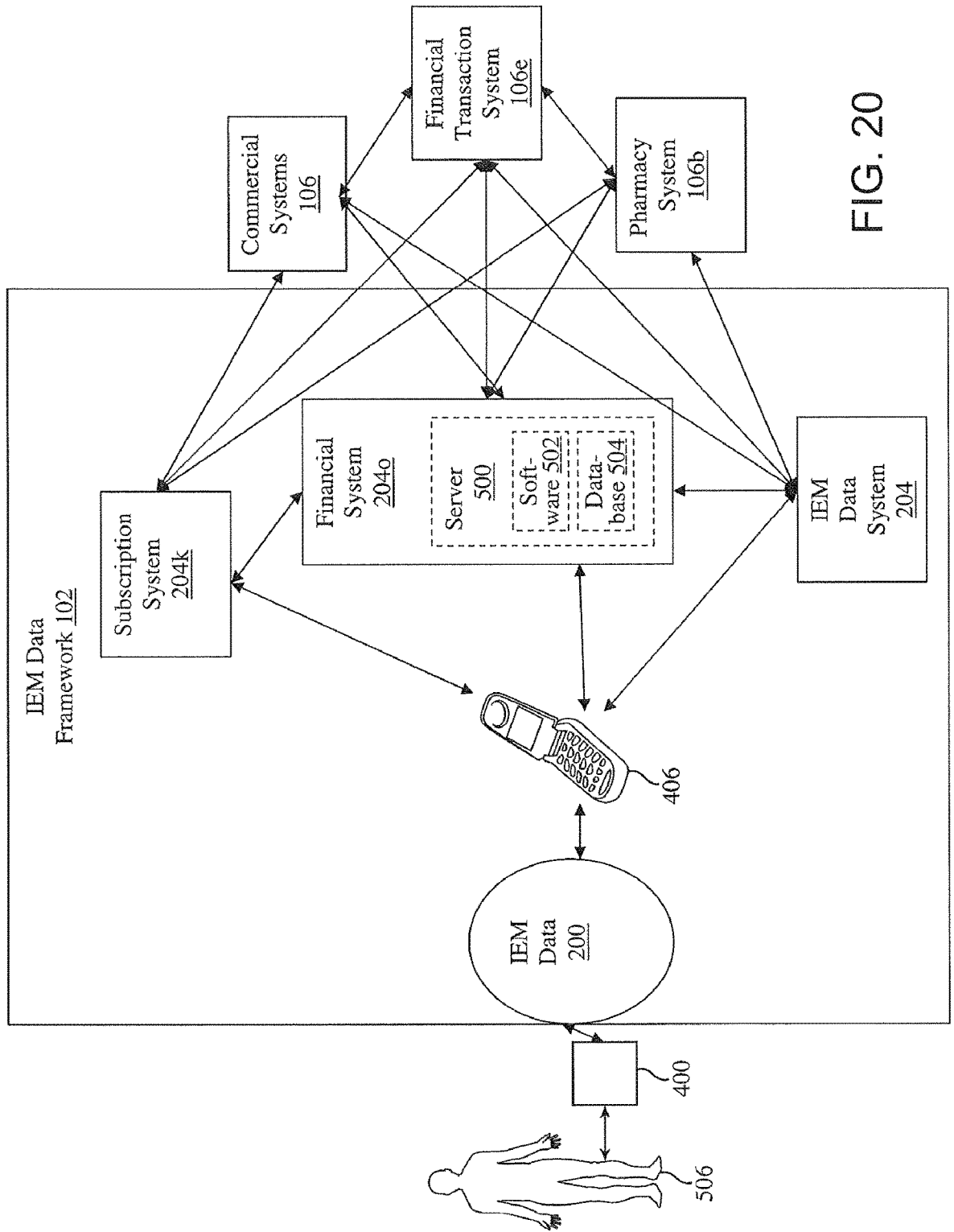
FIG. 20 illustrates an exemplary IEM data framework having a financial system, according to one embodiment.

FIG. 20 illustrates an exemplary IEM data framework 102 having a financial system 204o, according to one embodiment. The IEM data framework 102 further includes IEM data 200 and the hub, shown here embodied as a mobile telephone 406. In various aspects, the financial system 204o, may interoperate, or be otherwise associated with, one or more IEM data systems 204 and/or one or more commercial systems 106.

In one scenario, the patient 506, via the mobile telephone 406, places an order for a product/service, e.g., a newsfeed service from the subscription system 204k. The subscription system 204k, via its software, interoperates with the financial system 204o. The subscription system 204k, for example, securely communicates encrypted patient financial information such as account number and subscription information. The financial system 204o authenticates the patient information and securely interoperates with the patient's financial institution, e.g., via a commercial system 106 such as the financial transaction system 106e to charge the patient's account and provide charge information/confirmation to the patient 506 via, for example, the mobile telephone 406.

2.3.16 IEM Data Phone

The IEM data phone enables IEM data-related applications. For example, application(s) include pill regimen scheduling applications, alert reminder applications, auto refill for medication applications, patient tool applications, social networking applications, incentive tracker applications, auto billing applications, subscription applications, approval applications, and financial transaction applications. The applications may be integrated with, associated with, or independent of one another. The applications may further be manufacturer-installable on the IEM data phone, downloadable or otherwise installable by a wholesaler, retailer, user, etc. Installation may be independent or bundled with other software, products, etc. In various aspects, the applications are user-configurable, downloadable, upgradeable, etc.

In various aspects, the IEM data phone and/or its applications may share common features, e.g., a common graphical user interface (GUI); branding, i.e., a collection of images and ideas representing an economic producer such as concrete symbols embodied as a name, logo, slogan, design scheme, etc. The IEM data phone may also include various connectivity schemes, e.g., Internet and cellular; may provide multimedia capabilities; and may embody various hardware and software configurations. The IEM data phone may be embodied in a variety of devices, e.g., the mobile telephone 406, the handheld device 402, etc.

Figure 21:
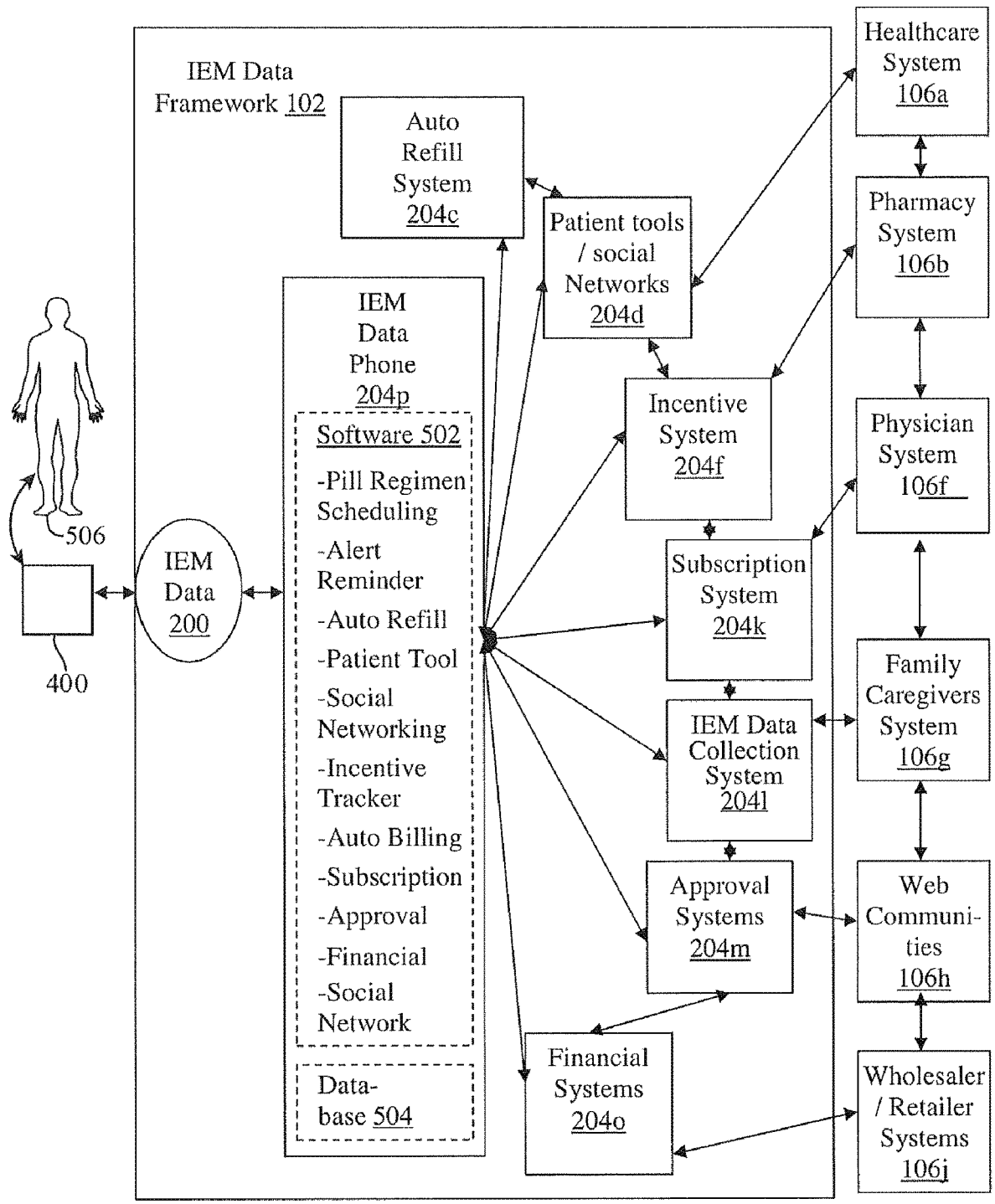
FIG. 21 illustrates an exemplary IEM data framework having an ingestible event marker data phone system, according to one embodiment.

FIG. 21 illustrates an exemplary IEM data framework 102 having an IEM data phone 204p, according to one embodiment. The IEM data phone 204p may serve as the hub, for example. IEM data framework 102 further includes IEM data 200. In various aspects, the IEM data phone 204p, may interoperate, or be otherwise associated with, one or more IEM data systems 204 and/or one or more commercial systems 106.

In one scenario, the IEM data phone 204p includes the software 502, e.g., a portfolio of branded applications such as pill regimen scheduling, alert reminders, auto refills, patient tools, social networking, incentive trackers, auto billing, subscriptions, approvals, and financial applications.

The pill regimen scheduling application may accept, reconcile, calendar, and manage contraindications and interactions of medication regimen(s). For example, the patient 506 may input information related to one or more prescriptions, including the pharmaceutical name and dosage. The pill regimen scheduling application may check the input information against existing information stored on the IEM data phone 204p, e.g., in the database 504, or elsewhere, e.g., the pharmacy 106b. The pill regimen scheduling application may provide information regarding contraindicated medications, side effects, precautionary instructions. The pill regimen scheduling application may calendar the dosing information and generate alerts, e.g., reminders generated at appropriate times alerting the patient to ingest the medication. The alerts may be audible, visual, email, text message, etc. and may be integrated with, or independent of, alert reminder application(s).

The alert reminder application may accept or access various data associated with scheduling, including IEM data 200, and generate alerts at appropriate times. The alerts may be audible, visual, email, text message, etc. and may be integrated with or independent of alert reminder application(s). The alert application may be user-configurable, e.g., type of alert, repetition of alert, interval of repetition, receivers of alert. The alerts may be associated with various devices of the patient, family caregivers, friends, etc. In one example, the patient 506 may schedule reminders to be sent to the user's device, e.g., the IEM data phone 204*p*, the handheld device 402, the base station 404, the mobile telephone 406, etc.

The alert reminder application may be integrated with other applications/systems. To illustrate an IEM system associated with the patient 506 that may, for example, detect medication ingestion event(s) and communicate the IEM data 200 associated with the medication ingestion event(s) to the alert reminder application via the IEM data phone 204*p*. The alert reminder application may interoperate with the pill regimen scheduling application and perform various checks, e.g., the ingested medication was actually prescribed for the person that ingested it; the ingested medication was ingested in the correct dosage; the ingested medication was ingested at the prescribed time interval; etc.

Predetermined criteria may be used to determine if/when the alert reminders application generates an alert, reminder, etc. To continue with the foregoing illustration, upon a determination that the ingested medication was not prescribed for the person ingesting it or the wrong dosage was ingested, the alert reminder system generates alert(s) to a predetermined destination, e.g., alerts in the form of text messages to mobile telephones associated with the family caregiver system 106*g*, alerts in the form of email/text messages to the healthcare system 106*a* and the physician system 106*f*. If the event is deemed critical, e.g., ingestion of non-prescribed medication, overdosage, etc., the alert reminder application may generate a call from the IEM data phone 204*p* to the emergency assistance system, e.g., place a 911 call. The call (prerecorded audio, text message, etc.) may contain information such as the patient's name, the nature of the emergency, the ingestion details, physician and family caregiver information, and the physical location of the person ingesting the medication.

The auto refill application may facilitate automatic refill of a prescription medication via interoperation with, for example, the pharmacy system 106*b*, etc.

The patient tool application may be provided on or accessible from the IEM data phone 204*p*. For example, software tools for tracking dietary and physiologic symptoms may facilitate user entry of dietary intake and symptoms, collection of device-associated physiologic parameters such as blood pressure, heart rate, etc., correlation/analysis of the data, and feedback based on the correlation/analysis. The patient tool application may provide data, e.g., the feedback, for display on the IEM data phone 204*p*, the IEM data system(s) 204, and/or the commercial system(s) 106.

The social networking application may facilitate social networking functionality. For example, the social networking application may retain various links to selected profiles of various social networks, receive data related to the selected profiles, e.g., updates to the profiles, facilitate messaging and other communication, update the user's profile, etc., communicate with the IEM data systems(s) 204, and/or the commercial system(s) 106, such as the patient tools/social network 204*d* and the web communities 106*h*.

The incentive tracker application may collect, manage, track, update, etc. incentive information. For example, the incentive tracker application may reconcile data associated with IEM data collection systems 204*l* and wholesaler/retailer systems 106*j* to determine incentive eligibility, e.g., a patient rebate. The incentive tracker application may further tally points under various reward systems, notify the patient 506 of milestones, goals, award of incentive, etc.

The auto billing application may facilitate billing for various transactions. The auto billing application may interoperate with various applications/systems, including the IEM data system(s) 204 and/or the commercial system(s) 106, such as the billing for an auto refill via the pharmacy system, etc.

The subscription application facilitates ordering, receipt, management, etc. of various subscriptions, e.g., newsfeeds, access to various data collections on a subscription basis, etc. The subscriptions application may interoperate with various applications/systems, including the IEM data system(s) 204 and/or the commercial system(s) 106, such as the subscription system 204*k*, the IEM data collection system 204*l*, etc.

The approval application aggregates and/or analyzes various sources of data to enable an informed approval decision. The approvals application may interoperate with various applications/systems, including the IEM data system(s) 204 and/or the commercial system(s) 106, such as the auto refill system 204*c*, the subscription system 204*f*, the financial systems 204*o*, the pharmacy systems 106*b*, the wholesaler/retailer systems 106*j*, etc.

The financial application supports and enables financial transactions associated with IEM data 200. The financial application may interoperate with various applications/systems, including the IEM data system(s) 204 and/or the commercial system(s) 106, such as the auto refill system 204*c*, the incentive system 204*f*, the subscription system 204*k*, the approval system 204*m*, the financial systems 204*o*, the pharmacy system 106*b*, the wholesaler/retailer systems 106*j*.

2.3.17 Social Network System

Social networks are a social structure made of one or more nodes, e.g., components such as websites, accessed by individuals or organizations. The social network is typically tied by one or more specific types of interdependency, such as epidemiology, therapeutic regimen, healthcare management, etc., and thus may attract the interest of otherwise unrelated individuals and groups having in common an interest in the interdependencies. Social networks may be built around various communities, e.g., family caregivers, patients, medical conditions, etc.

One example of a social network is a patient information community that provides information related to a particular medical condition, treatments, medications, regimens, and side effects based on both provider and anecdotal data. The availability of such data may provide benchmark-type services, e.g., facilitate self-assessment of personal progress and adjustment in therapies and behaviors by comparing and contrasting an individual's progress with the particulars of others having the same condition, similar therapies, etc.

Figure 22:
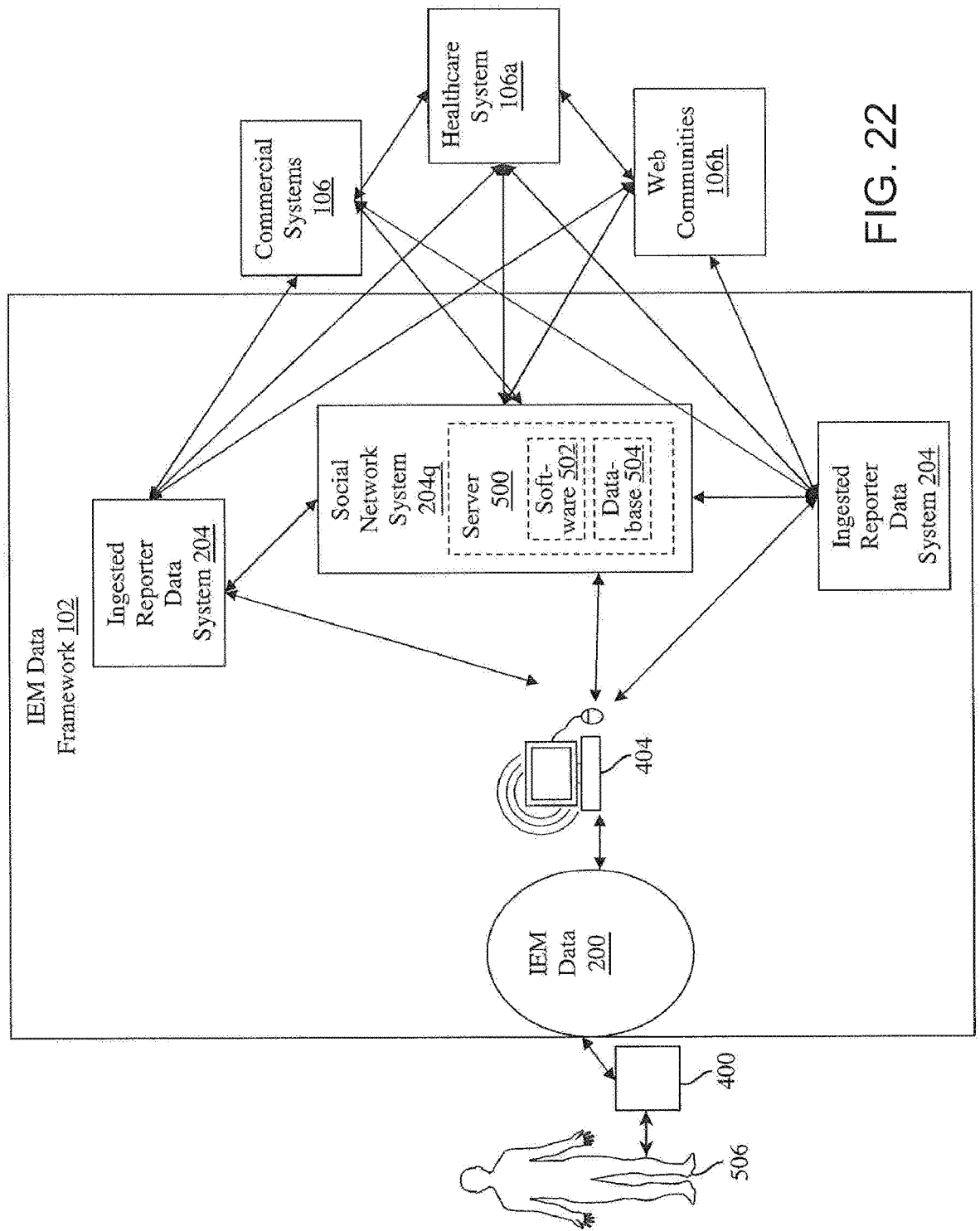
FIG. 22 illustrates an exemplary IEM data framework having a social network system, according to one embodiment.

FIG. 22 illustrates an exemplary IEM data framework 102 having a social network system 204*q*, according to one embodiment. The IEM data framework 102 further includes IEM data 200, and the hub, shown here embodied as the base station 404. In various aspects, the social network system 204*q* may interoperate, or be otherwise associated with, one or more IEM data systems 204 and/or one or more commercial systems 106.

In one scenario, patient 506 suffers from a cardiac condition. The patient 506 accesses the social network system 204*q*, which may be embodied as the server 500 having the software 502 and the database 504 having IEM data 200. Patient 506 may access the social network system 204*q*, for example, via the base station 404. The patient 506*a* searches the database 504 for patient profiles also having cardiac conditions similar to that of patient 506. The social network system 204*q* provides multiple profiles of patients having similar conditions. The profiles include various data pertinent to each patient such as medication therapies, personal behavior histories, etc. The patient 506 requests a comparison of his medication therapy, medication therapy adherence, and behavior to that listed in the profiled. The social network system 204*q* provides the requested comparative data in the form of a graphical display. From the display, the patient 506 is able to determine the profiles having the most favorable treatment outcomes. From such profiles, the patient 506 and/or social network system 204*q* analyze the differences between his medication, medication therapy adherence, behavior, etc. and the corresponding interdependencies of the profiles having the most favorable treatment outcomes. The analysis may contrast the differences found in various areas, as well as generate prescriptive advice, e.g., in which areas the patient 506 may want to adjust and specific adjustments based on the analysis. The patient 506 may adopt the prescriptive advice, i.e., adjust accordingly, to improve his own personal outcome. Further, the patient 506 may update the social network system 204*q* with the adjustment data, which may be used in the future for tracking personal improvement as well as benchmarking purposes by other individuals. In various aspects, the social network system 204*q* may be communicably associated with other web communities 106*h*, e.g., youth communities, business communities, etc.

3.0 IEM Data Framework Method

One aspect comprises, for example, receiving, via a hub, ingestible event data that originates from multiple ingested event markers; and communicating, via the hub, at least a portion of the ingestible event marker data to at least one ingestible event marker data system.

4.0 IEM Data Framework Article

One aspect comprises, for example, a storage medium having instructions, that when executed by a computing platform, result in execution of a method of utilizing ingestible event marker data, comprising: receiving, via a hub, the ingestible event data that originates from multiple ingested event markers; and communicating, via the hub, at least a portion of the ingestible event marker data to at least one ingestible event marker data system.

5.0 IEM Data Framework System

One aspect comprises, for example, a receive module to receive, via a hub, ingestible event data that originates from multiple ingested event markers; and a communicate module to communicate, via the hub, at least a portion of the ingestible event marker data to at least one ingestible event marker data system.

6.0 IEM Data Framework Data Modeling and Prescriptive Outcomes

In various aspects of the present invention, various techniques, e.g., state characterization based on multi-variate data fusion techniques, may be employed to generate various output, e.g., analyses, metrics, predictive information, etc. For example, an aspect may include data captured and processed to create metrics that are descriptive and/or predictive of an impending health event such as a stroke or an indicator of future behavioral choices, e.g., whether a person will adhere to a medication regimen if such medication is prescribed in the future.

Figure 23:
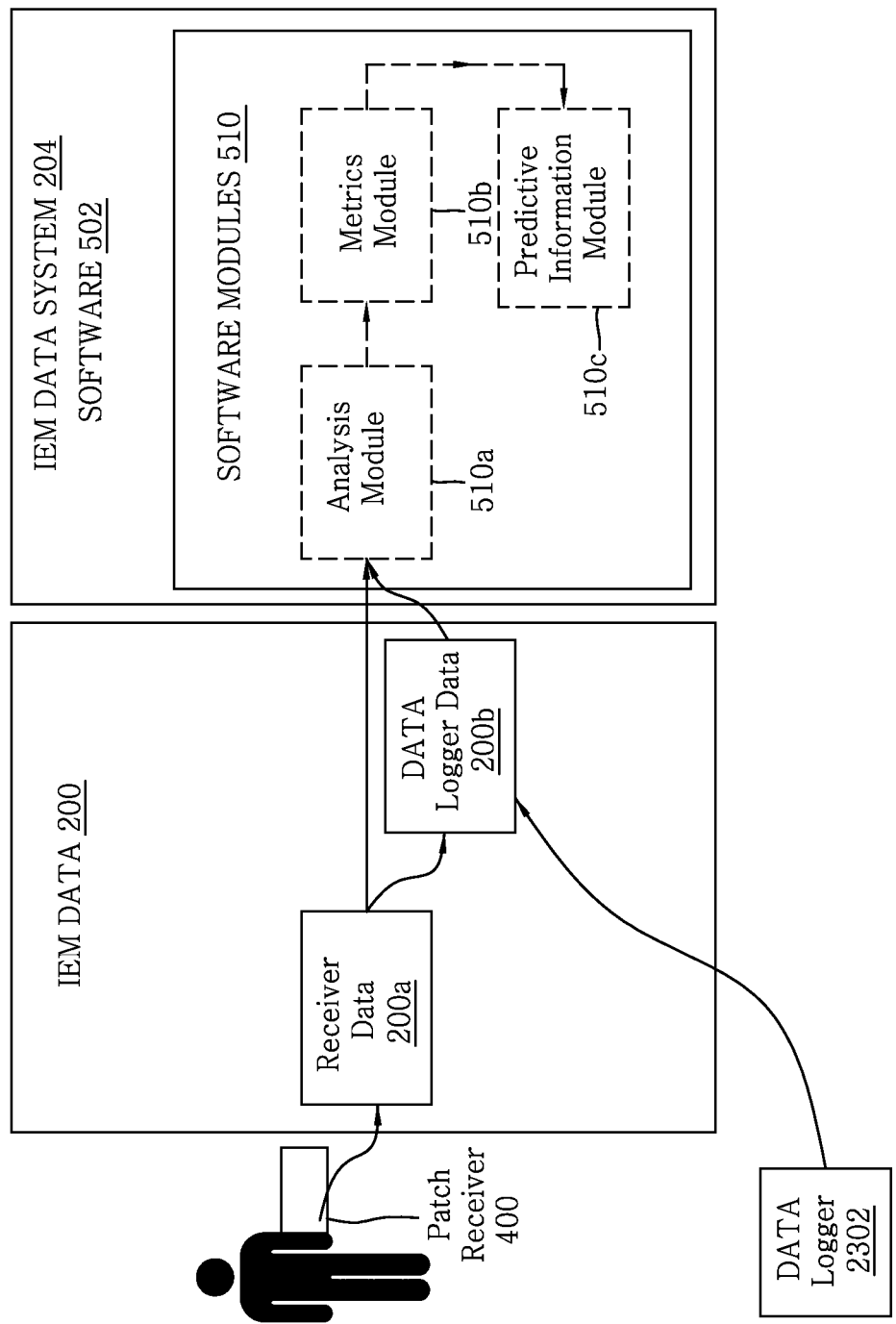
FIG. 23 illustrates exemplary modules of software of an exemplary IEM data system.

To illustrate with reference to FIG. 23, there are shown exemplary software modules 510*a-c* of exemplary software 502 of exemplary IEM data system 204. More particularly, and with continuing reference to the figures herein, IEM data 200 may be a predetermined set of data. In one example, the IEM data 200 are data gathered by a patch receiver 400 and, optionally, a data logger 2302. The IEM data are provided to an IEM data system 204 such as the forecasting system 204*n*?. The IEM data system 204 includes software modules 510 having one or more of an analysis module 510*a*, a metrics module 510*b*, and a predictive information module 510*c*.

To continue the illustration, sensors and data loggers capture longitudinal data. In one example, the patch receiver 400 gathers physiologic data such as positional data associated with the user of the patch receiver 400 and provides the receiver data 200*a* to the analysis module 510*a*. In one example, positional X, Y, Z data of the use is captured at a predetermined rate or schedule. Data logger 2302 gathers data logger data 200*b* such as quality of sleep, etc., and provides the data logger data 200*b* to the analysis module 510*a*. The analysis module 510*a* analyzes the positional data and the data logger data 200*b* and provides analysis data to the metrics module 510*b* for metric generation. In one example, the captured positional data are analyzed by at least time-normalizing and interpolating to generate a fixed time of day grid. This information is provided to the metrics module 510*b* to generate various metrics such as the average diurnal pattern, the standard deviation across days, and the overall variability. From the metrics, the predictive information module 510*c* generates predictive information. For example, the metrics may be analyzed to predict that the user is very likely to adhere to a medication regimen. Alternatively, the medication adherence data may be tracked, e.g., via IEM event data collected from an ingestible sensor such as an IEM or RFID device, etc., and, when analyzed alone or with other data, the predictive information module 510*c* may generate a characterization of patent stability while on the medication regimen or other therapy.

One skilled in the art will recognize that the software modules 510*a*, 510*b*, and 510*c* may be centrally associated with a single system component, e.g., the IEM data system 204, or may be distributed across and/or associated with various system components, e.g., the patch receiver 400, the hub 202, and/or one or more IEM data systems 204. In the foregoing examples and in various aspects of the present invention, calculation and analyses may be accomplished via one or more modules, or combinations thereof, and/or with other software.

Additional examples are set out in Table 1, entitled "Examples" hereinafter.

TABLE 1

"Examples"

| | IEM Data 200 | Analysis Module 510a | Metrics Module 510b | Predictive Information Module 510c |
| --- | --- | --- | --- | --- |
| Example 1: Patient 1 | IEM data are derived from the patch receiver, | Data are time-normalized and interpolated to a | The average diurnal pattern is calculated. | Circadian rhythm regularity |

TABLE 1-continued

"Examples"

| | IEM Data 200 | Analysis Module 510a | Metrics Module 510b | Predictive Information Module 510c |
|---|---|---|---|---|
| | The IEM data include accelerometer data associated with the patch receiver. The accelerometer data are leverage to capture X, Y, Z position. 15 seconds of data is captured every minute and the mean x, y, z data are reported as the positional vector. X, Y, Z data are turned into postural angle by calculating the angle of each point measurement from a reference vector of the patient in the supine state. | fix time of day grid. | The standard deviation across days is then calculated. The overall variability is the calculated as the average of the standard deviation. In subject 1, this is +−13.6 degrees. Taking adherence was 95.8% and timing adherence (% meds taken +−1 hour of dosing time) was 91.3% | comparable to this patient indicates strong likelihood adherence to a medication regimen. |
| Example 3: Patient 2 | IEM data are derived from an ingestible sensor (dose type of medicine, dose) and derived from patch receiver (dosing times, physiologic data such as heart rate, heart rate variability) | Data analyzed according to a predetermined formula to generate patient characterization | Metric used for characterization may include blood pressure, blood pressure increase over time, blood pressure increase compared to dosing and dose type), lifestyle based on sleep and activity data | Predictive information may be generated showing predicted future health event of a stroke and prediction for occurrence of stroke within one month if none of the variables are changed, e.g., dosing type, dosage, lifestyle, activity, etc. |
| Example 4 | Other data available from receiver: Skin temperature Heart-rate Activity levels Step-rate Activity class Other wearable devices: Mood (GSR) Caloric expenditure (GSR, heat-flux) Pulse Ox Data available from the mobile: Location (GPS) Environment (wi-fi networks in proximity) Sociability (messaging (email, SMS, social media) utilization, proximity to | Data is time-normalized and interpolated to a fix time of day grid. Transformations that can be applied to characterize patterns differently: Fourier, Wavelet, Harlett, principal/independent components Low-pass filtering Calculate daily residual from dominant mode (average day or principal component) | Calculate descriptive statistics of residual distributions (mean, std, kurtosis, skewness, entropy) Intrinsic dimensionality based on number of dominant modes (principal, independent components) | Characterization of patient stability on therapy. Characterization of patient state. Specifically in neuropsychiatric applications one can classify individuals in stable of manic states. Can be used to more effectively triage patients based on stability measures. Can be used to understand the risk profile of a population and better allocate health resources. |

TABLE 1-continued

"Examples"

| IEM Data 200 | Analysis Module 510a | Metrics Module 510b | Predictive Information Module 510c |
|---|---|---|---|
| other devices via Bluetooth ® devices in proximity) | | | |

Figure 24A:
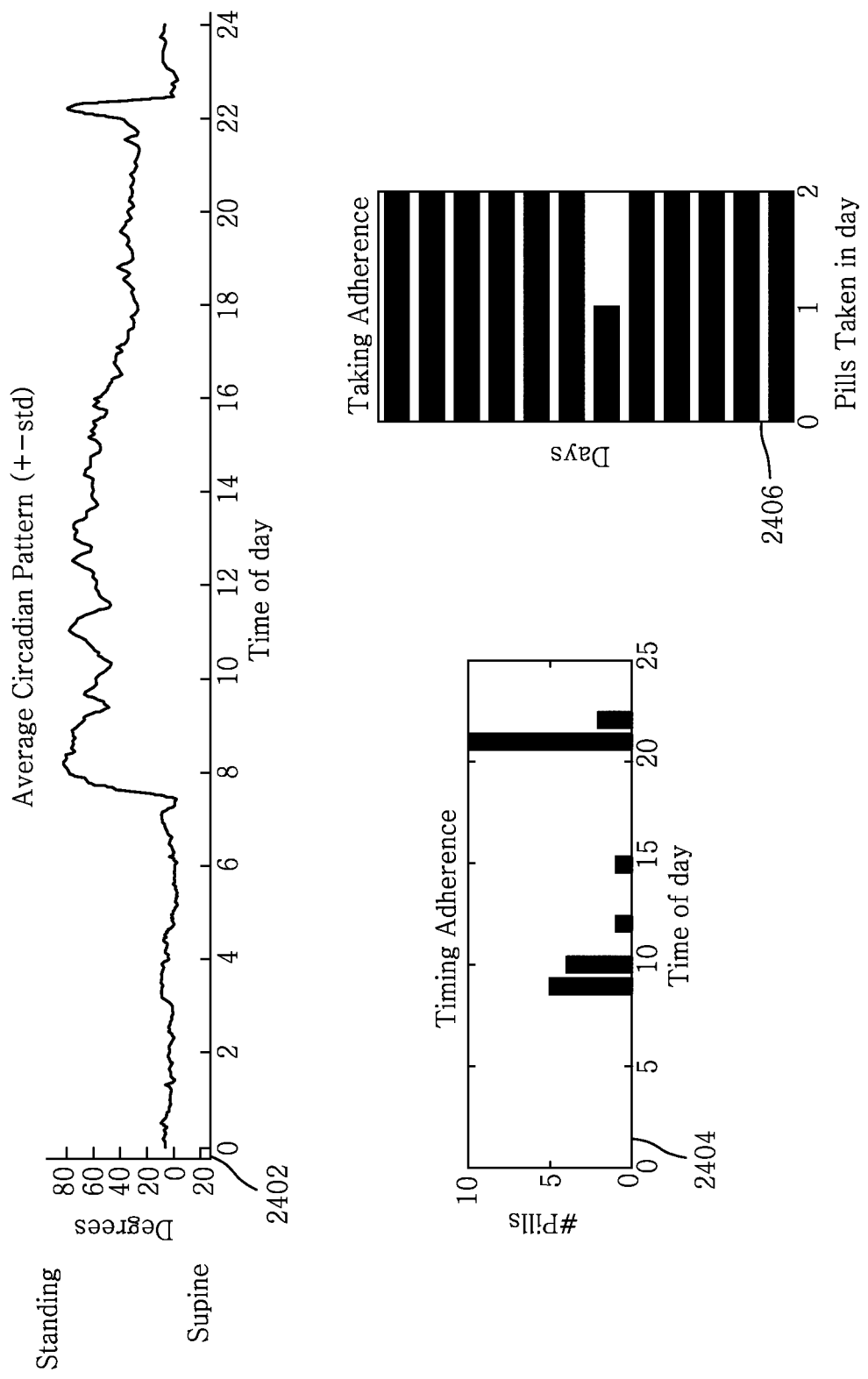
FIGS. 24a and 24b illustrate sample IEM data and sample metrics.
Figure 24B:
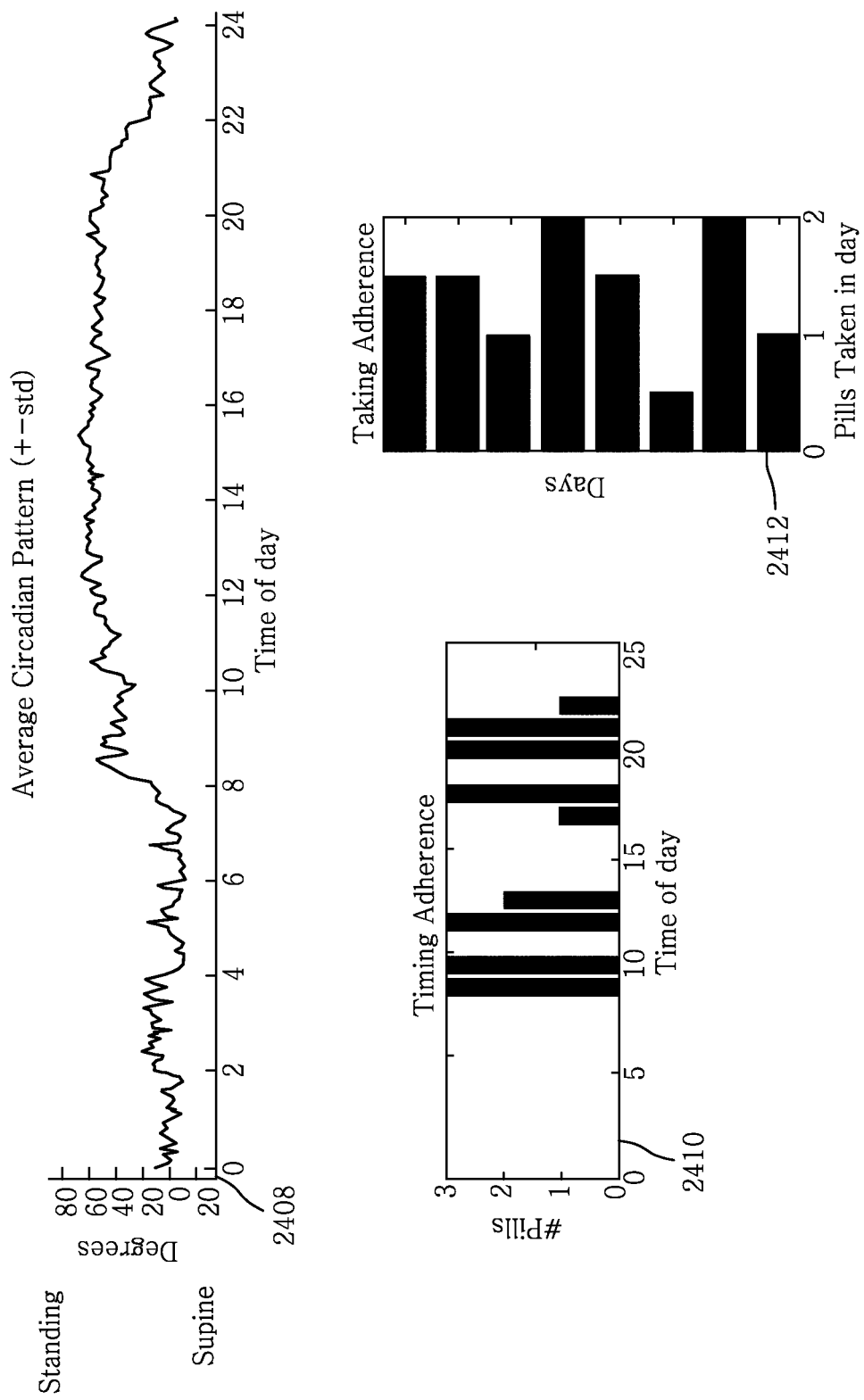

With continuing reference to Table 1 and with reference to FIGS. 24a and 24b, which illustrate sample IEM data and sample metrics as previously discussed, in example 1, analysis modules and metrics are used to assess the regularity and stability of the circadian (diurnal) pattern of the individual. These metrics are then used as surrogate markers of patient stability regularity and may be descriptive and/or predictive of patient pill taking behavior.

Sensor(s), data logger, and/or other IEM data sources may be used to capture time-stamped data pertaining to an individual. The data may related to the individual's physiology, e.g. heart-rate, activity, sleep, body/skin temperature, etc., behavior, e.g., mobility, sociability, engagement, technology use, etc., cognitive state, e.g., mood, stress, emotional state, etc., and/or environment, e.g. location, temperature, ambient light and sound, etc. The sensors may be active, i.e., worn and/or carried by individual, etc., or passive in nature, i.e., found in the individual's environment.

The analysis module applies algorithms to one or more data sources to visualize and characterize the circadian (diurnal) pattern. Pre-processing may include time normalization and interpolation of data samples to a fixed time of day to characterize regularity of daily pattern. Various filters or transformations may be applied to accentuate time-series features prior to metric calculation. Metrics related to variability of the daily pattern include standard deviation calculated across days, the intrinsic dimensionality calculated as number of significant principal components in the data series, the daily deviation in the average pattern and/or other time-series descriptive statistics.

The example provided in FIG. 24b relates to variability of the circadian rhythm to adherence to a medication regimen. Patient 1 has a regular, stable circadian pattern and demonstrates a high-rate of medication adherence while Patient 2 demonstrates both irregular circadian patterns and pill taking behavior.

The heat-maps represent the daily pattern of posture and pill taking behavior captured over multiple days. Patient 1 has a regular circadian pattern with relatively low standard deviation across twelve days of data capture. The individual also demonstrated high pill taking and timing adherence as reflected in the regularity of dose number and timing.

In contrast, Patient 2 has a more irregular pattern with relatively high levels of temporal standard deviation with respect to his average daily pattern. Irregularity in transition from standing to supine postural position is also evident in the longitudinal postural data. The individual also shows an irregular pill taking behavior, taking different number of pills per day and less controlled times within the day.

Further, any of the embodiments disclosed herein may be performed in a data processing system. To illustrate, a diagrammatic system comprises, for example, a processor, a main memory, a static memory, a bus, a video display, an alpha-numeric input device, a cursor control device, a drive unit, a signal generation device, a network interface device, a machine readable medium, instructions and a network, according to one embodiment.

The diagrammatic system may indicate a personal computer and/or a data processing system in which one or more operations disclosed herein may be performed. The processor may be a microprocessor, a state machine, an application-specific integrated circuit, a field programmable gate array, etc. The main memory may be a dynamic random access memory and/or a primary memory of a computer system. The static memory may be a hard drive, a flash drive, and/or other memory information associated with the data processing system.

The bus may be an interconnection between various circuits and/or structures of the data processing system. The video display may provide graphical representation of information on the data processing system. The alpha-numeric input device may be a keypad, a keyboard and/or any other input device of text, e.g., a special device to aid the physically challenged. The cursor control device may be a pointing device such as a mouse. The drive unit may be a hard drive, a storage system, and/or other longer term storage subsystem. The signal generation device may be a bios and/or a functional operating system of the data processing system. The network interface device may be a device that may perform interface functions such as code conversion, protocol conversion and/or buffering required for communication to and from the network. The machine readable medium may provide instructions on which any of the methods disclosed herein may be performed. The instructions may provide source code and/or data code to the processor to enable any one/or more operations disclosed herein.

Although the present embodiments have been described with reference to specific example embodiments, it will be evident that various modifications and changes may be made to these embodiments without departing from the broader spirit and scope of the various embodiments. For example, the various devices, modules, etc. described herein may be enabled and operated using hardware circuitry, e.g., CMOS based logic circuitry, firmware, software and/or any combination of hardware, firmware, and/or software, e.g., embodied in a machine readable medium.

For example, the various electrical structure and methods may be embodied using transistors, logic gates, and electrical circuits, e.g., Application Specific Integrated circuitry (ASIC) and/or in Digital Signal Processor (DSP) circuitry. For example, the receive module and the communicate module and other modules may be enabled using one or more of the technologies described herein.

In addition, it will be appreciated that the various operations, processes, and methods disclosed herein may be embodied in a machine-readable medium and/or a machine accessible medium compatible with a data processing system, e.g., a computer system, and may be performed in any order. Accordingly, the specification and drawings are to be regarded in an illustrative rather than a restrictive sense.

Any or all data associated with the aforementioned devices and methods, for example, may be used alone or in combination with other data to constitute IEM data, i.e., data having an IEM data aspect.

In certain embodiments, the system and/or method steps further includes/utilizes an element for storing data, i.e., a data storage element, where this element is present on an external device, such as a bedside monitor, PDA, smart phone, computer server, etc. Typically, the data storage element is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on a computer readable medium, where "storing" means recording information such that it is accessible and retrievable at a later data by a computer and/or computer-related component. With respect to computer readable media, "permanent memory" refers to memory that is permanent. Permanent memory is not erased by termination of the electrical supply to a computer of processor. Computer hard-drive ROM, i.e., not used as virtual memory, CD-ROM, floppy disk and DVD are all examples of permanent memory. Random Access Memory (RAM) is an example of non-permanent memory. A file in permanent memory may be editable and re-writable.

Also provided are computer executable instructions, i.e., programming, for performing the above methods, e.g., for programming the IEM, receiver, and other components of the system. The computer executable instructions are present on a computer readable medium. Accordingly, various aspects provide a computer readable medium containing programming for use in providing ingestible event marker data.

As such, in certain embodiments the systems include one or more of: a data storage element, a data processing element, a data display element, a data transmission element, a notification mechanism, and a user interface. These elements may be present or otherwise associated with at least one of the ingestible event marker data, the hub, and the IEM data systems.

One of the above-described systems is reviewed in terms of a receive module and a communicate module. The aspects, however, are not so limited. In a broader sense, the systems are composed of two or more different modules that communicate with each other, e.g., using the hub functionalities as reviewed above, e.g., using the IEM data in the communication, e.g., using the IEM data systems' functionalities.

It is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system comprising:
an ingestible event marker device configured to collect Ingestible Event Marker (IEM) data from a body of an individual and transmit a signal comprising the IEM data, wherein the IEM data comprise information associated with an ingestion event;
a receiver adapted to be associated with the body of the individual, the receiver configured to receive the signal comprising the IEM data via the body of the individual associated with the receiver;
a hub configured to receive the IEM data from the receiver; and
at least one IEM data system configured to:
receive the IEM data from the hub;
analyze the IEM data and generate at least one metric based on the IEM data; and
generate predictive information based on the at least one metric, wherein the predictive information is related to a prediction of a state of the individual.

2. The system of claim 1, wherein the receiver is selected from a group consisting of a patch receiver, an implantable receiver, a receiver configured to be worn on the body, an apparel-configured receiver, and a receiver adapted to be associated with the hub.

3. The system of claim 2, wherein the receiver adapted to be associated with the hub comprises a mobile phone attachment.

4. The system of claim 3, wherein the hub is a mobile phone.

5. The system of claim 1, wherein the at least one IEM data system further comprises software.

6. The system of claim 5, wherein the software further comprises at least one of an analysis module, a metrics module, and a predictive information module.

7. The system of claim 6, wherein the analysis module analyzes the IEM data.

8. The system of claim 6, wherein the metrics module generates the at least one metric based on the IEM data.

9. The system of claim 6, wherein the predictive information module generates the predictive information based on the IEM data.

10. The system of claim 6, wherein:
the IEM data further comprise physiologic data,
the analysis module analyzes the physiologic data and generates the at least one metric based on the physiologic data, and
the predictive module generates the predictive information based on the physiologic data.

11. The system of claim 1, wherein the at least one IEM data system comprises at least one of a feedback loop system and a decision support system.

12. The system of claim 1, wherein the receiver is configured to capture the IEM data at a predetermined rate.

13. The system of claim 1, wherein the IEM data comprises information relating to a dosage of medication.

14. The system of claim 1, wherein the receiver is configured to transmit additional data to the hub, and the at least one IEM data system to receive the additional data from the hub, wherein the additional data comprises data derived from the receiver.

15. The system of claim 14, wherein the at least one IEM data system analyzes the additional data derived from the receiver and generates at least one metric based on the IEM data and the additional data derived from the receiver.

16. The system of claim 14, wherein the additional data derived from the receiver comprises information regarding at least one of positional data, accelerometer data, dosing time, galvanic skin response, heat-flux, heart rate, or heart rate variability.

17. The system of claim 1, wherein the at least one metric comprises a circadian pattern of the individual.

18. The system of claim 17, wherein the at least one metric comprises a standard deviation of the circadian pattern of the individual across a predetermined number of days and an overall variability of the circadian pattern of the individual.

19. The system of claim 1, wherein the at least one metric comprises blood pressure, blood pressure increase over time, and blood pressure increase compared to dosing and dose type.

20. The system of claim 1, wherein the at least one IEM data system analyzes the IEM data such that the IEM data are time-normalized and interpolated to a time of day.

21. A system comprising:
an Ingestible Event Marker (IEM) device configured to collect IEM data from a body of an individual associated with the IEM device and transmit a signal comprising the IEM data, wherein the IEM data comprise information associated with an ingestion event; and
at least one IEM data system configured to process the IEM data, the at least one IEM data system comprising a processor and a non-transitory machine readable medium, wherein the non-transitory machine readable medium comprises instructions that when executed by the processor cause the processor to:
analyze the IEM data and generate at least one metric based on the IEM data; and
generate predictive information based on the at least one metric, wherein the predictive information is related to a prediction of a state of the individual;
wherein the IEM data is received from the body of the individual.

22. The system of claim 21, wherein the predictive information is associated with a likelihood of adherence to a medication regimen.

23. The system of claim 21, wherein the predictive information is associated with the prediction of occurrence of a future health event.

24. The system of claim 21, wherein the predictive information is associated with a characterization of patient stability while on a medication regimen.

25. A system comprising:
an ingestible event marker device configured to collect Ingestible Event Marker (IEM) data from a body of an individual and transmit a signal comprising the IEM data, wherein the IEM data comprise information associated with an ingestion event;
a receiver adapted to be associated with the body of the individual, the receiver configured to receive the signal comprising the IEM data via the body of the individual associated with the receiver;

a hub configured to receive the IEM data; and
at least one IEM data system configured to:
   receive the IEM data from the hub;
analyze the IEM data and generate at least one metric based on the IEM data; and
generate predictive information based on the at least one metric;
wherein the predictive information comprises an indication of a likelihood of adherence to a medication regimen.

* * * * *